US007514408B1

(12) United States Patent
John et al.

(10) Patent No.: US 7,514,408 B1
(45) Date of Patent: Apr. 7, 2009

(54) β-SECRETASE ENZYME COMPOSITIONS AND METHODS

(75) Inventors: Varghese John, San Francisco, CA (US); Sukanto Sinha, San Francisco, CA (US); Jay S. Tung, Belmont, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 60 days.

(21) Appl. No.: 09/730,329

(22) Filed: Dec. 4, 2000

Related U.S. Application Data

(60) Provisional application No. 60/168,854, filed on Dec. 2, 1999.

(51) Int. Cl.
*C07K 7/00* (2006.01)

(52) U.S. Cl. ........................ 514/16; 530/328; 530/329; 530/333; 530/350; 435/183; 435/184

(58) Field of Classification Search ................ 530/328, 530/329, 333, 334, 350; 514/16; 435/184, 435/183
See application file for complete search history.

(56) References Cited

U.S. PATENT DOCUMENTS

| | | | | |
|---|---|---|---|---|
| 5,424,205 | A | 6/1995 | Dovey et al. | |
| 5,455,169 | A | 10/1995 | Mullan | |
| 5,593,846 | A | 1/1997 | Schenk et al. | |
| 5,733,768 | A | 3/1998 | Dixon et al. | |
| 5,744,346 | A | 4/1998 | Chrysler et al. | |
| 5,750,349 | A | 5/1998 | Suzuki et al. | |
| 5,766,846 | A | 6/1998 | Schlossmacher et al. | |
| 5,795,963 | A | 8/1998 | Mullan | |
| 5,837,672 | A | 11/1998 | Schenk et al. | |
| 5,849,560 | A | 12/1998 | Abraham | |
| 5,863,756 | A | 1/1999 | Barr et al. | |
| 5,877,015 | A | 3/1999 | Hardy et al. | |
| 5,942,400 | A * | 8/1999 | Anderson et al. | 435/7.1 |
| 6,025,180 | A | 2/2000 | Powell et al. | |
| 6,162,630 | A | 12/2000 | Powell et al. | |
| 6,211,428 | B1 | 4/2001 | Singh et al. | |
| 6,221,645 | B1 | 4/2001 | Chrysler et al. | |
| 6,245,884 | B1 | 6/2001 | Hook | |
| 6,245,964 | B1 | 6/2001 | McLonlogue et al. | |
| 6,313,268 | B1 | 11/2001 | Hook | |
| 6,319,689 | B1 | 11/2001 | Powell et al. | |
| 6,329,163 | B1 | 12/2001 | Anderson et al. | |
| 6,358,725 | B1 | 3/2002 | Christie et al. | |
| 6,361,975 | B1 | 3/2002 | Christie et al. | |
| 6,420,534 | B1 | 7/2002 | Gurney et al. | |
| 6,440,698 | B1 | 8/2002 | Gurney et al. | |
| 6,500,667 | B1 | 12/2002 | Gurney et al. | |
| 6,627,739 | B1 | 9/2003 | Anderson | |
| 6,699,671 | B1 | 3/2004 | Gurney et al. | |
| 6,706,485 | B1 | 3/2004 | Gurney et al. | |
| 6,727,074 | B2 | 4/2004 | Gurney et al. | |
| 6,737,510 | B1 | 5/2004 | Gurney et al. | |
| 6,753,163 | B2 | 6/2004 | Gurney et al. | |
| 6,790,610 | B2 | 9/2004 | Gurney et al. | |
| 6,797,487 | B2 | 9/2004 | Gurney et al. | |
| 6,825,023 | B1 | 11/2004 | Gurney et al. | |
| 6,828,117 | B2 | 12/2004 | Gurney et al. | |
| 6,835,565 | B1 | 12/2004 | Gurney et al. | |
| 6,844,148 | B1 | 1/2005 | Gurney et al. | |
| 6,852,848 | B2 | 2/2005 | Gurney et al. | |
| 2001/0021391 | A1 | 9/2001 | Gurney et al. | |
| 2002/0037315 | A1 | 3/2002 | Gurney et al. | |
| 2002/0081634 | A1 | 6/2002 | Gurney et al. | |
| 2004/0043408 | A1 | 3/2004 | Gurney et al. | |
| 2004/0048303 | A1 | 3/2004 | Gurney et al. | |
| 2004/0166507 | A1 | 8/2004 | Gurney et al. | |
| 2004/0234976 | A1 | 11/2004 | Gurney et al. | |

FOREIGN PATENT DOCUMENTS

| | | | |
|---|---|---|---|
| EP | 848 062 | A2 | 6/1998 |
| EP | 855 442 | A2 | 7/1998 |
| EP | 855 444 | A2 | 7/1998 |
| EP | 1 445 263 | A1 | 8/2004 |
| GB | 2 364 059 | B | 1/2004 |
| GB | 2 389 113 | B | 2/2004 |
| GB | 2 389 114 | B | 2/2004 |
| GB | 2 389 182 | B | 2/2004 |
| WO | WO 96/20725 | A2 | 7/1996 |
| WO | WO 96/31122 | A1 | 10/1996 |
| WO | WO 96/40885 | A2 | 12/1996 |
| WO | WO 97/47314 | | 12/1997 |
| WO | WO 98/11236 | | 3/1998 |
| WO | WO 98/13488 | | 4/1998 |
| WO | WO 98/21589 | | 5/1998 |
| WO | WO 98/22597 | A2 | 5/1998 |
| WO | WO 98/26059 | | 6/1998 |
| WO | WO 98/37226 | A1 | 8/1998 |
| WO | WO 99/31236 | A2 | 6/1999 |
| WO | WO 99/34000 | A2 | 8/1999 |

(Continued)

OTHER PUBLICATIONS

U.S. Appl. No. 10/817,979, Gurney et al.

(Continued)

*Primary Examiner*—Chih-Min Kam
(74) *Attorney, Agent, or Firm*—Townsend and Townsend and Crew, LLP

(57) ABSTRACT

Disclosed is an active, isolated β-secretase enzyme in purified and recombinant form. This enzyme is implicated in the production of amyloid plaque components which accumulate in the brains of individuals afflicted with Alzheimer's disease. Recombinant cells that produce this enzyme either alone or in combination with some of its natural substrates (APP and APPsw) are also disclosed. These compositions are useful for use in methods of selecting compounds that modulate β-secretase. Inhibitors of β-secretase are implicated as therapeutics in the treatment of neurodegenerative diseases, such as Alzheimer's disease.

6 Claims, 51 Drawing Sheets

FOREIGN PATENT DOCUMENTS

| | | | |
|---|---|---|---|
| WO | WO 99/46281 | A2 | 9/1999 |
| WO | WO 99/64587 | A1 | 12/1999 |
| WO | WO 00/17369 | A2 | 3/2000 |
| WO | WO 00/23576 | A2 | 4/2000 |
| WO | WO 00/47618 | A3 | 8/2000 |
| WO | WO 00/56871 | A2 | 9/2000 |
| WO | WO 00/58479 | A1 | 10/2000 |
| WO | WO 00/68266 | A1 | 11/2000 |
| WO | WO 00/69262 | A1 | 11/2000 |
| WO | WO 01/00663 | A2 | 1/2001 |
| WO | WO 01/00665 | A2 | 1/2001 |
| WO | WO 01/23533 | A2 | 4/2001 |
| WO | WO 01/29563 | A1 | 4/2001 |
| WO | WO 01/31054 | A1 | 5/2001 |
| WO | WO 01/36600 | A1 | 5/2001 |
| WO | WO 01/38487 | A2 | 5/2001 |
| WO | WO 01/49097 | A2 | 7/2001 |
| WO | WO 01/49098 | A2 | 7/2001 |
| WO | WO 01/50829 | A2 | 7/2001 |

OTHER PUBLICATIONS

U.S. Appl. No. 10/477,076, Gurney et al.
U.S. Appl. No. 09/668,314, filed Mar. 12, 2002, Gurney et al.
U.S. Appl. No. 09/548,370, filed May 9, 2006, Gurney et al.
U.S. Appl. No. 09/548,369, Gurney et al.
U.S. Appl. No. 09/548,365, filed Mar. 15, 2005, Gurney et al.
U.S. Appl. No. 09/404,133, Gurney et al.
U.S. Appl. No. 09/277,229, Citron et al.
U.S. Appl. No. 60/210,292, Hong et al.
U.S. Appl. No. 60/178,368, Lin et al.
U.S. Appl. No. 60/177,836, Lin et al.
U.S. Appl. No. 60/169,232, Gurney et al.
U.S. Appl. No. 60/168,060, Lin et al.
U.S. Appl. No. 60/155,493, Gurney et al.
U.S. Appl. No. 60/141,363, Lin et al.
U.S. Appl. No. 60/139,172, Anderson et al.
U.S. Appl. No. 60/119,571, Basi et al.
U.S. Appl. No. 60/114,408, Basi et al.
U.S. Appl. No. 60/101,594, Gurney et al.
Baldwin et al., "Crystal structures of native and inhibited forms of human cathepsin D: Implications for lysosomal targeting and drug design," *PNAS*, 90:6796-6800 (1993).
Bork, P., "Powers and Pitfalls in Sequence Analysis: The 70% Hurdle," *Genome Research*, 10:398-400 (2000).
Broun et al., "Catalytic Plasticity of Fatty Acid Modification Enzymes Underlying Chemical Diversity," *Science*, 282:131-133 (1998).
Brown et al., "Evaluation of Cathepsins D and G and EC 3.4.24.15 as Candidate β-Secretase Proteases Using Peptide and Amyloid Precursor Protein Substrates," *Journal of Neurochemistry*, 66:2436-2445 (1996).
Chevallier et al., "Cathepsin D displays in vitro β-secretase-like specificity," *Brain Research*, 750:11-19 (1997).
Chyung et al., "Novel β-Secretase Cleavage of β-Amyloid Precursor Protein in the Endoplasmic Reticulum/Intermediate Compartment of NT2N Cells," *Journal of Cell Biology*, 138:671-680 (1997).
Das et al., "Estrogenic responses in estrogen receptor-α deficient mice reveal a distinct estrogen signaling pathway," *PNAS*, 94:12786-12791 (1997).
Declaration of Michael Bienkowski, Ph.D. in U.S. Appl. No. 09/548,368, (2001).
Dennis et al., "Kunitz Domain Inhibitors of Tissue Factor-Factor Vlla," *J. Biol. Chem.*, 269(35):22129-22136 (1994).
Diedrich et al., "Nucleotide sequence of a cDNA encoding mouse cathepsin D," *Nucleic Acids Research*, 18:7184 (1990).
Elan Corporation, plc and Pharmacia Corporation announce research collaboration, News Aug. 9, 2000, www.elancorp.com.
Examination Report for United Kingdom Application 001211314.9 dated Nov. 1, 2002.
Examination Report for United Kingdom Application 00121314.9 dated Jul. 21, 2003.
Examination Report for United Kingdom Application 00121314.9 dated Oct. 30, 2003.
Examination Report for United Kingdom Application 0318112.0 dated Nov. 19, 2003.
Search and Examination Report for United Kingdom Application 0318112.0 dated Sep. 24, 2003.
Search and Examination Report for United Kingdom Application 0318107.0 dated Sep. 25, 2003.
Search and Examination Report for United Kingdom Application 0318113.8 dated Sep. 25, 2003.
Examination Report for United Kingdom Application 0318113.8 dated Nov. 19, 2003.
Examination Report for European Application 00919298.0 dated Oct. 30, 2003.
Search Report for European Application 04006991.6 dated Jun. 11, 2004.
Examination Report for New Zealand Application 534876 dated Aug. 27, 2004.
Examination Report for European Application 00919298.0 dated Sep. 20, 2004.
International Preliminary Examination Report for PCT application PCT/US00/03819 dated Sep. 4, 2002.
Evin et al., "Alzheimer's disease amyloid precursor protein (βAPP): proteolytic processing, secretases and βA4 amyloid production," *Amyloid; Int. J. Exp. Clin. Invest.* 1:263-280 (1994).
Haass et al., "Amyloid β-peptide is Produced by Cultured Cells During Normal Metabolism," *Nature*, 359:322-325 (1992).
Haass et al., "The Swedish Mutation Causes Early-Onset Alzheimer's Disease by β-Secretase Cleavage Within the Secretory Pathway," *Nature Medicine*, 12:1291-1296 (1995).
Haass et al., "β-Amyloid Peptide and 3-kDa Fragment are Derived by Distinct Cellular Mechanisms," *Journal of Biochemistry*, 268:3021-3024 (1993).
Hardy, J., "Framing beta-amyloid," *Nature Genetics*, 1(4):233-234 (1992).
Hirosawa et al., "Characterization of cDNA Clones Selected by the GeneMark Analysis from Size-Fractionated cDNA Libraries From Human Brain," *DNA Res.*, 6(5):329-336 (1999).
Hussain et al., "Identification of a Novel Aspartic Protease (Asp 2) as β-Secretase," *Molecular and Cellular Neuroscience*, 14:419-427 (1999).
Jackson et al., "The $p47^{phox}$ Mouse Knock-Out Model of Chronic Granutomatous Disease," *J. Exp. Med.*, 182:751-758 (1995).
Kang et al., "The Precursor of Alzheimer's Disease Amyloid A4 Protein Resembles a Cell-Surface Receptor," *Nature*, 325:733-736 (1987).
Kick et al., "Structure-based design and combinatorial chemistry yield low nanomolar inhibitors of cathepsin D," *Chem. & Biol.*, 4:297-307 (1997).
Kitaguchi et al., "Novel Precursor of Alzheimer's Disease Amyloid Protein Shows Protease Inhibitory Activity," *Nature*, 331:530-532 (1988).
Knops et al., "Cell-type and Amyloid Precursor Protein-type Specific Inhibition of Aβ Release by Bafilomycin A1, a Selective Inhibitor of Vacuolar ATPases," *Journal of Biological Chemistry*, 270:2419-2422 (1995).
Koo et al., "Evidence that Production and Release of Amyloid β-Protein Involves the Endocytic Pathway," *Journal of Biological Chemistry*, 269:17386-17389 (1994).
Kristie, T. M., "The Mouse Homologue of the Human Transcription Factor C1 (Host Cell Factor)," *J. Biol. Chem.*, 272(42):26749-26755 (1997).
Kuntz, I. D., "Structure-Based Strategies for Drug Design and Discovery," *Science*, 257:1078-1082 (1992).
Li et al., "Cloning and Characterization of Three New Murine Genes Encoding Short Homologues of RNase P RNA*," *J. Biol. Chem.*, 270(42):25281-25285 (1995).
Majer et al., "Structure-based subsite specificity mapping of human cathepsin D using statine-based inhibitors," *Protein Science*, 6:1458-1466 (1997).

Mullan et al., "A Pathogenic Mutation for Probable Alzheimer's Disease in the APP Gene at the N-Terminus of β-Amyloid," *Nature Genetics*, 1: 345-347 (1992).

Office Action dated May 6, 2002 in U.S. Appl. No. 09/548,368, (2002).

PCT Search report for PCT/US99/20881, (2000).

PCT Search report for PCT/US00/03819, (2002).

Ponte et al., "A New A4 Amyloid mRNA Contains a Domain Homologous to Serine Proteinase Inhibitors," *Nature*, 331:525-527 (1988).

Raabe et al., "Knockout of the abetalipoproteinemia gene in mice: Reduced lipoprotein secretion in heterozygotes and embryonic lethality in homozygotes," *PNAS*, 95:8686-8691 (1998).

Saftig et al., "Amyloidogenic Processing of Human Amyloid Precursor Protein in Hippocampal Neurons Devoid of Cathepsin D," *Journal of Biological Chemistry*, 271:27241-27244 (1996).

Schechter et al., "On the size of the active site in proteases. I. Papain," *Biochemical and Biophysical Research Communications*, 27:157-162 (1967).

Seubert et al., "Secretion of β-amyloid Precursor Protein Cleaved at the Amino Terminus of the β-amyloid Peptide," *Nature*, 361:260-263 (1993).

Sinha et al., "Purification and Cloning of Amyloid Precursor Protein β-Secretase from Human Brain," *Nature*, 402:537-540 (1999).

Sun et al., "Gene Structure, Chromosomal Localization, and Expression of the Murine Homologue of Human Proteinase Inhibitor 6 (Pl-6) Suggests Divergence of Pl-6 from the Ovalbumin Serpins*," *J. Biol. Chem.*, 270(27): 16089-16096 (1995).

Szecsi, "The Aspartic Proteases," *Scand. J. Clin. Lab. Invest.*, 52 (suppl. 210): 5-22 (1992).

Tang et al., "Evolution in the Structure and Function of Aspartic Proteases," *J. Cellular Biochem.*, 33:53-63 (1987).

Tanzi et al., "Protease Inhibitor Domain Encoded by an Amyloid Protein Precursor mRNA Associated with Alzheimer's Disease," *Nature*, 331:528-530 (1988).

Thompson et al., "Expression and characterization of human β-Secretase from candidates metalloendopeptidase MP78 and cathepsin D in βAPP-overexpressing cells," *Molecular Brain Research*, 48(2):206-214 (1997).

Umans et al., "Targeted Inactivation of the Mouse $_{a2}$-Macroglobulin Gene*," *J. Biol. Chem.*, 270(34):19778-19785 (1995).

Van De Loo et al., "An oleate 12-hydroxylase from *Ricinus communis* L. is a fatty acyl desaturase homolog," *PNBS*, 92:6743-6747 (1995).

Vasser et al., "β-secretase Cleavage of Alzheimer's Amyloid Precursor Protein by the Transmembrane Aspartic Protease BACE," *Science*, 286(5440):735-741 (1999).

Viswanadhan et al., "An Approach to Rapid Estimation of Relative Binding Affinites of Enzyme Inhibitors: Application to Peptidomimetic Inhibitors of the Human Immunodeficiency Virus Type 1 Protease," *J. Med. Chem.*, 39:705-712 (1996).

Yan et al., "Membrane-anchored Aspartyl Protease with Alzheimer's Disease β-Secretase Activity," *Nature*, 402:533-537 (1999).

Young et al., "HIV-1 Protease Inhibitors Based on Hydroxyethylene Dipeptide Isosteres: An Investigation into the Role of the $P_1$Side Chain on Structure-Activity," *J. Med. Chem.*, 35:1702-1709 (1992).

Zhao et al., "β-Secretase Processing of the β-Amyloid Precursor Protein in Transgenic Mice Is Efficient in Neurons but Inefficient in Astrocytes," *Journal of Biological Chemistry*, 271:31407-31411 (1996).

* cited by examiner

ATGGCCCAAGCCCTGCCCTGGCTCCTGCTGTGGATGGCGCGGGAG
TGCTGCCTGCCCACGGCACCCAGCACGGCATCCGGCTGCCCCTGCG
CAGCGGCCTGGGGGGCGCCCCCCTGGGGCTGCGGCTGCCCCGGGA
GACCGACGAAGAGCCCGAGGAGCCCGGCCGGAGGGGCAGCTTTGT
GGAGATGGTGGACAACCTGAGGGGCAAGTCGGGGCAGGGCTACTAC
GTGGAGATGACCGTGGGCAGCCCCCCGCAGACGCTCAACATCCTGG
TGGATACAGGCAGCAGTAACTTTGCAGTGGGTGCTGCCCCCCACCC
CTTCCTGCATCGCTACTACCAGAGGCAGCTGTCCAGCACATACCGGG
ACCTCCGGAAGGGTGTGTATGTGCCCTACACCCAGGGCAAGTGGGA
AGGGGAGCTGGGCACCGACCTGGTAAGCATCCCCCATGGCCCCAAC
GTCACTGTGCGTGCCAACATTGCTGCCATCACTGAATCAGACAAGTT
CTTCATCAACGGCTCCAACTGGGAAGGCATCCTGGGGCTGGCCTATG
CTGAGATTGCCAGGCCTGACGACTCCCTGGAGCCTTTCTTTGACTCT
CTGGTAAAGCAGACCCACGTTCCCAACCTCTTCTCCCTGCAGCTTTG
TGGTGCTGGCTTCCCCCTCAACCAGTCTGAAGTGCTGGCCTCTGTCG
GAGGGAGCATGATCATTGGAGGTATCGACCACTCGCTGTACACAGGC
AGTCTCTGGTATACACCCATCCGGCGGGAGTGGTATTATGAGGTGAT
CATTGTGCGGGTGGAGATCAATGGACAGGATCTGAAAATGGACTGCA
AGGAGTACAACTATGACAAGAGCATTGTGGACAGTGGCACCACCAAC
CTTCGTTTGCCCAAGAAAGTGTTTGAAGCTGCAGTCAAATCCATCAAG
GCAGCCTCCTCCACGGAGAAGTTCCCTGATGGTTTCTGGCTAGGAGA
GCAGCTGGTGTGCTGGCAAGCAGGCACCACCCCTTGGAACATTTTCC
CAGTCATCTCACTCTACCTAATGGGTGAGGTTACCAACCAGTCCTTCC
GCATCACCATCCTTCCGCAGCAATACCTGCGGCCAGTGGAAGATGTG
GCCACGTCCCAAGACGACTGTTACAAGTTTGCCATCTCACAGTCATC
CACGGGCACTGTTATGGGAGCTGTTATCATGGAGGGCTTCTACGTTG
TCTTTGATCGGGCCCGAAAACGAATTGGCTTTGCTGTCAGCGCTTGC
CATGTGCACGATGAGTTCAGGACGGCAGCGGTGGAAGGCCCTTTTG
TCACCTTGGACATGGAAGACTGTGGCTACAACATTCCACAGACAGAT
GAGTCAACCCTCATGACCATAGCCTATGTCATGGCTGCCATCTGCGC
CCTCTTCATGCTGCCACTCTGCCTCATGGTGTGTCAGTGGCGCTGCC
TCCGCTGCCTGCGCCAGCAGCATGATGACTTTGCTGATGACATCTCC
CTGCTGAAG

FIG. 1A

CCATGCCGGCCCCTCACAGCCCCGCCGGGAGCCCGAGCCCGCTGCCCAGG
CTGGCCGCCGCSGTGCCGATGTAGCGGGCTCCGGATCCCAGCCTCTCCCCT
GCTCCCGTGCTCTGCGGATCTCCCCTGACCGCTCTCCACAGCCCGGACCCG
GGGGCTGGCCCAGGGCCCTGCAGGCCCTGGCGTCCTGATGCCCCCAAGCT
CCCTCTCCTGAGAAGCCACCAGCACCACCCAGACTTGGGGGCAGGCGCCA
GGGACGGACGTGGGCCAGTGCGAGCCCAGAGGGCCCGAAGGCCGGGGCC
CACCATGGCCCAAGCCCTGCCCTGGCTCCTGCTGTGGATGGGCGCGGGAG
TGCTGCCTGCCCACGGCACCCAGCACGGCATCCGGCTGCCCCTGCGCAGC
GGCCTGGGGGGCGCCCCCCTGGGGCTGCGGCTGCCCCGGGAGACCGACG
AAGAGCCCGAGGAGCCCGGCCGGAGGGGCAGCTTTGTGGAGATGGTGGAC
AACCTGAGGGGCAAGTCGGGGCAGGGCTACTACGTGGAGATGACCGTGGG
CAGCCCCCCGCAGACGCTCAACATCCTGGTGGATACAGGCAGCAGTAACTT
TGCAGTGGGTGCTGCCCCCCACCCCTTCCTGCATCGCTACTACCAGAGGCA
GCTGTCCAGCACATACCGGGACCTCCGGAAGGGTGTGTATGTGCCCTACAC
CCAGGGCAAGTGGGAAGGGGAGCTGGGCACCGACCTGGTAAGCATCCCCC
ATGGCCCCAACGTCACTGTGCGTGCCAACATTGCTGCCATCACTGAATCAGA
CAAGTTCTTCATCAACGGCTCCAACTGGGAAGGCATCCTGGGGCTGGCCTAT
GCTGAGATTGCCAGGCCTGACGACTCCCTGGAGCCTTTCTTTGACTCTCTGG
TAAAGCAGACCCACGTTCCCAACCTCTTCTCCCTGCAGCTTTGTGGTGCTGG
CTTCCCCCTCAACCAGTCTGAAGTGCTGGCCTCTGTCGGAGGGAGCATGAT
CATTGGAGGTATCGACCACTCGCTGTACACAGGCAGTCTCTGGTATACACCC
ATCCGGCGGGAGTGGTATTATGAGGTGATCATTGTGCGGGTGGAGATCAAT
GGACAGGATCTGAAAATGGACTGCAAGGAGTACAACTATGACAAGAGCATTG
TGGACAGTGGCACCACCAACCTTCGTTTGCCCAAGAAAGTGTTTGAAGCTGC
AGTCAAATCCATCAAGGCAGCCTCCTCCACGGAGAAGTTCCCTGATGGTTTC
TGGCTAGGAGAGCAGCTGGTGTGCTGGCAAGCAGGCACCACCCCTTGGAAC
ATTTTCCCAGTCATCTCACTCTACCTAATGGGTGAGGTTACCAACCAGTCCTT
CCGCATCACCATCCTTCCGCAGCAATACCTGCGGCCAGTGGAAGATGTGGC
CACGTCCCAAGACGACTGTTACAAGTTTGCCATCTCACAGTCATCCACGGGC
ACTGTTATGGGAGCTGTTATCATGGAGGGCTTCTACGTTGTCTTTGATCGGG
CCCGAAAACGAATTGGCTTTGCTGTCAGCGCTTGCCATGTGCACGATGAGTT
CAGGACGGCAGCGGTGGAAGGCCCTTTTGTCACCTTGGACATGGAAGACTG
TGGCTACAACATTCCACAGACAGATGAGTCAACCCTCATGACCATAGCCTAT
GTCATGGCTGCCATCTGCGCCCTCTTCATGCTGCCACTCTGCCTCATGGTGT
GTCAGTGGCGCTGCCTCCGCTGCCTGCGCCAGCAGCATGATGACTTTGCTG
ATGACATCTCCCTGCTGAAGTGAGGAGGCCCATGGGCAGAAGATAGAGATT
CCCCTGGACCACACCTCCGTGGTTCACTTTGGTCACAAGTAGGAGACACAGA
TGGCACCTGTGGCCAGAGCACCTCAGGACCCTCCCCACCCACCAAATGCCT
CTGCCTTGATGGAGAAGGAAAAGGCTGGCAAGGTGGGTTCCAGGGACTGTA
CCTGTAGGAAACAGAAAAGAGAAGAAAGAAGCACTCTGCTGGCGGGAATAC
TCTTGGTCACCTCAAATTTAAGTCGGGAAATTCTGCTGCTTGAAACTTCAGCC
CTGAACCTTTGTCCACCATTCCTTTAAATTCTCCAACCCAAAGTATTCTTCTTT
TCTTAGTTTCAGAAGTACTGGCATCACACGCAGGTTACCTTGGCGTGTGTCC
CTGTGGTACCCTGGCAGAGAAGAGACCAAGCTTGTTTCCCTGCTGGCCAAA
GTCAGTAGGAGAGGATGCACAGTTTGCTATTTGCTTTAGAGACAGGGACTGT
ATAAACAAGCCTAACATTGGTGCAAAGATTGCCTCTTGAATT

FIG. 1B

MAQALPWLLLWMGAGVLPAHGTQHGIRLPLRSGLGGAPLGLRL
PRETDEEPEEPGRRGSFVEMVDNLRGKSGQGYYVEMTVGSPP
QTLNILVDTGSSNFAVGAAPHPFLHRYYQRQLSSTYRDLRKGVY
VPYTQGKWEGELGTDLVSIPHGPNVTVRANIAAITESDKFFINGS
NWEGILGLAYAEIARPDDSLEPFFDSLVKQTHVPNLFSLQLCGAG
FPLNQSEVLASVGGSMIIGGIDHSLYTGSLWYTPIRREWYYEVIIV
RVEINGQDLKMDCKEYNYDKSIVDSGTTNLRLPKKVFEAAVKSIK
AASSTEKFPDGFWLGEQLVCWQAGTTPWNIFPVISLYLMGEVTN
QSFRITILPQQYLRPVEDVATSQDDCYKFAISQSSTGTVMGAVIM
EGFYVVFDRARKRIGFAVSACHVHDEFRTAAVEGPFVTLDMEDC
GYNIPQTDESTLMTIAYVMAAICALFMLPLCLMVCQWRCLRCLR
QQHDDFADDISLLK

FIG. 2A

ETDEEPEEPGRRGSFVEMVDNLRGKSGQGYYVEMTVGSPPQT
LNILVDTGSSNFAVGAAPHPFLHRYYQRQLSSTYRDLRKGVYVP
YTQGKWEGELGTDLVSIPHGPNVTVRANIAAITESDKFFINGSNW
EGILGLAYAEIARPDDSLEPFFDSLVKQTHVPNLFSLQLCGAGFP
LNQSEVLASVGGSMIIGGIDHSLYTGSLWYTPIRREWYYEVIIVRV
EINGQDLKMDCKEYNYDKSIVDSGTTNLRLPKKVFEAAVKSIKAA
SSTEKFPDGFWLGEQLVCWQAGTTPWNIFPVISLYLMGEVTNQ
SFRITILPQQYLRPVEDVATSQDDCYKFAISQSSTGTVMGAVIME
GFYVVFDRARKRIGFAVSACHVHDEFRTAAVEGPFVTLDMEDC
GYNIPQTDESTLMTIAYVMAAICALFMLPLCLMVCQWRCLRCLR
QQHDDFADDISLLK

FIG. 2B

MAQALPWLLLWMGAGVLPAHGTQHGIRLPLRSGLGGAPLGLRL
PRETDEEPEEPGRRGSFVEMVDNLRGKSGQGYYVEMTVGSPP
QTLNILVDTGSSNFAVGAAPHPFLHRYYQRQLSSTYRDLRKGVY
VPYTQGKWEGELGTDLVSIPHGPNVTVRANIAAITESDKFFINGS
NWEGILGLAYAEIARPDDSLEPFFDSLVKQTHVPNLFSLQLCGAG
FPLNQSEVLASVGGSMIIGGIDHSLYTGSLWYTPIRREWYYEVIIV
RVEINGQDLKMDCKEYNYDKSIVDSGTTNLRLPKKVFEAAVKSIK
AASSTEKFPDGFWLGEQLVCWQAGTTPWNIFPVISLYLMGEVTN
QSFRITILPQQYLRPVEDVATSQDDCYKFAISQSSTGTVMGAVIM
EGFYVVFDRARKRIGFAVSACHVHDEFRTAAVEGPFVTLDMEDC
GYNIPQTDE<u>DYKDDDDK</u>

FIG. 3A

ETDEEPEEPGRRGSFVEMVDNLRGKSGQGYYVEMTVGSPPQT
LNILVDTGSSNFAVGAAPHPFLHRYYQRQLSSTYRDLRKGVYVP
YTQGKWEGELGTDLVSIPHGPNVTVRANIAAITESDKFFINGSNW
EGILGLAYAEIARPDDSLEPFFDSLVKQTHVPNLFSLQLCGAGFP
LNQSEVLASVGGSMIIGGIDHSLYTGSLWYTPIRREWYYEVIIVRV
EINGQDLKMDCKEYNYDKSIVDSGTTNLRLPKKVFEAAVKSIKAA
SSTEKFPDGFWLGEQLVCWQAGTTPWNIFPVISLYLMGEVTNQ
SFRITILPQQYLRPVEDVATSQDDCYKFAISQSSTGTVMGAVIME
GFYVVFDRARKRIGFAVSACHVHDEFRTAAVEGPFVTLDMEDC
GYNIPQTDE<u>DYKDDDDK</u>

NH2-K-T-E-E-I-S-E-V-N-Sta-V-A-E-F-COOH

Fig. 5A

```
atg gcc caa gcc ctg ccc tgg ctc ctg ctg tgg atg ggc gcg gga gtg   48
Met Ala Gln Ala Leu Pro Trp Leu Leu Leu Trp Met Gly Ala Gly Val
 1               5                  10                  15
                     Signal peptide

ctg cct gcc cac ggc acc cag cac ggc atc cgg ctg ccc ctg cgc agc   96
Leu Pro Ala His Gly Thr Gln His Gly Ile Arg Leu Pro Leu Arg Ser
             20                  25                  30
     Signal peptide                    pro region

ggc ctg ggg ggc gcc ccc ctg ggg ctg cgg ctg ccc cgg gag acc gac   144
Gly Leu Gly Gly Ala Pro Leu Gly Leu Arg Leu Pro Arg Glu Thr Asp
         35                  40                  45
                pro region                      N term seq

gaa gag ccc gag gag ccc ggc cgg agg ggc agc ttt gtg gag atg gtg   192
Glu Glu Pro Glu Glu Pro Gly Arg Arg Gly Ser Phe Val Glu Met Val
     50                  55                  60
                     N terminal sequence

gac aac ctg agg ggc aag tcg ggg cag ggc tac tac gtg gag atg acc   240
Asp Asn Leu Arg Gly Lys Ser Gly Gln Gly Tyr Tyr Val Glu Met Thr
 65                  70                  75                  80
N terminal sequence

gtg ggc agc ccc ccg cag acg ctc aac atc ctg gtg gat aca ggc agc   288
Val Gly Ser Pro Pro Gln Thr Leu Asn Ile Leu Val Asp Thr Gly Ser
                 85                  90                  95
                                               Active-D

agt aac ttt gca gtg ggt gct gcc ccc cac ccc ttc ctg cat cgc tac   336
Ser Asn Phe Ala Val Gly Ala Ala Pro His Pro Phe Leu His Arg Tyr
            100                 105                 110
```

Fig. 5B

```
tac cag agg cag ctg tcc agc aca tac cgg gac ctc cgg aag ggt gtg   384
Tyr Gln Arg Gln Leu Ser Ser Thr Tyr Arg Asp Leu Arg Lys Gly Val
        115                 120                 125

tat gtg ccc tac acc cag ggc aag tgg gaa ggg gag ctg ggc acc gac   432
Tyr Val Pro Tyr Thr Gln Gly Lys Trp Glu Gly Glu Leu Gly Thr Asp
    130                 135                 140

ctg gta agc atc ccc cat ggc ccc aac gtc act gtg cgt gcc aac att   480
Leu Val Ser Ile Pro His Gly Pro Asn Val Thr Val Arg Ala Asn Ile
145                 150                 155                 160
                                [ N-glycos ]

gct gcc atc act gaa tca gac aag ttc ttc atc aac ggc tcc aac tgg   528
Ala Ala Ile Thr Glu Ser Asp Lys Phe Phe Ile Asn Gly Ser Asn Trp
                165                 170                 175
                                        [ N-glycos  ]
gaa ggc atc ctg ggg ctg gcc tat gct gag att gcc agg cct gac gac   576
Glu Gly Ile Leu Gly Leu Ala Tyr Ala Glu Ile Ala Arg Pro Asp Asp
            180                 185                 190

tcc ctg gag cct ttc ttt gac tct ctg gta aag cag acc cac gtt ccc   624
Ser Leu Glu Pro Phe Phe Asp Ser Leu Val Lys Gln Thr His Val Pro
        195                 200                 205

aac ctc ttc tcc ctg cag ctt tgt ggt gct ggc ttc ccc ctc aac cag   672
Asn Leu Phe Ser Leu Gln Leu Cys Gly Ala Gly Phe Pro Leu Asn Gln
    210                 215                 220
                                                  [N-glycos]
```

Fig. 5C

```
tct gaa gtg ctg gcc tct gtc gga ggg agc atg atc att gga ggt atc    720
Ser Glu Val Leu Ala Ser Val Gly Gly Ser Met Ile Ile Gly Gly Ile
225                 230                 235                 240
N-gly

gac cac tcg ctg tac aca ggc agt ctc tgg tat aca ccc atc cgg cgg    768
Asp His Ser Leu Tyr Thr Gly Ser Leu Trp Tyr Thr Pro Ile Arg Arg
                245                 250                 255

gag tgg tat tat gag gtg atc att gtg cgg gtg gag atc aat gga cag    816
Glu Trp Tyr Tyr Glu Val Ile Ile Val Arg Val Glu Ile Asn Gly Gln
            260                 265                 270

gat ctg aaa atg gac tgc aag gag tac aac tat gac aag agc att gtg    864
Asp Leu Lys Met Asp Cys Lys Glu Tyr Asn Tyr Asp Lys Ser Ile Val
        275                 280                 285

gac agt ggc acc acc aac ctt cgt ttg ccc aag aaa gtg ttt gaa gct    912
Asp Ser Gly Thr Thr Asn Leu Arg Leu Pro Lys Lys Val Phe Glu Ala
    290                 295                 300

Active-D
gca gtc aaa tcc atc aag gca gcc tcc tcc acg gag aag ttc cct gat    960
Ala Val Lys Ser Ile Lys Ala Ala Ser Ser Thr Glu Lys Phe Pro Asp
305                 310                 315                 320

ggt ttc tgg cta gga gag cag ctg gtg tgc tgg caa gca ggc acc acc   1008
Gly Phe Trp Leu Gly Glu Gln Leu Val Cys Trp Gln Ala Gly Thr Thr
                325                 330                 335
```

Fig. 5D

```
cct tgg aac att ttc cca gtc atc tca ctc tac cta atg ggt gag gtt   1056
Pro Trp Asn Ile Phe Pro Val Ile Ser Leu Tyr Leu Met Gly Glu Val
            340                 345                 350

acc aac cag tcc ttc cgc atc acc atc ctt ccg cag caa tac ctg cgg   1104
Thr Asn Gln Ser Phe Arg Ile Thr Ile Leu Pro Gln Gln Tyr Leu Arg
        355                 360                 365

    [N-glycos  ]
cca gtg gaa gat gtg gcc acg tcc caa gac gac tgt tac aag ttt gcc   1152
Pro Val Glu Asp Val Ala Thr Ser Gln Asp Asp Cys Tyr Lys Phe Ala
    370                 375                 380

atc tca cag tca tcc acg ggc act gtt atg gga gct gtt atc atg gag   1200
Ile Ser Gln Ser Ser Thr Gly Thr Val Met Gly Ala Val Ile Met Glu
385                 390                 395                 400

ggc ttc tac gtt gtc ttt gat cgg gcc cga aaa cga att ggc ttt gct   1248
Gly Phe Tyr Val Val Phe Asp Arg Ala Arg Lys Arg Ile Gly Phe Ala
                405                 410                 415
                                            [              ]

gtc agc gct tgc cat gtg cac gat gag ttc agg acg gca gcg gtg gaa   1296
Val Ser Ala Cys His Val His Asp Glu Phe Arg Thr Ala Ala Val Glu
            420                 425                 430
[        Internal peptide sequence         ]
```

Fig. 5E

```
ggc cct ttt gtc acc ttg gac atg gaa gac tgt ggc tac aac att cca    1344
Gly Pro Phe Val Thr Leu Asp Met Glu Asp Cys Gly Tyr Asn Ile Pro
        435                 440                 445

cag aca gat gag tca acc ctc atg acc ata gcc tat gtc atg gct gcc    1392
Gln Thr Asp Glu Ser Thr Leu Met Thr Ile Ala Tyr Val Met Ala Ala
    450                 455                 460

                        [          Transmembrane          ]
atc tgc gcc ctc ttc atg ctg cca ctc tgc ctc atg gtg tgt cag tgg    1440
Ile Cys Ala Leu Phe Met Leu Pro Leu Cys Leu Met Val Cys Gln Trp
465                 470                 475                 480
[                        Transmembrane                        ]
cgc tgc ctc cgc tgc ctg cgc cag cag cat gat gac ttt gct gat gac    1488
Arg Cys Leu Arg Cys Leu Arg Gln Gln His Asp Asp Phe Ala Asp Asp
            485                 490                 495

atc tcc ctg ctg aag tga                                            1506
Ile Ser Leu Leu Lys
            500
```

```
 E  T  D  E  E  P  E  E  P  G  R  R  G  S  F  V  E  M  V  D  N
GARACNGAYGARGARCCNGARGARCCNGGNMGNMGNGGNWSNTTYGTNGARATGGTNGAYAAY  63
```

```
      3427-3430  →              ←  3431-3434
      5' primer set 1                3' primer set 1

3448-3451  →              ←  3452-3455
      5' primer set 2                3' primer set 2
```

↓ 1° HNC/primer set 1

(3428+3433)
54 bp product

↓ 1°HNC & IMR32/ primer set 2

72 bp product sequence:

```
      set2        3460
      [5']  ←  5' RACE primer
CCCGAAGAGCCCGGCCGGAGGGGCAGCTTTGTCGA  35
 P  E  E  P  G  R  R  G  S  F  V
                 ORF
          3'RACE primer    [3']
              3459          set 2
```

```
Human Impain Seq.                   M A Q A L P W L L L W M G A G V L P A H G T Q H G I R L P L R S G
pBS/MuImPain E17 #11 cons           X X X X X X X X X X X X X X X X X X X X X X X X X X X X X X X X X
pBS/MuImPain E17 #14 cons           - - - - - - - - - - - - - - - - - - - - - - - - - - - - - - - - -
pBS/MuImPain E17 Brain#17cons       X X X X X X X X X X X X X X X X X X X X X X X X X X X X X X X X X
pBS/MuImPain E17 Brain#15cons       - - - - - - - - - - - - - - - - - - - - - - - - - - - - - - - - -
pBS/MuImPain H#3 cons               - - - - - - - - - - - - - - - - - - - - - - - - - - - - - - - - -

Human Impain Seq.                   L G G A P L G L R L P R E T D E E P E E P G R R G S F V E M V D N
pBS/MuImPain E17 #11 cons           X X X X X X X X X X X X X X S I S L I E P G R R G S F V E M V N N
pBS/MuImPain E17 #14 cons           - - - - - - - - - - - - - - - K L D - E P G R R G S F V E M V D N
pBS/MuImPain E17 Brain#17cons       X X X X X X X X X X X X X X X X X X X X X X X X X X F V E M V D N
pBS/MuImPain E17 Brain#15cons       - - - - - - - - - - - - - - - - - - - - - - - - - - F V E M V D N
pBS/MuImPain H#3 cons               - - - - - - - - - - - - - I D K L D - E P G R R G S F V E M V D N

Human Impain Seq.                   L R G K S G Q G Y Y V E M T V G S P P Q T L N I L V D T G S S N F
pBS/MuImPain E17 #11 cons           L R G K S G Q G Y Y V E M T V G S P P Q T L N I L V D T G S S N F
pBS/MuImPain E17 #14 cons           L R G K S G Q G Y Y V E M T V G S P P Q T L N I L V D T G S S N F
pBS/MuImPain E17 Brain#17cons       L R G K S G Q G Y Y V E M T V G S P P Q T L N I L V D T G S S N F
pBS/MuImPain E17 Brain#15cons       L R G K S G Q G Y Y V E M T V G S P P Q T L N I L V D T G S S N F
pBS/MuImPain H#3 cons               L R G K S G Q G Y Y V E M T V G S P P Q T L N I L V D T G S S N F

Human Impain Seq.                   A V G A A P H P F L H R Y Y Q R Q L S S T Y R D L R K G V Y V P Y
pBS/MuImPain E17 #11 cons           A V G A A P H P F L H R Y Y Q R Q L S S T Y R D L R K G V Y V P Y
pBS/MuImPain E17 #14 cons           A V G A A P H P F L H R Y Y Q R Q L S S T Y R D L R K G V Y V P Y
pBS/MuImPain E17 Brain#17cons       A V G A A P H P F L H R Y Y Q R Q L S S T Y R D L R K G V Y V P Y
pBS/MuImPain E17 Brain#15cons       A V G A A P H P F L H R Y Y Q R Q L S S T Y R D L R K G V Y V P Y
pBS/MuImPain H#3 cons               A V G A A P H P F L H R Y Y Q R Q L S S T Y R D L R K G V Y V P Y
```

FIG. 10A

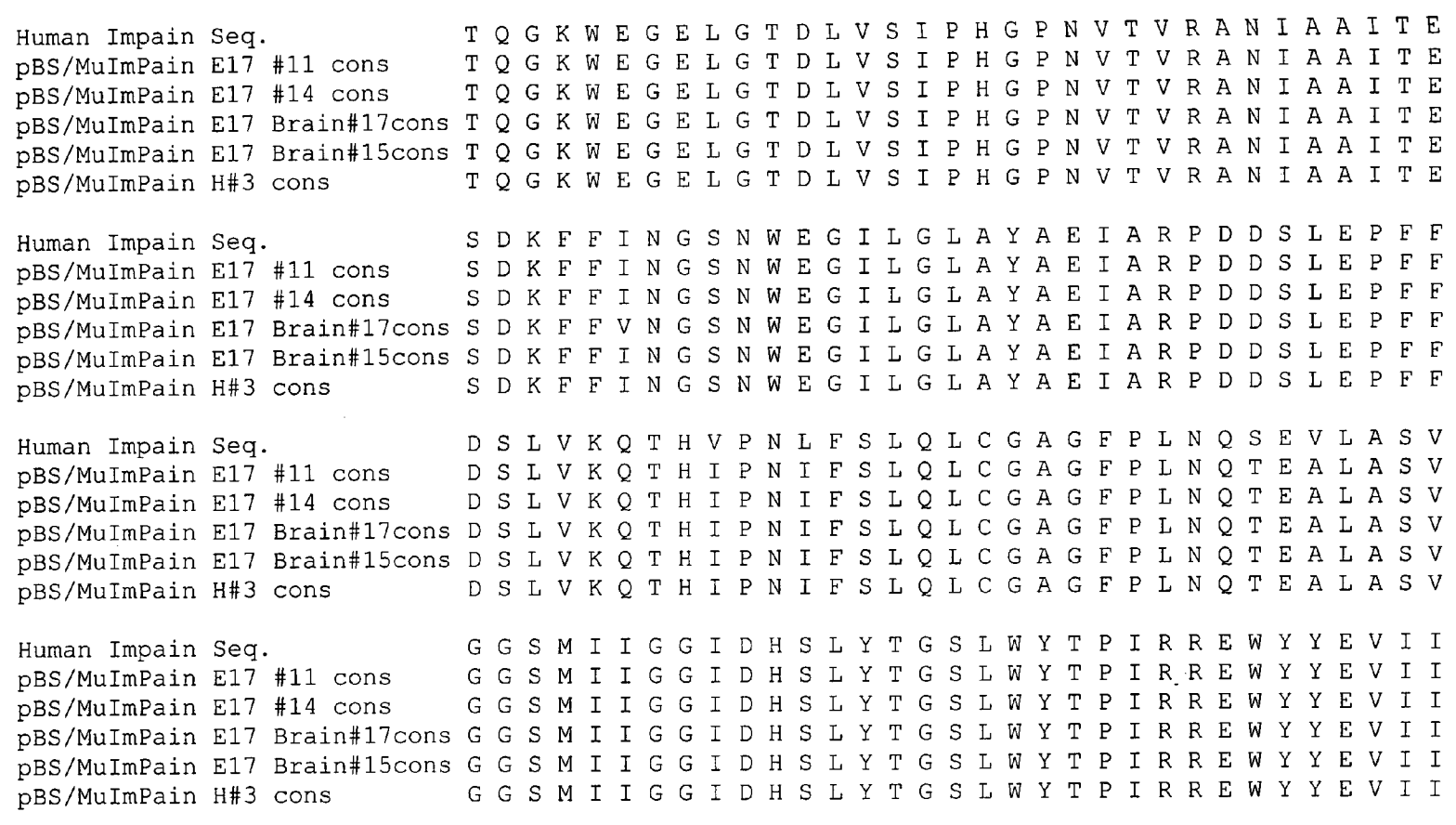

```
Human Impain Seq.               T Q G K W E G E L G T D L V S I P H G P N V T V R A N I A A I T E
pBS/MuImPain E17 #11 cons       T Q G K W E G E L G T D L V S I P H G P N V T V R A N I A A I T E
pBS/MuImPain E17 #14 cons       T Q G K W E G E L G T D L V S I P H G P N V T V R A N I A A I T E
pBS/MuImPain E17 Brain#17cons   T Q G K W E G E L G T D L V S I P H G P N V T V R A N I A A I T E
pBS/MuImPain E17 Brain#15cons   T Q G K W E G E L G T D L V S I P H G P N V T V R A N I A A I T E
pBS/MuImPain H#3 cons           T Q G K W E G E L G T D L V S I P H G P N V T V R A N I A A I T E

Human Impain Seq.               S D K F F I N G S N W E G I L G L A Y A E I A R P D D S L E P F F
pBS/MuImPain E17 #11 cons       S D K F F I N G S N W E G I L G L A Y A E I A R P D D S L E P F F
pBS/MuImPain E17 #14 cons       S D K F F I N G S N W E G I L G L A Y A E I A R P D D S L E P F F
pBS/MuImPain E17 Brain#17cons   S D K F F V N G S N W E G I L G L A Y A E I A R P D D S L E P F F
pBS/MuImPain E17 Brain#15cons   S D K F F I N G S N W E G I L G L A Y A E I A R P D D S L E P F F
pBS/MuImPain H#3 cons           S D K F F I N G S N W E G I L G L A Y A E I A R P D D S L E P F F

Human Impain Seq.               D S L V K Q T H V P N L F S L Q L C G A G F P L N Q S E V L A S V
pBS/MuImPain E17 #11 cons       D S L V K Q T H I P N I F S L Q L C G A G F P L N Q T E A L A S V
pBS/MuImPain E17 #14 cons       D S L V K Q T H I P N I F S L Q L C G A G F P L N Q T E A L A S V
pBS/MuImPain E17 Brain#17cons   D S L V K Q T H I P N I F S L Q L C G A G F P L N Q T E A L A S V
pBS/MuImPain E17 Brain#15cons   D S L V K Q T H I P N I F S L Q L C G A G F P L N Q T E A L A S V
pBS/MuImPain H#3 cons           D S L V K Q T H I P N I F S L Q L C G A G F P L N Q T E A L A S V

Human Impain Seq.               G G S M I I G G I D H S L Y T G S L W Y T P I R R E W Y Y E V I I
pBS/MuImPain E17 #11 cons       G G S M I I G G I D H S L Y T G S L W Y T P I R R E W Y Y E V I I
pBS/MuImPain E17 #14 cons       G G S M I I G G I D H S L Y T G S L W Y T P I R R E W Y Y E V I I
pBS/MuImPain E17 Brain#17cons   G G S M I I G G I D H S L Y T G S L W Y T P I R R E W Y Y E V I I
pBS/MuImPain E17 Brain#15cons   G G S M I I G G I D H S L Y T G S L W Y T P I R R E W Y Y E V I I
pBS/MuImPain H#3 cons           G G S M I I G G I D H S L Y T G S L W Y T P I R R E W Y Y E V I I
```

FIG. 10B

```
Human Impain Seq.              V R V E I N G Q D L K M D C K E Y N Y D K S I V D S G T T N L R L
pBS/MuImPain E17 #11 cons      V R V E I N G Q D L K M D C K E Y N Y D K S I V D S G T T N L R L
pBS/MuImPain E17 #14 cons      V R V E I N G Q D L K M D C K E Y N Y D K S I V D S G T T N L R L
pBS/MuImPain E17 Brain#17cons  V R V E I N G Q D L K M D C K E Y N Y D K S I V D S
pBS/MuImPain E17 Brain#15cons  V R V E I N G Q D L K M D C K E Y N Y D K S I V D S G T T N L R L
pBS/MuImPain H#3 cons          V R V E I N G Q D L K M D C K E Y N Y D K S I V D S G T T N L R L

Human Impain Seq.              P K K V F E A A V K S I K A A S S T E K F P D G F W L G E Q L V C
pBS/MuImPain E17 #11 cons      P K K V F E A A V K S I K A A S S T E K F P D G F W L G E Q L V C
pBS/MuImPain E17 #14 cons      P K K V F E A A V K S I K A A S S T E K F P D G F W L G E Q L V C
pBS/MuImPain E17 Brain#17cons
pBS/MuImPain E17 Brain#15cons  P K K V F E A A V K S I K A A S S T E K F P D G F W L G E Q L V C
pBS/MuImPain H#3 cons          P K K V F E A A V K S I K A A S S T E K F P D G F W L G E Q L V C

Human Impain Seq.              W Q A G T T P W N I F P V I S L Y L M G E V T N Q S F R I T I L P
pBS/MuImPain E17 #11 cons      W Q A G T T P W N I F P V I S L Y L M G E V T N Q S F R I T I L P
pBS/MuImPain E17 #14 cons      W Q A G T T P W N I F P V I S L Y L M G E V T N Q S F R I T I L P
pBS/MuImPain E17 Brain#17cons
pBS/MuImPain E17 Brain#15cons  W Q A G T T P W N I F P V I S L Y L M G E V T N Q S F R I T I L P
pBS/MuImPain H#3 cons          W Q A G T T P W N I F P V I S L Y L M G E V T N Q S F R I T I L P

Human Impain Seq.              Q Q Y L R P V E D V A T S Q D D C Y K F A I S Q S S T G T V M G A
pBS/MuImPain E17 #11 cons      Q Q Y L R P V E D V A T S Q D D C Y K F A V S Q S S T G T V M G A
pBS/MuImPain E17 #14 cons      Q Q Y L R P V E D V A T S Q D D C Y K F A V S Q S S T G T V M G A
pBS/MuImPain E17 Brain#17cons
pBS/MuImPain E17 Brain#15cons  Q Q Y L R P V E D V A T S Q D D C Y K F A V S Q S S T G T V M G A
pBS/MuImPain H#3 cons          Q Q Y L R P V E D V A T S Q D D C Y K F A V S Q S S T G T V M G A
```

FIG. 10C

```
Human Impain Seq.               V I M E G F Y V V F D R A R K R I G F A V S A C H V H D E F R T A
pBS/MuImPain E17 #11 cons       V I M E G F Y V V F D R A R K R I G F A V S A C H V H D E F R T A
pBS/MuImPain E17 #14 cons       V I M E G F Y V V F D R A R K R I G F A V S A C H V H D E F R T A
pBS/MuImPain E17 Brain#17cons
pBS/MuImPain E17 Brain#15cons   V I M E G F Y V V F D R A R K R I G F A V S A C H V H D E F R T A
pBS/MuImPain H#3 cons           V I M E G F Y V V F D R A R K R I G F A V S A C H V H D E F R T A

Human Impain Seq.               A V E G P F V T L D M E D C G Y N I P Q T D E S T L M T I A Y V M
pBS/MuImPain E17 #11 cons       A V E G P F V T A D M E D C G Y N N R I P A A R G I
pBS/MuImPain E17 #14 cons       A V E G P F V T A D M E D C G Y N N R I Q
pBS/MuImPain E17 Brain#17cons
pBS/MuImPain E17 Brain#15cons   A V E G P F V T A D
pBS/MuImPain H#3 cons           A V E G P F V T A D M E D   G Y N N R I P A A R G I H   F   S G R

Human Impain Seq.               A A I C A L F M L P L C L M V C Q W R C L R C L R Q Q H D D F A D
pBS/MuImPain E17 #11 cons
pBS/MuImPain E17 #14 cons
pBS/MuImPain E17 Brain#17cons
pBS/MuImPain E17 Brain#15cons
pBS/MuImPain H#3 cons           H R G G A P I R P I V S R I N

Human Impain Seq.               D I S L L K
pBS/MuImPain E17 #11 cons
pBS/MuImPain E17 #14 cons
pBS/MuImPain E17 Brain#17cons
pBS/MuImPain E17 Brain#15cons
pBS/MuImPain H#3 cons
```

```
ttctcatgtt tgacagctta tcatcgcaga tccgggcaac gttgttgcat tgctgcaggc 60

gcagaactgg taggtatgga agatccgatg tacgggccag atatacgcgt tgacattgat 120
     SpeI
tattgactag ttattaatag taatcaatta cggggtcatt agttcatagc ccatatatgg 180

agttccgcgt tacataactt acggtaaatg gcccgcctgg ctgaccgccc aacgaccccc 240

gcccattgac gtcaataatg acgtatgttc ccatagtaac gccaataggg actttccatt 300

gacgtcaatg ggtggactat ttacggtaaa ctgcccactt ggcagtacat caagtgtatc 360

atatgccaag tacgccccct attgacgtca atgacggtaa atggcccgcc tggcattatg 420

cccagtacat gaccttatgg gactttccta cttggcagta catctacgta ttagtcatcg 480

ctattaccat ggtgatgcgg ttttggcagt acatcaatgg gcgtggatag cggtttgact 540

cacggggatt tccaagtctc caccccattg acgtcaatgg gagtttgttt tggcaccaaa 600

atcaacggga ctttccaaaa tgtcgtaaca actccgcccc attgacgcaa atgggcggta 660

ggcgtgtacg gtgggaggtc tatataagca gagctctctg gctaactaga gaacccactg 720

cttactggct tatcgaaatt aatacgactc actataggga gacccaagct ctgttgggct 780
```

Figure 13B

```
cgcggttgag gacaaactct tcgcggtctt tccagtactc ttggatcgga aacccgtcgg 840

cctccgaacg gtactccgcc accgagggac ctgagcgagt ccgcatcgac cggatcggaa 900
                     splice donor
aacctctcga ctgttggggt gagtactccc tctcaaaagc gggcatgact tctgcgctaa 960

gattgtcagt ttccaaaaac gaggaggatt tgatattcac ctggcccgcg gtgatgcctt 1020

tgagggtggc cgcgtccatc tggtcagaaa agacaatctt tttgttgtca agcttgaggt 1080

gtggcaggct tgagatctgg ccatacactt gagtgacaat gacatccact ttgcctttct 1140
       splice   acceptor                SalI
ctccacaggt gtccactccc aggtccaact gcaggtcgac tctagacccg gggaattctg 1200

cagatatcca tcacactggc cgcactcgtc cccagcccgc ccgggagctg cgagccgcga 1260

gctggattat ggtggcctga gcagccaacg cagccgcagg agcccggagc ccttgcccct 1320

gcccgcgccg ccgcccgccg gggggaccag ggaagccgcc accggcccgc catgcccgcc 1380

cctcccagcc ccgccgggag cccgcgcccg ctgcccaggc tggccgccgc cgtgccgatg 1440

tagcgggctc cggatcccag cctctcccct gctcccgtgc tctgcggatc tcccctgacc 1500

gctctccaca gcccggaccc gggggctggc ccagggccct gcaggccctg gcgtcctgat 1560

gccccccaagc tccctctcct gagaagccac cagcaccacc cagacttggg ggcaggcgcc 1620
```

Figure 13C

```
agggacggac gtgggccagt gcgagcccag agggcccgaa ggccggggcc cacc atg    1677
                                                            Met
                                                              1

gcc caa gcc ctg ccc tgg ctc ctg ctg tgg atg ggc gcg gga gtg ctg    1725
Ala Gln Ala Leu Pro Trp Leu Leu Leu Trp Met Gly Ala Gly Val Leu
                 5                  10                  15

cct gcc cac ggc acc cag cac ggc atc cgg ctg ccc ctg cgc agc ggc    1773
Pro Ala His Gly Thr Gln His Gly Ile Arg Leu Pro Leu Arg Ser Gly
            20                  25                  30

ctg ggg ggc gcc ccc ctg ggg ctg cgg ctg ccc cgg gag acc gac gaa    1821
Leu Gly Gly Ala Pro Leu Gly Leu Arg Leu Pro Arg Glu Thr Asp Glu
     35                  40                  45

gag ccc gag gag ccc ggc cgg agg ggc agc ttt gtg gag atg gtg gac    1869
Glu Pro Glu Glu Pro Gly Arg Arg Gly Ser Phe Val Glu Met Val Asp
 50                  55                  60                  65

aac ctg agg ggc aag tcg ggg cag ggc tac tac gtg gag atg acc gtg    1917
Asn Leu Arg Gly Lys Ser Gly Gln Gly Tyr Tyr Val Glu Met Thr Val
                 70                  75                  80

ggc agc ccc ccg cag acg ctc aac atc ctg gtg gat aca ggc agc agt    1965
Gly Ser Pro Pro Gln Thr Leu Asn Ile Leu Val Asp Thr Gly Ser Ser
             85                  90                  95
```

Figure 13D

```
aac ttt gca gtg ggt gct gcc ccc cac ccc ttc ctg cat cgc tac tac   2013
Asn Phe Ala Val Gly Ala Ala Pro His Pro Phe Leu His Arg Tyr Tyr
        100                 105                 110
____________________________________________________________________
cag agg cag ctg tcc agc aca tac cgg gac ctc cgg aag ggt gtg tat   2061
Gln Arg Gln Leu Ser Ser Thr Tyr Arg Asp Leu Arg Lys Gly Val Tyr
    115                 120                 125
____________________________________________________________________
gtg ccc tac acc cag ggc aag tgg gaa ggg gag ctg ggc acc gac ctg   2109
Val Pro Tyr Thr Gln Gly Lys Trp Glu Gly Glu Leu Gly Thr Asp Leu
130                 135                 140                 145
____________________________________________________________________
gta agc atc ccc cat ggc ccc aac gtc act gtg cgt gcc aac att gct   2157
Val Ser Ile Pro His Gly Pro Asn Val Thr Val Arg Ala Asn Ile Ala
                150                 155                 160
____________________________________________________________________
gcc atc act gaa tca gac aag ttc ttc atc aac ggc tcc aac tgg gaa   2205
Ala Ile Thr Glu Ser Asp Lys Phe Phe Ile Asn Gly Ser Asn Trp Glu
            165                 170                 175
____________________________________________________________________
ggc atc ctg ggg ctg gcc tat gct gag att gcc agg cct gac gac tcc   2253
Gly Ile Leu Gly Leu Ala Tyr Ala Glu Ile Ala Arg Pro Asp Asp Ser
        180                 185                 190
____________________________________________________________________
ctg gag cct ttc ttt gac tct ctg gta aag cag acc cac gtt ccc aac   2301
Leu Glu Pro Phe Phe Asp Ser Leu Val Lys Gln Thr His Val Pro Asn
    195                 200                 205
____________________________________________________________________
```

Figure 13E

```
ctc ttc tcc ctg cag ctt tgt ggt gct ggc ttc ccc ctc aac cag tct   2349
Leu Phe Ser Leu Gln Leu Cys Gly Ala Gly Phe Pro Leu Asn Gln Ser
210                 215                 220                 225

gaa gtg ctg gcc tct gtc gga ggg agc atg atc att gga ggt atc gac   2397
Glu Val Leu Ala Ser Val Gly Gly Ser Met Ile Ile Gly Gly Ile Asp
                230                 235                 240

cac tcg ctg tac aca ggc agt ctc tgg tat aca ccc atc cgg cgg gag   2445
His Ser Leu Tyr Thr Gly Ser Leu Trp Tyr Thr Pro Ile Arg Arg Glu
            245                 250                 255

tgg tat tat gag gtc atc att gtg cgg gtg gag atc aat gga cag gat   2493
Trp Tyr Tyr Glu Val Ile Ile Val Arg Val Glu Ile Asn Gly Gln Asp
        260                 265                 270

ctg aaa atg gac tgc aag gag tac aac tat gac aag agc att gtg gac   2541
Leu Lys Met Asp Cys Lys Glu Tyr Asn Tyr Asp Lys Ser Ile Val Asp
    275                 280                 285

agt ggc acc acc aac ctt cgt ttg ccc aag aaa gtg ttt gaa gct gca   2589
Ser Gly Thr Thr Asn Leu Arg Leu Pro Lys Lys Val Phe Glu Ala Ala
290                 295                 300                 305

gtc aaa tcc atc aag gca gcc tcc tcc acg gag aag ttc cct gat ggt   2637
Val Lys Ser Ile Lys Ala Ala Ser Ser Thr Glu Lys Phe Pro Asp Gly
                310                 315                 320
```

Figure 13F

```
ttc tgg cta gga gag cag ctg gtg tgc tgg caa gca ggc acc acc cct   2685
Phe Trp Leu Gly Glu Gln Leu Val Cys Trp Gln Ala Gly Thr Thr Pro
            325                 330                 335

tgg aac att ttc cca gtc atc tca ctc tac cta atg ggt gag gtt acc   2733
Trp Asn Ile Phe Pro Val Ile Ser Leu Tyr Leu Met Gly Glu Val Thr
        340                 345                 350

aac cag tcc ttc cgc atc acc atc ctt ccg cag caa tac ctg cgg cca   2781
Asn Gln Ser Phe Arg Ile Thr Ile Leu Pro Gln Gln Tyr Leu Arg Pro
    355                 360                 365

gtg gaa gat gtg gcc acg tcc caa gac gac tgt tac aag ttt gcc atc   2829
Val Glu Asp Val Ala Thr Ser Gln Asp Asp Cys Tyr Lys Phe Ala Ile
370                 375                 380                 385

tca cag tca tcc acg ggc act gtt atg gga gct gtt atc atg gag ggc   2877
Ser Gln Ser Ser Thr Gly Thr Val Met Gly Ala Val Ile Met Glu Gly
                390                 395                 400

ttc tac gtt gtc ttt gat cgg gcc cga aaa cga att ggc ttt gct gtc   2925
Phe Tyr Val Val Phe Asp Arg Ala Arg Lys Arg Ile Gly Phe Ala Val
            405                 410                 415

agc gct tgc cat gtg cac gat gag ttc agg acg gca gcg gtg gaa ggc   2973
Ser Ala Cys His Val His Asp Glu Phe Arg Thr Ala Ala Val Glu Gly
        420                 425                 430
```

Figure 13G

```
cct ttt gtc acc ttg gac atg gaa gac tgt ggc tac aac att cca cag   3021
Pro Phe Val Thr Leu Asp Met Glu Asp Cys Gly Tyr Asn Ile Pro Gln
    435                 440                 445

aca gat gag tca acc ctc atg acc ata gcc tat gtc atg gct gcc atc   3069
Thr Asp Glu Ser Thr Leu Met Thr Ile Ala Tyr Val Met Ala Ala Ile
450                 455                 460                 465

tgc gcc ctc ttc atg ctg cca ctc tgc ctc atg gtg tgt cag tgg cgc   3117
Cys Ala Leu Phe Met Leu Pro Leu Cys Leu Met Val Cys Gln Trp Arg
                470                 475                 480

tgc ctc cgc tgc ctg cgc cag cag cat gat gac ttt gct gat gac atc   3165
Cys Leu Arg Cys Leu Arg Gln Gln His Asp Asp Phe Ala Asp Asp Ile
            485                 490                 495

tcc ctg ctg aag tga ggaggcccat gggcagaaga tagagattcc cctggaccac   3220
Ser Leu Leu Lys
        500

acctccgtgg ttcactttgg tcacaagtag gagacacaga tggcacctgt ggccagagca 3280

cctcaggacc ctccccaccc accaaatgcc tctgccttga tggagaagga aaaggctggc 3340

aaggtgggtt ccagggactg tacctgtagg aaacagaaaa gagaagaaag aagcactctg 3400

ctggcgggaa tactcttggt cacctcaaat ttaagtcggg aaattctgct gcttgaaact 3460
```

Figure 13H

```
tcagccctga acctttgtcc accattcctt taaattctcc aacccaaagt attcttcttt 3520

tcttagtttc agaagtactg gcatcacacg caggttacct tggcgtgtgt ccctgtggta 3580
                   HindIII
ccctggcaga gaagagacca agcttgtttc cctgctggcc aaagtcagta ggagaggatg 3640

cacagtttgc tatttgcttt agagacaggg actgtataaa caagcctaac attggtgcaa 3700

agattgcctc ttgaattaaa aaaaaaaact agattgacta tttatacaaa tgggggcggc 3760

tggaaagagg agaaggagag ggagtacaaa gacagggaat agtgggatca aagctaggaa 3820

aggcagaaac acaaccactc accagtccta gttttagacc tcatctccaa gatagcatcc 3880

catctcagaa gatgggtgtt gttttcaatg ttttcttttc tgtggttgca gcctgaccaa 3940

aagtgagatg ggaagggctt atctagccaa agagctcttt tttagctctc ttaaatgaag 4000

tgcccactaa gaagttccac ttaacacatg aatttctgcc atattaattt cattgtctct 4060

atctgaacca ccctttattc tacatatgat aggcagcact gaaatatcct aaccccctaa 4120

gctccaggtg ccctgtggga gagcaactgg actatagcag ggctgggctc tgtcttcctg 4180

gtcataggct cactctttcc cccaaatctt cctctggagc tttgcagcca aggtgctaaa 4240

aggaataggt aggagacctc ttctatctaa tccttaaaag cataatgttg aacattcatt 4300
```

Figure 13I caacagctga tgccctataa cccctgcctg gatttcttcc tattaggcta taagaagtag 4360
caagatcttt acataattca gagtggtttc attgccttcc taccctctct aatggcccct 4420
ccatttattt gactaaagca tcacacagtg gcactagcat tataccaaga gtatgagaaa 4480
tacagtgctt tatggctcta acattactgc cttcagtatc aaggctgcct ggagaaagga 4540
tggcagcctc agggcttcct tatgtcctcc accacaagag ctccttgatg aaggtcatct 4600
ttttccccta tcctgttctt cccctccccg ctcctaatgg tacgtgggta cccaggctgg 4660
ttcttgggct aggtagtggg gaccaagttc attacctccc tatcagttct agcatagtaa 4720
actacggtac cagtgttagt gggaagagct gggtttcct agtataccca ctgcatccta 4780
ctcctacctg gtcaacccgc tgcttccagg tatgggacct gctaagtgtg gaattacctg 4840
ataagggaga gggaaataca aggagggcct ctggtgttcc tggcctcagc cagctgccca 4900
caagccataa accaataaaa caagaatact gagtcagttt tttatctggg ttctcttcat 4960
tcccactgca cttggtgctg ctttggctga ctgggaacac cccataacta cagagtctga 5020
caggaagact ggagactgtc cacttctagc tcggaactta ctgtgtaaat aaactttcag 5080
aactgctacc atgaagtgaa aatgccacat tttgctttat aatttctacc catgttggga 5140

Figure 13J

```
aaaactggct ttttcccagc cctttccagg gcataaaact caaccccttc gatagcaagt 5200

cccatcagcc tattattttt ttaaagaaaa cttgcacttg tttttctttt tacagttact 5260

tccttcctgc cccaaaatta taaactctaa gtgtaaaaaa aagtcttaac aacagcttct 5320

tgcttgtaaa aatatgtatt atacatctgt atttttaaat tctgctcctg aaaaatgact 5380

gtcccattct ccactcactg catttggggc ctttcccatt ggtctgcatg tcttttatca 5440

ttgcaggcca gtggacagag ggagaaggga gaacaggggt cgccaacact tgtgttgctt 5500

tctgactgat cctgaacaag aaagagtaac actgaggcgc tcgctcccat gcacaactct 5560

ccaaaacact tatcctcctg caagagtggg ctttccgggt ctttactggg aagcagttaa 5620

gccccctcct caccccttcc ttttttcttt ctttactcct ttggcttcaa aggattttgg 5680

aaaagaaaca atatgcttta cactcatttt caatttctaa atttgcaggg gatactgaaa 5740

aatacggcag gtggcctaag gctgctgtaa agttgagggg agaggaaatc ttaagattac 5800

aagataaaaa acgaatcccc taaacaaaaa gaacaataga actggtcttc cattttgcca 5860

cctttcctgt tcatgacagc tactaacctg gagacagtaa catttcatta accaaagaaa 5920

gtgggtcacc tgacctctga agagctgagt actcaggcca ctccaatcac cctacaagat 5980
```

Figure 13K gccaaggagg tcccaggaag tccagctcct taaactgacg ctagtcaata aacctgggca 6040
agtgaggcaa gagaaatgag gaagaatcca tctgtgaggt gacaggcacg gatgaaagac 6100
aaagacggaa aagagtatca aaggcagaaa ggagatcatt tagttgggtc tgaaaggaaa 6160
agtntttgct atccgacatg tactgctagt wcctgtaagc attttaggtc ccagaatgga 6220
aaaaaaaatc aagctatngg ttatataata atgnnnnnnn nnnnnnnnnn nntcgagcat 6280
gcatctagag ggccctattc tatagtgtca cctaaatgct agagctcgct gatcagcctc 6340
gactgtgcct tctagttgcc agccatctgt tgtttgcccc tcccccgtgc cttccttgac 6400
cctggaaggt gccactccca ctgtcctttc ctaataaaat gaggaaattg catcgcattg 6460
tctgagtagg tgtcattcta ttctgggggg tggggtgggg caggacagca agggggagga 6520
ttgggaagac aatagcaggc atgctgggga tgcggtgggc tctatggctt ctgaggcgga 6580
aagaaccagc tggggctcta gggggtatcc ccacgcgccc tgtagcggcg cattaagcgc 6640
ggcgggtgtg gtggttacgc gcagcgtgac cgctacactt gccagcgccc tagcgcccgc 6700
tcctttcgct ttcttccctt cctttctcgc cacgttcgcc ggctttcccc gtcaagctct 6760
aaatcggggc atccctttag ggttccgatt tagtgcttta cggcacctcg accccaaaaa 6820

Figure 13L

```
acttgattag ggtgatggtt cacgtagtgg gccatcgccc tgatagacgg tttttcgccc 6880

tttgacgttg gagtccacgt tctttaatag tggactcttg ttccaaactg gaacaacact 6940

caaccctatc tcggtctatt cttttgattt ataagggatt ttggggattt cggcctattg 7000

gttaaaaaat gagctgattt aacaaaaatt taacgcgaat tctagagccc cgccgccgga 7060

cgaactaaac ctgactacgg catctctgcc ccttcttcgc ggggcagtgc atgtaatccc 7120

ttcagttggt tggtacaact tgccaactgg gccctgttcc acatgtgaca cggggggga 7180

ccaaacacaa aggggttctc tgactgtagt tgacatcctt ataaatggat gtgcacattt 7240

gccaacactg agtggctttc atcctggagc agactttgca gtctgtggac tgcaacacaa 7300

cattgccttt atgtgtaact cttggctgaa gctcttacac caatgctggg ggacatgtac 7360

ctcccagggg cccaggaaga ctacgggagg ctacaccaac gtcaatcaga ggggcctgtg 7420

tagctaccga taagcggacc ctcaagaggg cattagcaat agtgtttata aggccccctt 7480
HpaI
gttaacccta aacgggtagc atatgcttcc cgggtagtag tatatactat ccagactaac 7540

cctaattcaa tagcatatgt tacccaacgg gaagcatatg ctatcgaatt agggttagta 7600
                      EcoRV
aaagggtcct aaggaacagc gatatctccc accccatgag ctgtcacggt tttatttaca 7660
```

Figure 13M

```
tggggtcagg attccacgag ggtagtgaac cattttagtc acaagggcag tggctgaaga 7720

tcaaggagcg ggcagtgaac tctcctgaat cttcgcctgc ttcttcattc tccttcgttt 7780

agctaataga ataactgctg agttgtgaac agtaaggtgt atgtgaggtg ctcgaaaaca 7840

aggtttcagg tgacgccccc agaataaaat ttggacgggg ggttcagtgg tggcattgtg 7900
                                              SpeI
ctatgacacc aatataaccc tcacaaaccc cttgggcaat aaatactagt gtaggaatga 7960

aacattctga atatctttaa caatagaaat ccatggggtg gggacaagcc gtaaagactg 8020

gatgtccatc tcacacgaat ttatggctat gggcaacaca taatcctagt gcaatatgat 8080

actggggtta ttaagatgtg tcccaggcag ggaccaagac aggtgaacca tgttgttaca 8140

ctctatttgt aacaagggga aagagagtgg acgccgacag cagcggactc cactggttgt 8200

ctctaacacc cccgaaaatt aaacggggct ccacgccaat ggggcccata aacaaagaca 8260

agtggccact cttttttttg aaattgtgga gtgggggcac gcgtcagccc ccacacgccg 8320

ccctgcggtt ttggactgta aaataagggt gtaataactt ggctgattgt aaccccgcta 8380

accactgcgg tcaaaccact tgcccacaaa accactaatg gcaccccggg gaatacctgc 8440

ataagtaggt gggcgggcca agataggggc gcgattgctg cgatctggag gacaaattac 8500
```

Figure 13N

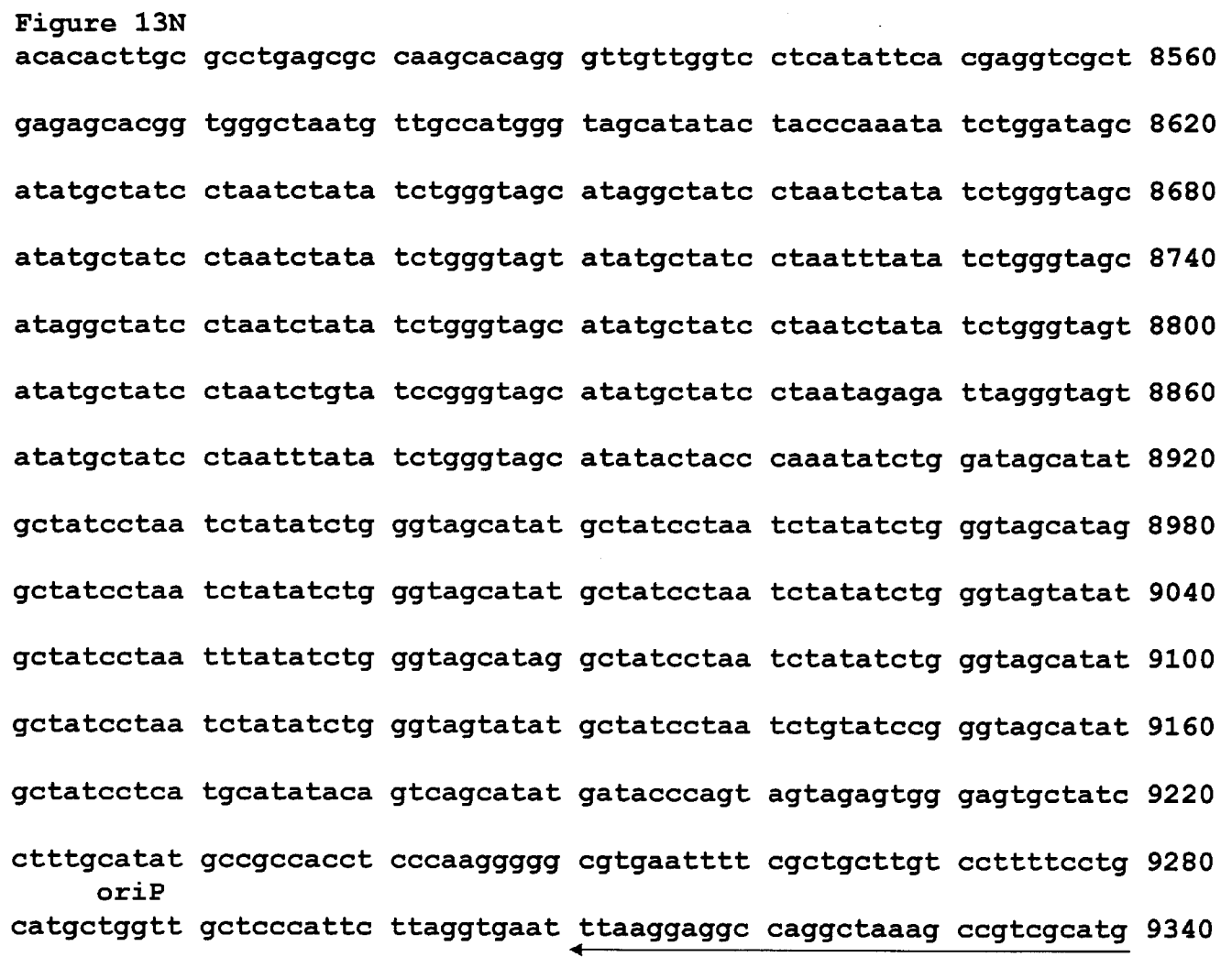

```
acacacttgc gcctgagcgc caagcacagg gttgttggtc ctcatattca cgaggtcgct 8560

gagagcacgg tgggctaatg ttgccatggg tagcatatac tacccaaata tctggatagc 8620

atatgctatc ctaatctata tctgggtagc ataggctatc ctaatctata tctgggtagc 8680

atatgctatc ctaatctata tctgggtagt atatgctatc ctaatttata tctgggtagc 8740

ataggctatc ctaatctata tctgggtagc atatgctatc ctaatctata tctgggtagt 8800

atatgctatc ctaatctgta tccgggtagc atatgctatc ctaatagaga ttagggtagt 8860

atatgctatc ctaatttata tctgggtagc atatactacc caaatatctg gatagcatat 8920

gctatcctaa tctatatctg ggtagcatat gctatcctaa tctatatctg ggtagcatag 8980

gctatcctaa tctatatctg ggtagcatat gctatcctaa tctatatctg ggtagtatat 9040

gctatcctaa tttatatctg ggtagcatag gctatcctaa tctatatctg ggtagcatat 9100

gctatcctaa tctatatctg ggtagtatat gctatcctaa tctgtatccg ggtagcatat 9160

gctatcctca tgcatataca gtcagcatat gatacccagt agtagagtgg gagtgctatc 9220

ctttgcatat gccgccacct cccaaggggg cgtgaatttt cgctgcttgt ccttttcctg 9280
     oriP
catgctggtt gctcccattc ttaggtgaat ttaaggaggc caggctaaag ccgtcgcatg 9340
```

Figure 130

```
tctgattgct caccaggtaa atgtcgctaa tgttttccaa cgcgagaagg tgttgagcgc 9400
ggagctgagt gacgtgacaa catgggtatg cccaattgcc ccatgttggg aggacgaaaa 9460
tggtgacaag acagatggcc agaaatacac caacagcacg catgatgtct actggggatt 9520
tattctttag tgcgggggaa tacacggctt ttaatacgat tgagggcgtc tcctaacaag 9580
ttacatcact cctgcccttc ctcaccctca tctccatcac ctccttcatc tccgtcatct 9640
ccgtcatcac cctccgcggc agccccttcc accataggtg gaaaccaggg aggcaaatct 9700
actccatcgt caaagctgca cacagtcacc ctgatattgc aggtaggagc gggctttgtc 9760
ataacaaggt ccttaatcgc atccttcaaa acctcagcaa atatatgagt ttgtaaaaag 9820
accatgaaat aacagacaat ggactccctt agcgggccag gttgtgggcc gggtccaggg 9880
gccattccaa aggggagacg actcaatggt gtaagacgac attgtggaat agcaagggca 9940
gttcctcgcc ttaggttgta aagggaggtc ttactacctc catatacgaa cacaccggcg 10000
acccaagttc cttcgtcggt agtcctttct acgtgactcc tagccaggag agctcttaaa 10060
ccttctgcaa tgttctcaaa tttcgggttg gaacctcctt gaccacgatg ctttccaaac 10120
caccctcctt ttttgcgcct gcctccatca ccctgacccc ggggtccagt gcttgggcct 10180
```

Figure 13P tctcctgggt catctgcggg gccctgctct atcgctcccg ggggcacgtc aggctcacca 10240
tctgggccac cttcttggtg gtattcaaaa taatcggctt cccctacagg gtggaaaaat 10300
ggccttctac ctggaggggg cctgcgcggt ggagacccgg atgatgatga ctgactactg 10360
ggactcctgg gcctcttttc tccacgtcca cgacctctcc ccctggctct ttcacgactt 10420 cccccccctgg ctctttcacg tcctctaccc cggcggcctc cactacctcc tcgaccccgg 10480
cctccactac ctcctcgacc ccggcctcca ctgcctcctc gaccccggcc tccacctcct 10540
gctcctgccc ctcctgctcc tgcccctcct cctgctcctg cccctcctgc ccctcctgct 10600
cctgcccctc ctgcccctcc tgctcctgcc cctcctgccc ctcctgctcc tgcccctcct 10660
gcccctcctc ctgctcctgc ccctcctgcc cctcctcctg ctcctgcccc tcctgcccct 10720
cctgctcctg cccctcctgc ccctcctgct cctgcccctc ctgcccctcc tgctcctgcc 10780
cctcctgctc ctgcccctcc tgctcctgcc cctcctgctc ctgcccctcc tgcccctcct 10840
gcccctcctc ctgctcctgc ccctcctgct cctgcccctc ctgcccctcc tgcccctcct 10900
gctcctgccc ctcctcctgc tcctgcccct cctgcccctc ctgcccctcc tcctgctcct 10960
gcccctcctg cccctcctcc tgctcctgcc cctcctcctg ctcctgcccc tcctgcccct 11020

Figure 13Q cctgcccctc ctcctgctcc tgcccctcct gcccctcctc ctgctcctgc ccctcctcct 11080
gctcctgccc ctcctgcccc tcctgcccct cctcctgctc ctgcccctcc tcctgctcct 11140
gcccctcctg cccctcctgc ccctcctgcc cctcctcctg ctcctgcccc tcctcctgct 11200
cctgcccctc ctgctcctgc ccctcccgct cctgctcctg ctcctgttcc accgtgggtc 11260
cctttgcagc caatgcaact tggacgtttt tggggtctcc ggacaccatc tctatgtctt 11320
ggccctgatc ctgagccgcc cggggctcct ggtcttccgc ctcctcgtcc tcgtcctctt 11380
ccccgtcctc gtccatggtt atcacccccct cttctttgag gtccactgcc gccggagcct 11440
tctggtccag atgtgtctcc cttctctcct aggccatttc caggtcctgt acctggcccc 11500
tcgtcagaca tgattcacac taaaagagat caatagacat ctttattaga cgacgctcag 11560
tgaatacagg gagtgcagac tcctgccccc tccaacagcc cccccaccct catccccttc 11620
atggtcgctg tcagacagat ccaggtctga aaattcccca tcctccgaac catcctcgtc 11680
ctcatcacca attactcgca gcccggaaaa ctcccgctga acatcctcaa gatttgcgtc 11740
ctgagcctca agccaggcct caaattcctc gtccccccttt ttgctggacg gtagggatgg 11800
ggattctcgg gacccctcct cttcctcttc aaggtcacca gacagagatg ctactggggc 11860

Figure 13R

```
                                              ClaI
aacggaagaa aagctgggtg cggcctgtga ggatcagctt atcgatgata agctgtcaaa 11920

catgagaatt cttgaagacg aaagggcctc gtgatacgcc tatttttata ggttaatgtc 11980

atgataataa tggtttctta gacgtcaggt ggcacttttc ggggaaatgt gcgcggaacc 12040

cctatttgtt tatttttcta aatacattca aatatgtatc cgctcatgag acaataaccc 12100

tgataaatgc ttcaataata ttgaaaaagg aagagtatga gtattcaaca tttccgtgtc 12160

gcccttattc ccttttttgc ggcattttgc cttcctgttt ttgctcaccc agaaacgctg 12220

gtgaaagtaa aagatgctga agatcagttg ggtgcacgag tgggttacat cgaactggat 12280

ctcaacagcg gtaagatcct tgagagtttt cgccccgaag aacgttttcc aatgatgagc 12340

acttttaaag ttctgctatg tggcgcggta ttatcccgtg ttgacgccgg gcaagagcaa 12400

ctcggtcgcc gcatacacta ttctcagaat gacttggttg agtactcacc agtcacagaa 12460

aagcatctta cggatggcat gacagtaaga gaattatgca gtgctgccat aaccatgagt 12520
                                   PvuI
gataacactg cggccaactt acttctgaca acgatcggag gaccgaagga gctaaccgct 12580

tttttgcaca acatggggga tcatgtaact cgccttgatc gttgggaacc ggagctgaat 12640

gaagccatac caaacgacga gcgtgacacc acgatgcctg cagcaatggc aacaacgttg 12700
```

Figure 13S

```
cgcaaactat taactggcga actacttact ctagcttccc ggcaacaatt aatagactgg 12760

atggaggcgg ataaagttgc aggaccactt ctgcgctcgg cccttccggc tggctggttt 12820

attgctgata aatctggagc cggtgagcgt gggtctcgcg gtatcattgc agcactgggg 12880

ccagatggta agccctcccg tatcgtagtt atctacacga cggggagtca ggcaactatg 12940

gatgaacgaa atagacagat cgctgagata ggtgcctcac tgattaagca ttggtaactg 13000

tcagaccaag tttactcata tatactttag attgatttaa aacttcattt ttaatttaaa 13060

aggatctagg tgaagatcct ttttgataat ctcatgacca aaatccctta acgtgagttt 13120

tcgttccact gagcgtcaga ccccgtagaa aagatcaaag gatcttcttg agatcctttt 13180

tttctgcgcg taatctgctg cttgcaaaca aaaaaaccac cgctaccagc ggtggtttgt 13240

ttgccggatc aagagctacc aactcttttt ccgaaggtaa ctggcttcag cagagcgcag 13300

ataccaaata ctgtccttct agtgtagccg tagttaggcc accacttcaa gaactctgta 13360

gcaccgccta catacctcgc tctgctaatc ctgttaccag tggctgctgc cagtggcgat 13420

aagtcgtgtc ttaccgggtt ggactcaaga cgatagttac cggataaggc gcagcggtcg 13480

ggctgaacgg ggggttcgtg cacacagccc agcttggagc gaacgaccta caccgaactg 13540
```

Figure 13T

```
agatacctac agcgtgagct atgagaaagc gccacgcttc ccgaagggag aaaggcggac 13600

aggtatccgg taagcggcag ggtcggaaca ggagagcgca cgagggagct tccaggggga 13660

aacgcctggt atctttatag tcctgtcggg tttcgccacc tctgacttga gcgtcgattt 13720

ttgtgatgct cgtcaggggg gcggagccta tggaaaaacg ccagcaacgc ggccttttta 13780

cggttcctgg ccttttgctg cgccgcgtgc ggctgctgga gatggcggac gcgatggata 13840

tgttctgcca agggttggtt tgcgcattca cagttctccg caagaattga ttggctccaa 13900

ttcttggagt ggtgaatccg ttagcgaggt gccgccggct tccattcagg tcgaggtggc 13960

ccggctccat gcaccgcgac gcaacgcggg gaggcagaca aggtataggg cggcgcctac 14020

aatccatgcc aacccgttcc atgtgctcgc cgaggcggca taaatcgccg tgacgatcag 14080

cggtccagtg atcgaagtta ggctggtaag agccgcgagc gatccttgaa gctgtccctg 14140

atggtcgtca tctacctgcc tggacagcat ggcctgcaac gcgggcatcc cgatgccgcc 14200
                                                      NruI
ggaagcgaga agaatcataa tggggaaggc catccagcct cgcgtcgcga acgccagcaa 14260

gacgtagccc agcgcgtcgg ccgccatgcc ctgcttcatc cccgtggccc gttgctcgcg 14320

tttgctggcg gtgtccccgg aagaaatata tttgcatgtc tttagttcta tgatgacaca 14380
```

Figure 13U

```
aaccccgccc agcgtcttgt cattggcgaa ttcgaacacg cagatgcagt cggggcggcg 14440

cggtcccagg tccacttcgc atattaaggt gacgcgtgtg gcctcgaaca ccgagcgacc 14500

ctgcagcgac ccgcttaaca gcgtcaacag cgtgccgcag atcccgggca atgagatatg 14560

aaaaagcctg aactcaccgc gacgtctgtc gagaagtttc tgatcgaaaa gttcgacagc 14620

gtctccgacc tgatgcagct ctcggagggc gaagaatctc gtgctttcag cttcgatgta 14680

ggagggcgtg gatatgtcct gcgggtaaat agctgcgccg atggtttcta caaagatcgt 14740

tagtgggatc ggcactttgc atcggccgcg ctccccgatt ccggaagtgc ttgacattgg 14800

ggaattcagc gagagcctga cctattgcat ctcccgccgt gcacagggtg tcacgttgca 14860

agacctgcct gaaaccgaac tgcccgctgt tctgcagccg gtcgcggagg ccatggatgc 14920
PvuI
gatcgctgcg gccgatctta gccagacgag cgggttcggc ccattcggac cgcaaggaat 14980

cggtcaatac actacatggc gtgatttcat atgcgcgatt gctgatcccc atgtgtatca 15040

ctggcaaact gtgatggacg acaccgtcag tgcgtccgtc gcgcaggctc tcgatgagct 15100

gatgctttgg gccgaggact gccccgaagt ccggcacctc gtgcacgcgg atttcggctc 15160

caacaatgtc ctgacggaca atggccgcat aacagcggtc attgactgga gcgaggcgat 15220
```

Figure 13V gttcggggat tcccaatacg aggtcgccaa catcttcttc tggaggccgt ggttggcggg 15280
tatggagcag cagacgcgct acttcgagcg gaggcatccg gagcttgcag gatcgccgcg 15340
gctccgggcg tatatgctcc gcattggtct tgaccaactc tatcagagct tggttgacgg 15400
caatttcgat gatgcagctt gggcgcaggg tcgatgcgac gcaatcgtcc gatccggagc 15460
cgggactgtc gggcgtacac aaatcgcccg cagaagcgcg gccgtctgga ccgatggctg 15520
tgtagaagta ctcgccgata gtggaaacgg gagatggggg aggctaactg aaacacggaa 15580
ggagacaata ccggaaggaa cccgcgctat gacggcaata aaaagacaga ataaaacgca 15640
cgggtgttgg gtcgtttgtt cataaacgcg gggttcggtc ccagggctgg cactctgtcg 15700
ataccccacc gagaccccat tggggccaat acgcccgcgt ttcttccttt tccccacccc 15760
accccccaag ttcgggtgaa ggcccagggc tcgcagccaa cgtcggggcg gcaggccctg 15820
ccatagccac tggccccgtg ggttagggac ggggtccccc atggggaatg gtttatggtt 15880
cgtgggggtt attattttgg gcgttgcgtg gggtctggtc cacgactgga ctgagcagac 15940
agacccatgg tttttggatg gcctgggcat ggaccgcatg tactggcgcg acacgaacac 16000
cgggcgtctg tggctgccaa acaccccga cccccaaaaa ccaccgcgcg gatttctggc 16060

Figure 13W

```
           SalI
gtgccaagct agtcgaccaa                                        16080
▸
```

β-SECRETASE ENZYME COMPOSITIONS AND METHODS

This application claims the benefit of U.S. Provisional Application No. 60/168,854, filed Dec. 2, 1999.

FIELD OF THE INVENTION

The invention relates to the discovery of various active forms of β-secretase, an enzyme that cleaves β-amyloid precursor protein (APP) at one of the two cleavage sites necessary to produce β-amyloid peptide (Aβ). The invention also relates to inhibitors of this enzyme, which are considered candidates or leads for therapeutic agents in the treatment of amyloidogenic diseases such as Alzheimer's disease. Further aspects of the present invention include screening methods, assays, and kits for discovering such therapeutic inhibitors, as well as diagnostic methods for determining whether an individual carries a mutant form of the enzyme.

BACKGROUND OF THE INVENTION

Alzheimer's disease is characterized by the presence of numerous amyloid plaques and neurofibrillatory tangles present in the brain, particularly in those regions of the brain involved in memory and cognition. β-amyloid peptide (Aβ) is a 39-43 amino acid peptide that is major component of amyloid plaques and is produced by cleavage of a large protein known as the amyloid precursor protein (APP) at a specific site(s) within the N-terminal region of the protein. Normal processing of APP involves cleavage of the protein at point 16-17 amino acids C-terminal to the N-terminus of the α-AP region, releasing a secreted ectodomain, α-sAPP, thus precluding production of β-AP. Cleavage by a putative β-secretase enzyme of APP between $Met^{671}$ and $Asp^{672}$ and subsequent processing at the C-terminal end of APP produces Aβ peptide which is highly implicated in Alzheimer's pathology (Seubert, et al., in Pharmacological Treatment of Alzheimer's disease, Wiley-Liss, Inc., pp. 345-366, 1997; Zhao, J., et al. J. Biol. Chem. 271: 31407-31411, 1996).

It is not clear whether β-secretase enzyme levels and/or activity are inherently higher in Alzheimer's patients than normal; however, it is clear that the cleavage product of this enzyme, Aβ peptide, is abnormally concentrated in amyloid plaques in the brain of these patients. Therefore, it is desirable to isolate, purify and characterize the enzyme responsible for the pathogenic cleavage of APP in order to help answer this and other questions surrounding the etiology of the disease. In particular, it is also desirable to utilize the isolated enzyme, or active fragments thereof, in methods for screening candidate drugs for ability to inhibit the activity of β-secretase in in vitro systems. Drugs exhibiting inhibitory effects on β-secretase activity are expected to be useful therapeutics in the treatment of Alzheimer's disease and other amyloidogenic disorders characterized by deposition of Aβ peptide containing fibrils.

U.S. Pat. No. 5,744,346 (Chrysler, et al.) describes the initial isolation and partial purification of β-secretase. The present invention provides a significant improvement in the purity of enzyme, by providing a purified β-secretase enzyme that is at least 200 fold purer. Such pure enzyme has utility in a number of applications, including crystallization for structure determination. The invention also provides the methods for producing recombinant forms of human and mouse β-secretase. It is a further discovery of the present invention that human β-secretase is a so-called "aspartyl" (or "aspartic") protease, which is inhibited by certain polypeptides having 5 to 14 amino acids including polypetpides containing the non-natural amino acid residue, statine, as well as inhibitors containing a hydroxyethylene as an isosteric replacement of a peptide amide bond.

Additionally U.S. Pat. No. 5,192,668 entitled "Synthesis of Protease Inhibitor," issued Mar. 9, 1993; U.S. Pat. No. 5,188,950 entitled "Method of Preparing HIV Protease Inhibitors," issued Feb. 23, 1993; U.S. Pat. No. 5,187,074 entitled "Method of Hydroxylation with ATCC 55086," issued Feb. 16, 1993; and U.S. Pat. No. 5,175,298 entitled "Dipeptide Hydroxy Ethylene Isostere Synthesis and Intermediate Therefor," issued Dec. 29, 1992, relate to the synthesis and use of hydroxyethylene isosteres as protease inhibitors and are hereby incorporated in their entirety with the same effect as if each were incorporated separately by reference.

SUMMARY OF THE INVENTION

This invention is directed to a purified β-secretase protein and in particular to a purified protein characterized by a specific activity of at least about $0.1\times10^5$ nM/h/μg protein in a C125-SW substrate assay.

This invention is further directed to a crystalline protein composition formed from a purified β-secretase protein, including a composition where the purified protein is characterized by an ability to bind to the β-secretase inhibitor substrate P10-P4'sta D→V which is at least equal to an ability exhibited by a protein having the amino acid sequence SEQ ID NO: 70 [46-419], when said proteins are tested for binding to said substrate under the same conditions. The invention also includes a crystalline protein composition containing a β-secretase substrate or inhibitor molecule.

Another aspect of the invention is directed to an isolated protein, comprising a polypeptide that (i) is fewer than about 480 amino acid residues in length, (ii) includes an amino acid sequence that is at least 90% identical to SEQ ID NO: 58 [46-452] including conservative substitutions thereof, and (iii) exhibits β-secretase activity, as evidenced by an ability to cleave MBP-C125sw.

Additionally, this invention has found that an isolated protein, comprising a polypeptide that (i) is fewer than about 480 amino acid residues in length, (ii) includes an amino acid sequence that is at least 90% identical to SEQ ID NO: 75 [63-423] including conservative substitutions thereof, and (iii) exhibits β-secretase activity, as evidenced by an ability to cleave MBP-C125sw is useful for structure activity inhibitor design.

The invention further includes an antibody which binds specifically to any of the protein compositions of claims 1-13 or 25-36 of U.S. provisional application 60/168,854, wherein said antibody further lacks significant immunoreactivity with a protein having the sequence SEQ ID NO: 2 [1-501].

Another aspect of the invention is directed to an isolated nucleic acid, comprising a sequence of nucleotides that encodes the β-secretase protein, or a complementary sequence of any of such nucleotides. Additionally, the invention includes an expression vector comprising such isolated nucleic acids operably linked to the nucleic acid with regulatory sequences effective for expression of the nucleic acid in a selected host cell. The host cells can be an eukaryotic cell, a bacterial cell, an insect cell or a yeast cell.

The invention is also directed to a method of screening for compounds that inhibit Aβ production, comprising contacting a β-secretase polypeptide with (i) a test compound and (ii) a β-secretase substrate, and selecting the test compound as capable of inhibiting Aβ production if said β-secretase polypeptide exhibits less β-secretase activity in the presence of said compound than in the absence of said compound. It further includes administering said test compound to a mammalian subject having Alzheimer's disease or Alzheimer's disease like pathology, and selecting said compound as a therapeutic agent candidate if, following such administration, said subject maintains or improves cognitive ability or said subject shows reduce plaque burden.

Another aspect of the invention includes the method of screening for compounds that inhibit Aβ production, comprising measuring binding of a β-secretase polypeptide with a β-secretase inhibitor compound in the presence of a test compound, and selecting the test compound as β-secretase active-site binding compound, if binding of the inhibitor in the presence of said test compound is less than binding of the inhibitor in the absence of said test compound.

Another aspect of the invention is a method of screening for drugs effective in the treatment of Alzheimer's disease or other cerebrovascular amyloidosis characterized by Aβ deposition, comprising administering to a mammalian subject which is characterized by overexpression and/or deposition of Aβ, a test compound selected for its ability to inhibit β-secretase activity of β-secretase protein, and selecting the compound as a potential therapeutic drug compound, if it reduces the amount of Aβ deposition in said subject or if it maintains or improves cognitive ability in said subject.

Another aspect of the invention is directed to a method of treating a patient afflicted with or having a predilection for Alzheimer's disease or other cerebrovascular amyloidosis, comprising blocking the enzymatic hydrolysis of APP to Aβ in the patient by administering to the patient a pharmaceutically effective dose of a compound effective to inhibit a β-secretase protein.

An additional aspect of the invention is a therapeutic drug for the treatment of Alzheimer's disease or other cerebrovascular amyloidosis characterized by deposition of Aβ peptide, wherein said drug is selected for its ability to inhibit the enzymatic activity of a β-secretase protein, including where the inhibition of enzymatic activity is evidenced by a $K_1$ of less than about 50 μM in a MBP-APP sw assay. Within this aspect are further included, peptide and peptide derivative molecules containing statine residues therein which are capable of binding and inhibiting beta-secretase at the P1-P1' of the enzyme active site, and also hydroxyethylene isosteric replacements at the P1-P1' active site.

Lastly, the invention is directed to method of diagnosing the presence of or a predilection for Alzheimer's disease in a patient, comprising measuring β-secretase enzymatic activity in a cell sample from said patient, and diagnosing the patient as having or having a predilection for Alzheimer's disease, if said level enzymatic activity level is significantly greater than a pre-determined control activity level.

These and other objects and features of the invention will become more fully apparent when the following detailed description of the invention is read in conjunction with the accompanying drawings.

BRIEF DESCRIPTION OF THE FIGURES

FIG. 1A shows the sequence of a polynucleotide (SEQ ID NO: 1) which encodes human β-secretase translation product shown in FIG. 2A.

FIG. 1B shows the polynucleotide of FIG. 1A, including putative 5'- and 3'-untranslated regions (SEQ ID NO: 44).

FIG. 2A shows the amino acid sequence of the predicted translation product of the open reading frame of the polynucleotide sequence shown in FIGS. 1A and 1B.

FIG. 2B shows the amino acid sequence of an active fragment of human β-secretase (SEQ ID NO: 43).

FIG. 3A shows the translation product that encodes an active fragment of human β-secretase, 452stop, (amino acids 1-452 with reference to SEQ ID NO: 2; SEQ ID NO: 59) including a FLAG-epitope tag (underlined; SEQ ID NO: 45) at the C-terminus.

FIG. 3B shows the amino acid sequence of a fragment of human β-secretase (amino acids 46-452 with reference to SEQ ID NO: 2; SEQ ID NO: 58) including a FLAG-epitope tag (underlined; SEQ ID NO: 39) at the C-terminus.

FIG. 4 shows the sequence of the inhibitor P10-P4'staD→V (SEQ ID NO: 72).

FIGS. 5A-5E show the full length amino acid sequence of β-secretase 1-501 (SEQ ID NO: 2), including the ORF which encodes it (SEQ ID NO: 1), with certain features indicated, such as "active-D" sites indicating the aspartic acid active catalytic sites, the transmembrane region commencing at position 453, as well as leader sequence (1-22; SEQ ID NO: 46) and putative pre-pro region (23-45; SEQ ID NO: 47) and where the polynucleotide region corresponding the proenzyme region (nt 135-1503) represents SEQ ID NO: 44.

FIGS. 10A-10D shows an alignment of the amino acid sequence of human β-secretase ("Human Inapain.seq")(SEQ ID NO:65) compared to various mouse constructs(SEQ ID NOS:81-84), with the lowest construct in each row ("pBS/mImpain H#3 cons") (SEQ ID NO:85) representing a consensus mouse sequence.

FIGS. 13A-13W show the nucleotide sequence of pCEK clone 27 (SEQ ID NO: 49), with the OFR indicated by the amino acid sequence SEQ ID NO: 2.

BRIEF DESCRIPTION OF THE SEQUENCES

Figure 6A:
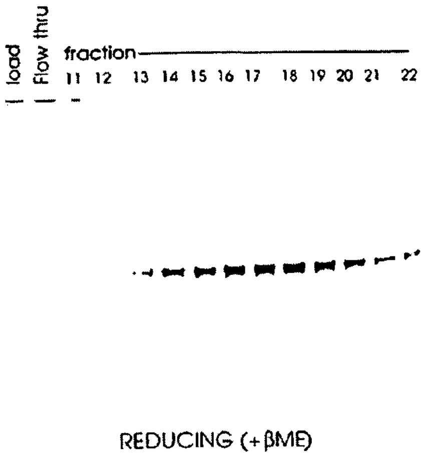
FIGS. 6A and 6B show images of silver-stained SDS-PAGE gels on which purified β-secretase containing fractions were run under reducing (6A) and non-reducing (6B) conditions.

SEQ ID NO: 1 is a nucleic acid sequence that encodes human β-secretase, including an active fragment, as exemplified herein.

SEQ ID NO: 2 is the predicted translation product of SEQ ID NO: 1.

SEQ ID NOS: 3-21 are degenerate oligonucleotide primers described in Example 1 herein, designed from regions of SEQ ID NO: 2.

SEQ ID NOS: 22-41 are additional oligonucleotide primers used in PCR cloning methods described herein.

SEQ ID NO: 42 is the polynucleotide sequence that encodes the active enzyme β-secretase shown as SEQ ID NO: 43.

SEQ ID NO: 43 is the sequence of an active enzyme portion of human β-secretase, the N-terminus of which corresponds to the N-terminus of the predominant form of the protein isolated from natural sources [46-501].

SEQ ID NO: 44 is a polynucleotide which encodes SEQ ID NO: 2, including a 5' untranslated region.

SEQ ID NO: 45 is the FLAG sequence used in conjunction with certain polynucleotides.

SEQ ID NO: 46 is the putative leader region of β-secretase [1-22].

SEQ ID NO: 47 is the putative pre-pro region of β-secretase [23-45].

SEQ ID NO: 48 is the sequence of the clone pCEK C1.27 (FIGS. 13A-E).

SEQ ID NO: 49 is a nucleotide sequence of a fragment of the gene which encodes human β-secretase.

SEQ ID NO: 50 is the predicted translation product of SEQ ID NO: 49.

SEQ ID NO: 51 is the predicted internal amino acid sequence of a portion of human β-secretase.

SEQ ID NOS: 52 and 53 are peptide substrates suitable for use in β-secretase assays used in the present invention.

SEQ ID NO: 54 is a peptide sequence cleavage site recognized by human β-secretase.

SEQ ID NO: 55 is amino acids 46-66 of SEQ ID NO: 2.

SEQ ID NO: 56 is an internal peptide just N-terminal to the transmembrane domain of β-secretase.

SEQ ID NO: 57 is β-secretase [1-419].

SEQ ID NO: 58 is β-secretase [46-452].

SEQ ID NO: 59 is β-secretase [1-452].

SEQ ID NO: 60 is β-secretase [1-420].

SEQ ID NO: 61 is EVM[hydroxyethylene]AEF.

SEQ ID NO: 62 is the amino acid sequence of the transmembrane domain of β-secretase (FIG. 5).

SEQ ID NO: 63 is P20-P4' of APPwt.

SEQ ID NO: 64 is P26-P1' of APPwt.

SEQ ID NO: 65 is mouse β-secretase (FIG. 10, lower sequence).

SEQ ID NO: 66 is β-secretase [22-501].

SEQ ID NO: 67 is β-secretase [58-501].

SEQ ID NO: 68 is β-secretase [58-452].

SEQ ID NO: 69 is β-secretase [63-501].

SEQ ID NO: 70 is β-secretase [63-452].

SEQ ID NO: 71 is β-secretase [46-419].

SEQ ID NO: 72 is P10-P4'staD→V.

SEQ ID NO: 73 is P4-P4'staD→V.

SEQ ID NO: 74 is β-secretase [22-452].

SEQ ID NO: 75 is β-secretase [63-423].

DETAILED DESCRIPTION OF THE INVENTION

I. Definitions

Unless otherwise indicated, all terms used herein have the same meaning as they would to one skilled in the art of the present invention. Practitioners are particularly directed to Sambrook, et al. (1989) Molecular Cloning: A Laboratory Manual (Second Edition), Cold Spring Harbor Press, Plainview, N.Y., and Ausubel, F. M., et al. (1998) Current Protocols in Molecular Biology, John Wiley & Sons, New York, N.Y., for definitions, terms of art and standard methods known in the art of molecular biology, particularly as it relates to the cloning protocols described herein. It is understood that this invention is not limited to the particular methodology, protocols, and reagents described, as these may be varied to produce the same result.

The terms "polynucleotide" and "nucleic acid" are used interchangeably herein and refer to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

The term "vector" refers to a polynucleotide having a nucleotide sequence that can assimilate new nucleic acids, and propagate those new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems.

The term "polypeptide" as used herein refers to a compound made up of a single chain of amino acid residues linked by peptide bonds. The term "protein" may be synonymous with the term "polypeptide" or may refer to a complex of two or more polypeptides.

The term "modified", when referring to a polypeptide of the invention, means a polypeptide which is modified either by natural processes, such as processing or other post-translational modifications, or by chemical modification techniques which are well known in the art. Among the numerous known modifications which may be present include, but are not limited to, acetylation, acylation, amidation, ADP-ribosylation, glycosylation, GPI anchor formation, covalent attachment of a lipid or lipid derivative, methylation, myristlyation, pegylation, prenylation, phosphorylation, ubiquitination, or any similar process.

The term "biologically active" used in conjunction with the term β-secretase refers to possession of a β-secretase enzyme activity, such as the ability to cleave β-amyloid precursor protein (APP) to produce β-amyloid peptide (Aβ).

The term "fragment," when referring to β-secretase of the invention, means a polypeptide which has an amino acid sequence which is the same as part of but not all of the amino acid sequence of full-length β-secretase polypeptide. In the context of the present invention, the full length β-secretase is generally identified as SEQ ID NO: 2, the ORF of the full-length nucleotide; however, according to a discovery of the invention, the naturally occurring active form is probably one or more N-terminal truncated versions, such as amino acids 46-501, 22-501, 58-501 or 63-501; other active forms are C-terminal truncated forms ending between about amino acids 450 and 452. The numbering system used throughout is based on the numbering of the sequence SEQ ID NO: 2.

An "active fragment" is a β-secretase fragment that retains at least one of the functions or activities of β-secretase, including but not limited to the β-secretase enzyme activity discussed above and/or ability to bind to the inhibitor substrate described herein as P10-P4'staD→V. Fragments contemplated include, but are not limited to, a β-secretase fragment which retains the ability to cleave β-amyloid precursor protein to produce β-amyloid peptide. Such a fragment preferably includes at least 350, and more preferably at least 400, contiguous amino acids or conservative substitutions thereof of β-secretase, as described herein. More preferably, the fragment includes active aspartyl acid residues in the structural proximities identified and defined by the primary polypeptide structure shown as SEQ ID NO: 2 and also denoted as "Active-D" sites herein.

A "conservative substitution" refers to the substitution of an amino acid in one class by an amino acid in the same class, where a class is defined by common physicochemical amino acid sidechain properties and high substitution frequencies in homologous proteins found in nature (as determined, e.g., by a standard Dayhoff frequency exchange matrix or BLOSUM matrix). Six general classes of amino acid sidechains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Optimal alignment" is defined as an alignment giving the highest percent identity score. Such alignment can be performed using a variety of commercially available sequence analysis programs, such as the local alignment program LALIGN using a ktup of 1, default parameters and the default PAM. A preferred alignment is the pairwise alignment using the CLUSTAL-W program in MacVector, operated with default parameters, including an open gap penalty of 10.0, an extended gap penalty of 0.1, and a BLOSUM30 similarity matrix.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two or more optimally aligned polypeptide sequences are identical. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence). Generally speaking, by way of example, when a protein composition is said to include 90% sequence identity to other proteins, this will not encompass longer proteins, such as proteins that have C- and/or N-terminal regions that make the resulting polypeptide 10% longer, unless the sequence identity is spread over such terminal region(s).

A first polypeptide region is said to "correspond" to a second polypeptide region when the regions are essentially co-extensive when the sequences containing the regions are aligned using a sequence alignment program, as above. Corresponding polypeptide regions typically contain a similar, if not identical, number of residues. It will be understood, however, that corresponding regions may contain insertions or deletions of residues with respect to one another, as well as some differences in their sequences.

A first polynucleotide region is said to "correspond" to a second polynucleotide region when the regions are essentially co-extensive when the sequences containing the regions are aligned using a sequence alignment program, as above. Corresponding polynucleotide regions typically contain a similar, if not identical, number of residues. It will be understood, however, that corresponding regions may contain insertions or deletions of bases with respect to one another, as well as some differences in their sequences.

The term "sequence identity" means nucleic acid or amino acid sequence identity in two or more aligned sequences, aligned as defined above.

"Sequence similarity" between two polypeptides is determined by comparing the amino acid sequence and its conserved amino acid substitutes of one polypeptide to the sequence of a second polypeptide. Thus, 80% protein sequence similarity means that 80% of the amino acid residues in two or more aligned protein sequences are conserved amino acid residues, i.e. are conservative substitutions.

"Hybridization" includes any process by which a strand of a nucleic acid joins with a complementary nucleic acid strand through base pairing. Thus, strictly speaking, the term refers to the ability of the complement of the target sequence to bind to the test sequence, or vice-versa.

"Hybridization conditions" are based in part on the melting temperature (Tm) of the nucleic acid binding complex or probe and are typically classified by degree of "stringency" of the conditions under which hybridization is measured. The specific conditions that define various degrees of stringency (i.e., high, medium, low) depend on the nature of the polynucleotide to which hybridization is desired, particularly its percent GC content, and can be determined empirically according to methods known in the art. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

The term "gene" as used herein means the segment of DNA involved in producing a polypeptide chain; it may include regions preceding and following the coding region, e.g. 5' untranslated (5' UTR) or "leader" sequences and 3' UTR or "trailer" sequences, as well as intervening sequences (introns) between individual coding segments (exons).

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such isolated polynucleotides could be part of a vector and/or such polynucleotides or polypeptides could be part of a composition, such as a recombinantly produced cell (heterologous cell) expressing the polypeptide, and still be isolated in that such vector or composition is not part of its natural environment.

An "isolated polynucleotide having a sequence which encodes β-secretase" is a polynucleotide that contains the coding sequence of β-secretase, or an active fragment thereof, (i) in isolation, (ii) in combination with additional coding sequences, such as fusion protein or signal peptide, in which the β-secretase coding sequence is the dominant coding sequence, (iii) in combination with non-coding sequences, such as introns and control elements, such as promoter and terminator elements or 5' and/or 3' untranslated regions, effective for expression of the coding sequence in a suitable host, and/or (iv) in a vector or host environment in which the β-secretase coding sequence is a heterologous gene.

The terms "heterologous DNA," "heterologous RNA," "heterologous nucleic acid," and "heterologous polynucleotide" refer to nucleotides that are not endogenous to the cell or part of the genome in which they are present; generally such nucleotides have been added to the cell, by transfection, microinjection, electroporation, or the like. Such nucleotides generally include at least one coding sequence, but this coding sequence need not be expressed.

The term "heterologous cell" refers to a recombinantly produced cell that contains at least one heterologous DNA molecule.

A "recombinant protein" is a protein isolated, purified, or identified by virtue of expression in a heterologous cell, said cell having been transduced or transfected, either transiently or stably, with a recombinant expression vector engineered to drive expression of the protein in the host cell.

The term "expression" means that a protein is produced by a cell, usually as a result of transfection of the cell with a heterologous nucleic acid.

"Co-expression" is a process by which two or more proteins or RNA species of interest are expressed in a single cell. Co-expression of the two or more proteins is typically achieved by transfection of the cell with one or more recombinant expression vectors(s) that carry coding sequences for the proteins. In the context of the present invention, a cell can be said to "co-express" two proteins, if only one of the proteins is heterologous to the cell.

The term "expression vector" refers to vectors that have the ability to incorporate and express heterologous DNA fragments in a foreign cell. Many prokaryotic and eukaryotic expression vectors are commercially available. Selection of appropriate expression vectors is within the knowledge of those having skill in the art.

The terms "purified" or "substantially purified" refer to molecules, either polynucleotides or polypeptides, that are removed from their natural environment, isolated or separated, and are at least 90% and more preferably at least 95-99% free from other components with which they are naturally associated.

The term "crystallized protein" means a protein that has co-precipitated out of solution in pure crystals consisting only of the crystal, but possibly including other components that are tightly bound to the protein.

A "variant" polynucleotide sequence may encode a "variant" amino acid sequence that is altered by one or more amino acids from the reference polypeptide sequence. The variant polynucleotide sequence may encode a variant amino acid sequence, which contains "conservative" substitutions, wherein the substituted amino acid has structural or chemical properties similar to the amino acid, which it replaces. In addition, or alternatively, the variant polynucleotide sequence may encode a variant amino acid sequence, which contains "non-conservative" substitutions, wherein the substituted amino acid has dissimilar structural or chemical properties to the amino acid, which it replaces. Variant polynucleotides may also encode variant amino acid sequences, which contain amino acid insertions or deletions, or both. Furthermore, a variant polynucleotide may encode the same polypeptide as the reference polynucleotide sequence but, due to the degeneracy of the genetic code, has a polynucleotide sequence that is altered by one or more bases from the reference polynucleotide sequence.

An "allelic variant" is an alternate form of a polynucleotide sequence, which may have a substitution, deletion or addition of one or more nucleotides that does not substantially alter the function of the encoded polypeptide.

"Alternative splicing" is a process whereby multiple polypeptide isoforms are generated from a single gene, and involves the splicing together of nonconsecutive exons during the processing of some, but not all, transcripts of the gene. Thus, a particular exon may be connected to any one of several alternative exons to form messenger RNAs. The alternatively-spliced mRNAs produce polypeptides ("splice variants") in which some parts are common while other parts are different.

"Splice variants" of β-secretase, when referred to in the context of an mRNA transcript, are mRNAs produced by alternative splicing of coding regions, i.e., exons, from the β-secretase gene.

"Splice variants" of β-secretase, when referred to in the context of the protein itself, are β-secretase translation products that are encoded by alternatively-spliced β-secretase mRNA transcripts.

A "mutant" amino acid or polynucleotide sequence is a variant amino acid sequence, or a variant polynucleotide sequence, which encodes a variant amino acid sequence that has significantly altered biological activity from that of the naturally occurring protein.

A "substitution" results from the replacement of one or more nucleotides or amino acids by different nucleotides or amino acids, respectively.

The term "modulate" as used herein refers to the change in activity of the polypeptide of the invention. Modulation may relate to an increase or a decrease in biological activity, binding characteristics, or any other biological, functional, or immunological property of the molecule.

The terms "antagonist" and "inhibitor" are used interchangeably herein and refer to a molecule which, when bound to the polypeptide of the present invention, modulates the activity of enzyme by blocking, decreasing, or shortening the duration of the biological activity. Competitive inhibition of an enzyme occurs when the inhibitor molecule can combine with the free enzyme in such a way that it competes with the normal substrate for binding at the active site. The inhibitor molecule is not changed by the enzyme, but rather remains in the enzyme active or catalytic site until it dissociates from the complex. Thus it is apparent that one hallmark of a good inhibitor is its binding affinity. Higher affinities allow the inhibitor to compete more effectively with the substrate for binding to the enzyme active site. An antagonist as used herein may also be referred to as a "β-secretase inhibitor" or "β-secretase blocker." Antagonists may themselves be polypeptides, nucleic acids, carbohydrates, lipids, small molecules (less than 1000 kD), or derivatives thereof, or any other ligand which binds to and modulates the activity of the enzyme.

III. β-Secretase Compositions

The present invention provides an isolated, active human β-secretase enzyme, which is further characterized as an aspartyl (aspartic) protease or proteinase, optionally, in purified form. As defined more fully in the sections that follow, β-secretase exhibits a proteolytic activity that is involved in the generation of β-amyloid peptide from β-amyloid precursor protein (APP), such as is described in U.S. Pat. No.

5,744,346, incorporated herein by reference. According to an important feature of the present invention, a human form of β-secretase has been isolated, and its naturally occurring form has been characterized, purified and sequenced. According to another aspect of the invention, nucleotide sequences encoding the enzyme have been identified. In addition, the enzyme has been further modified for expression in altered forms, such as truncated forms, which have similar protease activity to the naturally occurring or full length recombinant enzyme. Using the information provided herein, practitioners can isolate DNA encoding active forms of the protein from available sources and can express the protein recombinantly in a convenient expression system. Alternatively and in addition, practitioners can purify the enzyme from natural or recombinant sources and use it in purified form to further characterize its structure and function. According to a further feature of the invention, polynucleotides and proteins of the invention are particularly useful in a variety of screening assay formats, including cell-based screening for drugs that inhibit the enzyme. Examples of uses of such assays, as well as additional utilities for the compositions are provided in Section IV, below.

β-secretase is of particular interest due to its activity and involvement in generating fibril peptide components that are the major components of amyloid plaques in the central nervous system (CNS), such as are seen in Alzheimer's disease, Down's syndrome and other CNS disorders.

A. Isolation of Polynucleotides Encoding Human β-Secretase

Polynucleotides encoding human β-secretase were obtained by PCR cloning and hybridization techniques as detailed in Examples 1-3 and described below. FIG. 1A shows the sequence of a polynucleotide (SEQ ID NO: 1) which encodes human β-secretase. Polynucleotides encoding human β-secretase are conveniently isolated from any of a number of human tissues, preferably tissues of neuronal origin, including but not limited to neuronal cell lines such as the commercially available human neuroblastoma cell line IMR-32 available from the American Type Culture Collection (Manassas, Va.; ATTC CCL 127) and human fetal brain, such as a human fetal brain cDNA library available from OriGene Technologies, Inc. (Rockville, Md.).

Figure 9:
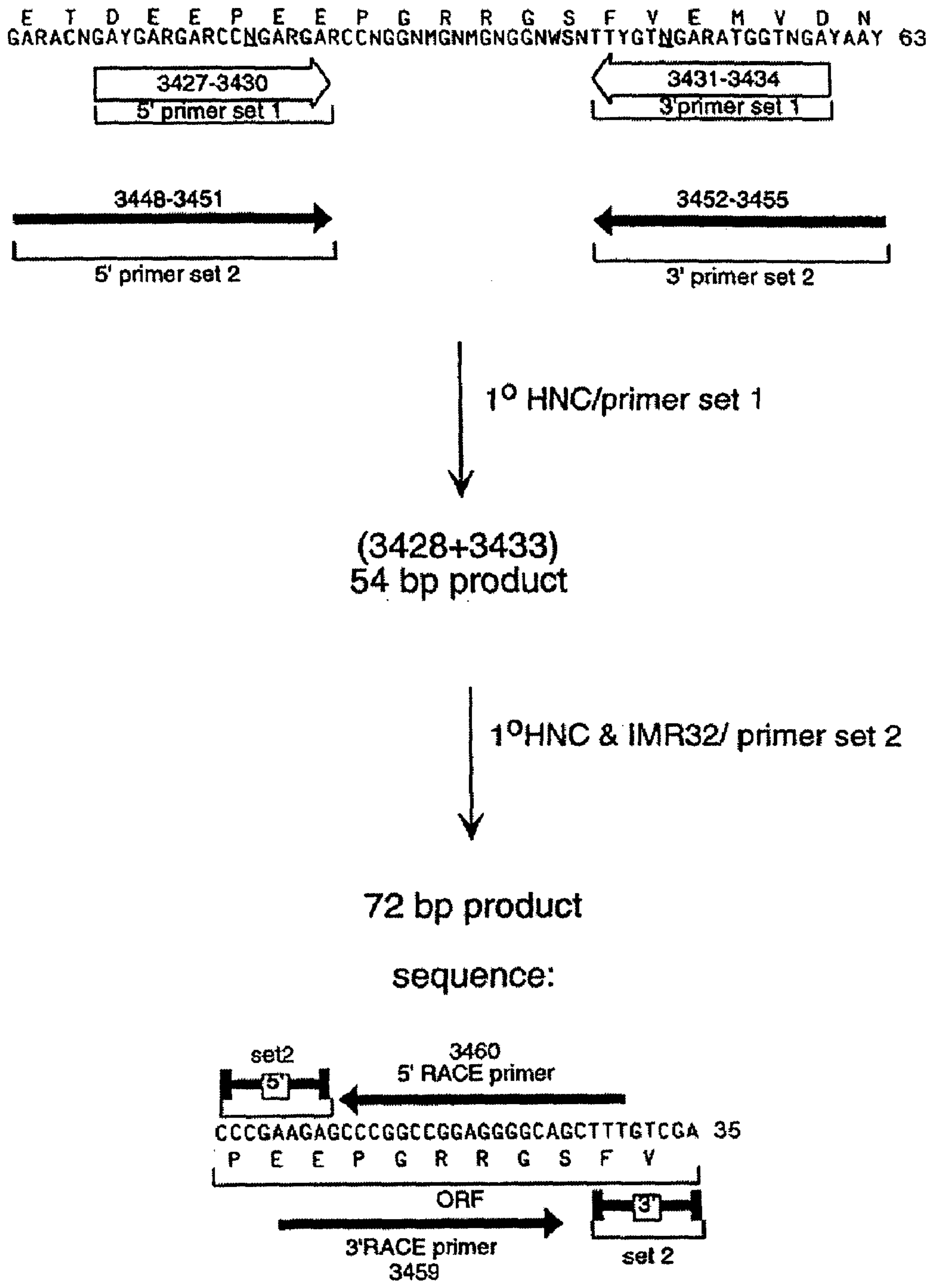
FIG. 9 shows a scheme in which primers derived from the N-terminus of purified naturally occurring β-secretase were used to PCR-clone additional portions of the molecule.

Briefly, human β-secretase coding regions were isolated by methods well known in the art, using hybridization probes derived from the coding sequence provided as SEQ ID NO: 1. Such probes can be designed and made by methods well known in the art. Exemplary probes, including degenerate probes, are described in Example 1. Alternatively, a cDNA library is screened by PCR, using, for example, the primers and conditions described in Example 2 herein. Such methods are discussed in more detail in Part B, below.

cDNA libraries were also screened using a 3'-RACE (Rapid Amplification of cDNA Ends) protocol according to methods well known in the art (White, B. A., ed., PCR Cloning Protocols; Humana Press, Totowa, N.J., 1997; FIG. 9). Here primers derived from the 5' portion of SEQ ID NO: 1 are added to partial cDNA substrate clone found by screening a fetal brain cDNA library described above. A representative 3'RACE reaction used in determining the longer sequence is detailed in Example 3 and is described in more detail in Part B, below.

Human β-secretase, as well as additional members of the neuronal aspartyl protease family described herein may be identified by the use of random degenerate primers designed in accordance with any portion of the polypeptide sequence shown as SEQ ID NO: 2. For example, in experiments carried out in support of the present invention, and detailed in Example 1 herein, eight degenerate primer pools, each 8-fold degenerate, were designed based on a unique 22 amino acid peptide region selected from SEQ ID: 2. Such techniques can be used to identify further similar sequences from other species and/or representing other members of this protease family.

Preparation of Polynucleotides

The polynucleotides described herein may be obtained by screening cDNA libraries using oligonucleotide probes, which can hybridize to and/or PCR-amplify polynucleotides that encode human β-secretase, as disclosed above. cDNA libraries prepared from a variety of tissues are commercially available, and procedures for screening and isolating cDNA clones are well known to those of skill in the art. Genomic libraries can likewise be screened to obtain genomic sequences including regulatory regions and introns. Such techniques are described in, for example, Sambrook et al. (1989) Molecular Cloning: A Laboratory Manual (2nd Edition), Cold Spring Harbor Press, Plainview, N.Y. and Ausubel, F M et al. (1998) Current Protocols in Molecular Biology, John Wiley & Sons, New York, N.Y.

The polynucleotides may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the MARATHON RACE kit (Cat. # K1802-1; Clontech, Palo Alto, Calif.).

Alternatively, the technique of "restriction-site" PCR (Gobinda et al. (1993) PCR Methods Applic. 2:318-22), which uses universal primers to retrieve flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al. (1988) Nucleic Acids Res 16:8186). The primers may be designed using OLIGO(R) 4.06 Primer Analysis Software (1992; National Biosciences Inc, Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Capture PCR (Lagerstrom M et al. (1991) PCR Methods Applic 1:111-19) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, J D et al. (1991; Nucleic Acids Res 19:3055-60). Additionally, one can use PCR, nested primers and PromoterFinder™ libraries to "walk in" genomic DNA (Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

The polynucleotides and oligonucleotides of the invention can also be prepared by solid-phase methods, according to known synthetic methods. Typically, fragments of up to about 100 bases are individually synthesized, then joined to form continuous sequences up to several hundred bases.

B. Isolation of β-Secretase

The amino acid sequence for the full-length human β-secretase translation product is shown as SEQ ID NO: 2 in FIG. 2A. This sequence was deduced from the nucleotide sequence information described in the previous section in conjunction with the methods described below. Comparison of this sequence with sequences determined from the biologically active form of the enzyme purified from natural sources, as described in Part 4, below, indicate that it is likely that the active form of the enzyme is represented by sequence shown in FIG. 2B (SEQ ID NO: 43), in which the first 45 amino acids of the open-reading frame deduced sequence have been removed. This suggests that the enzyme may be post-translationally modified by proteolytic activity, which may be autocatalytic in nature. Further analysis, illustrated by the schematics shown in FIG. 5 herein, indicates that the enzyme contains a hydrophobic, putative transmembrane region near its C-terminus. As described below, a further discovery of the present invention is that the enzyme can be truncated prior to this transmembrane region and still retain β-secretase activity.

1. Purification of β-Secretase from Natural and Recombinant Sources

According to an important feature of the present invention, β-secretase has now been purified from natural and recombinant sources. Co-owned U.S. Pat. No. 5,744,346, incorporated herein by reference, describes isolation of β-secretase in a single peak having an apparent molecular weight of 260-300,000 by gel exclusion chromatography. It is a discovery of the present invention that the enzyme can be further purified by affinity column chromatography. The methods revealed herein have been used on preparations from brain tissue as well as on preparations from 293 and recombinant cells; accordingly, these methods are believed to be generally applicable over a variety of tissue sources. The practitioner will realize that certain of the preparation steps, particularly the initial steps, may require modification to accommodate a particular tissue source and will adapt such procedures according to methods known in the art.

Methods for purifying β-secretase from human brain as well as from cells are detailed in Example 5. Briefly, cell membranes or brain tissue are homogenized, fractionated, and subjected to various types of column chromatographic matrices, including wheat germ agglutinin-agarose (WGA), anion exchange chromatography and size exclusion. Activity of fractions can be measured using any appropriate assay for β-secretase activity, such as the MBP-C125 cleavage assay detailed in Example 4. Fractions containing β-secretase activity elute from this column in a peak elution volume corresponding to a size of about 260-300 kilodaltons.

The foregoing purification scheme, which yields approximately 1.500-fold purification from is similar to that described in detail in U.S. Pat. No. 5,744,346, incorporated herein by reference. In accordance with the present invention, further purification can be achieved by applying the cation exchange flow-through material to an affinity column that employs as its affinity matrix a specific inhibitor of β-secretase, termed "P1-P4'staD→V" (FIG. 5). This inhibitor, and methods for making a Sepharose affinity column, which incorporates it, are described in Example 7.

Figure 6B:
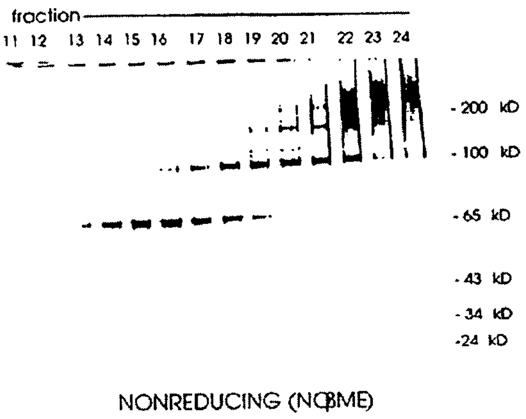

After washing the column, β-secretase and a limited number of contaminating proteins were eluted with pH 9.5 borate buffer. The eluate was then fractionated by anion exchange HPLC, using a Mini-Q column. Fractions containing the activity peak were pooled to give the final β-secretase preparation. Results of an exemplary run using this purification scheme are summarized in Table 1. FIG. 6A shows a picture of a silver-stained SDS PAGE gel run under reducing conditions, in which β-secretase runs as a 70 kilodalton band. The same fractions run under non-reducing conditions (FIG. 6B) provide evidence for disulfide cross-linked oligomers which run in the high molecular weight regions (approx. 260-300 kilodaltons) previously described. When the anion exchange pool fractions 18-21 (see FIG. 6B) were treated with dithiothreitol (DTT) and re-chromatographed on a Mini Q column, then subjected to SDS-PAGE under non-reducing conditions, a single band running at about 70 kilodaltons was observed. Surprisingly, the purity of this preparation is at least about 200 fold higher than the previously purified material, described in the '346 patent.

TABLE 1

Preparation of β-secretase from Human Brain

| | Total Activity[a] nM/h | Specific Activity[b] nM/h/mg prot. | % Yield | Purification (fold) |
|---|---|---|---|---|
| Brain Extract | 19,311,150 | 4,696 | 100 | 1 |
| WGA Eluate | 21,189,600 | 81,434 | 110 | 17 |
| Affinity Eluate | 11,175,000 | 257,500,000 | 53 | 54,837 |
| Anion Exchange Pool | 3,267,685 | 1,485,311,591 | 17 | 316,309 |

[a]Activity in MBP-C125sw assay $$^{b}\text{Specific Activity} = \frac{\text{(Product conc. nM)(Dilution factor)}}{\text{(Enzyme sol. vol)(Incub. time h)}}$$

(Enzyme conc. mg/vol)

Figure 7:
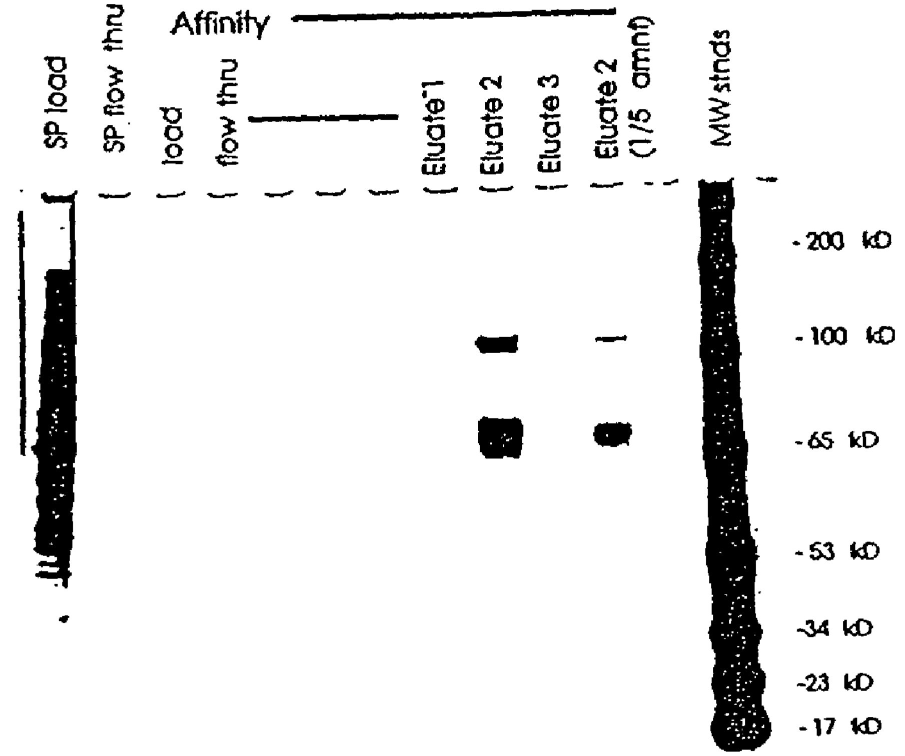
FIG. 7 shows a silver-stained SDS-PAGE of β-secretase purified from heterologous 293T cells expressing the recombinant enzyme.
Figure 8:
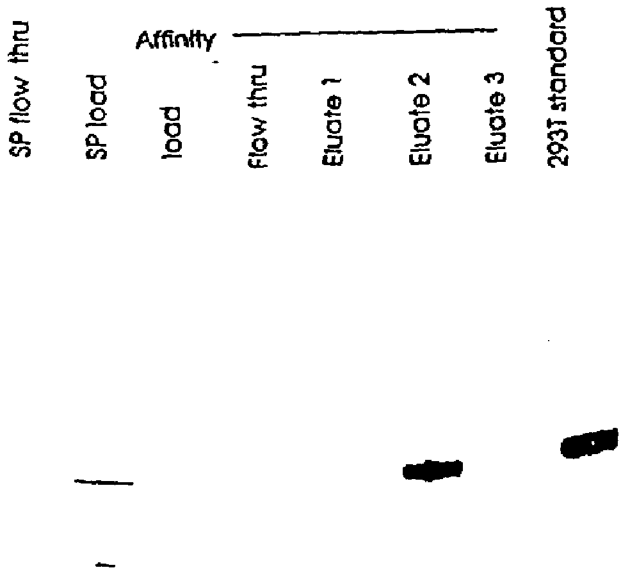
FIG. 8 shows a silver-stained SDS-PAGE of β-secretase purified from heterologous Cos A2 cells expressing the recombinant enzyme.

Example 5 also describes purification schemes used for purifying recombinant materials from heterologous cells transfected with the β-secretase coding sequence. Results from these purifications are illustrated in FIGS. 7 and 8.

2. Sequencing of β-Secretase Protein

A schematic overview summarizing methods and results for determining the cDNA sequence encoding the N-terminal peptide sequence determined from purified β-secretase is shown in FIG. 9. N-terminal sequencing of purified β-secretase protein isolated from natural sources yielded a 21-residue peptide, as described above. This peptide sequence, and its reverse translated fully degenerate nucleotide sequence, is shown in the top portion of FIG. 9. Two partially degenerate primer sets used for RT-PCR amplification of a cDNA fragment encoding this peptide are also summarized in FIG. 4. Primer set 1 consisted of DNA nucleotide primers #3427-3434, shown in Table 3 (Example 3). Matrix RT-PCR using combinations of primers from this set with cDNA reverse transcribed from primary human neuronal cultures as template yielded the predicted 54 bp cDNA product with primers #3428+3433.

In further experiments carried out in support of the present invention, it was found that oligonucleotides from primer sets 1 and 2 could also be used to amplify cDNA fragments of the predicted size from mouse brain mRNA. DNA sequence demonstrated that such primers could also be used to clone the murine homolog(s) and other species homologs of human β-secretase and/or additional members of the aspartyl protease family described herein by standard RACE-PCR technology. The sequence of a murine homolog is presented in FIG. 10 (lowest sequence; "pBS/MulmPain H#3 cons). The polypeptide sequence is about 95% identical to the human polypeptide sequence.

3. 5' and 3' RACE-PCR for Additional Sequence, Cloning, and mRNA Analysis

The unambiguous internal nucleotide sequence from the amplified fragment provided information which facilitated the design of internal primers matching the upper (coding) strand for 3' RACE, and lower (non-coding) strand for 5' RACE (Frohman, M. A., M. K. Dush and G. R. Martin (1988). "Rapid production of full-length cDNAs from rare transcripts: amplification using a single gene specific oligonucleotide primer." *Proc. Natl. Acad. Sci. U.S.A.* 85(23): 8998-9002.) The DNA primers used for this experiment (#3459 & #3460) are illustrated schematically in FIG. 4, and the exact sequence of these primers is presented in Table 3 of Example 3.

Primers #3459 and #3476 were used for initial 3' RACE amplification of downstream sequences from the IMR-32 cDNA library in the vector pLPCXlox. The library had previously been sub-divided into 100 pools of 5,000 clones per pool, and plasmid DNA was isolated from each pool. A survey of the 100 pools with the primers described in Section II, above, as diagnostic for presence of the β-secretase clone identified individual pools from the library for RACE-PCR.

An approximately 1.8 Kb PCR fragment was observed upon agarose gel fractionation of the reaction products. The PCR product was purified from the gel and subjected to DNA sequence analysis using primer #3459. The resulting sequence, designated 23A, was determined. Six of the first seven deduced amino-acids from one of the reading frames of 23A were an exact match with the last 7 amino-acids of the N-terminal sequence determined from the purified protein isolated from natural sources in other experiments carried out in support of this invention. This observation validated the sequence, and defined the proper reading frame downstream. Furthermore, this DNA sequence facilitated design of additional primers for extending the sequence further downstream, verifying the sequence by sequencing the opposite strand in the upstream direction, and further facilitated isolating the cDNA clone.

The DNA sequence of human β-secretase is illustrated as SEQ ID NO: 42 corresponding to SEQ ID NO: 1 including the 5'- and 3'-untranslated regions. This sequence was determined from a partial cDNA clone (9C7e.35) isolated from a commercially available human fetal brain cDNA library purchased from OriGene™, the 3' RACE product 23A, and additional clones—a total of 12 independent cDNA clones were used to determine the composite sequence. The composite sequence was assembled by sequencing overlapping stretches of DNA from both strands of the clone or PCR fragment. The predicted full length translation product is shown as SEQ ID NO: 2 in FIG. 1B.

4. Tissue Distribution of β-Secretase and Related Transcripts

Oligonucleotide primer #3460 was employed as an end-labeled probe on Northern blots to determine the size of the transcript encoding β-secretase, and to examine its expression in IMR-32 cells. Additional primers were used to isolate the mouse cDNA and to characterize mouse tissues, using Marathon RACE ready cDNA preparations (Clontech, Palo Alto Calif.). TABLE 2 summarizes the results of experiments in which various human and murine tissues were tested for the presence of β-secretase-encoding transcripts by PCR or Northern blotting.

The oligo-nucleotide probe 3460 (SEQ ID NO: 39) hybridized to a 2 Kb transcript in IMR-32 cells, indicating that the mRNA encoding the β-secretase enzyme is 2 Kb in size in this tissue. Northern blot analysis of total RNA isolated from the human T-cell line Jurkat, and human myelomonocyte line Thp1 with the 3460 oligo-nucleotide probe 3460 also revealed the presence of a 2 kb transcript in these cells.

The oligonucleotide probe #3460 also hybridizes to a ~2 kb transcript in Northern blots containing RNA from all human organs examined to date, from both adult and fetal tissue. The organs surveyed include heart, brain, liver, pancreas, placenta, lung, muscle, uterus, bladder, kidney, spleen, skin, and small intestine. In addition, certain tissues, e.g. pancreas, liver, brain, muscle, uterus, bladder, kidney, spleen and lung, show expression of larger transcripts of ~4.5 kb, 5 kb, and 6.5 kb which hybridize with oligonucleotide probe #3460.

In further experiments carried out in support of the present invention, Northern blot results were obtained with oligonucleotide probe #3460 by employing a riboprobe derived from SEQ ID NO: 1, encompassing nucleotides #155-1014. This clone provides an 860 bp riboprobe, encompassing the catalytic domain-encoding portion of β-secretase, for high stringency hybridization. This probe hybridized with high specificity to the exact match mRNA expressed in the samples being examined. Northern blots of mRNA isolated from IMR-32 and 1° HNC probed with this riboprobe revealed the presence of the 2 kb transcript previously detected with oligonucleotide #3460, as well as a novel, higher MW transcript of ~5 kb. Hybridization of RNA from adult and fetal human tissues with this 860 nt riboprobe also confirmed the result obtained with the oligonucleotide probe #3460. The mRNA encoding β-secretase is expressed in all tissues examined, predominantly as an ~5 kb transcript. In adult, its expression is lowest in brain, placenta, and lung, intermediate in uterus, and bladder, and highest in heart, liver, pancreas, muscle, kidney, spleen, and lung. In fetal tissue, the message is expressed uniformly in all tissues examined.

TABLE 2

Tissue distribution of human and murine β-secretase transcripts

| | Messages Found: | |
|---|---|---|
| Tissue/Organ | Human | Mouse |
| Heart | 5 Kb | 4.5 Kb |
| Brain | 5 Kb (very faint) | 4.5 Kb, 2 Kb |
| Liver | 5 Kb | 4.5 Kb, 2 Kb |
| Pancreas | 5 Kb | nd |
| Placenta | 0 | nd |
| Lung | 5 Kb | 0 |
| Muscle | 5 Kb | 0 |
| Uterus | 5 Kb | nd |
| Bladder | 5 Kb | nd |
| Kidney | 5 Kb | 4.5 Kb, 2 Kb |
| Spleen | 5 Kb | nd |
| Testis | nd | 4.5 Kb, 2 Kb |
| f Brain | 5 Kb (>>adult) | nd |
| f Liver | 5 Kb (a lot) | nd |
| f Lung | 5 Kb | nd |
| f Muscle | 5 Kb | nd |
| f Heart | ~5 Kb | nd |
| f Kidney | ~5 Kb | nd |
| f Skin | ~5 Kb | nd |
| f Sm. Intestine | ~5 Kb | nd |

TABLE 2-continued

| Tissue distribution of human and murine β-secretase transcripts | | |
|---|---|---|
| E11 | nd | 4.5 Kb, 2 Kb |
| E14 | nd | 4.5 Kb, 2 Kb |
| E17 | nd | 4.5 Kb, 2 Kb |
| E18 | nd | 4.5 Kb, 2 Kb |
| (rat) P18 | nd | 0 |

| | Clontech Human Brain region |
|---|---|
| Tissue/Organ | Human |
| Cerebellum | 2 Kb, 4 Kb, 6 Kb |
| Cerebral Cx | 2 Kb, 4 Kb, 6 Kb |
| Medulla | 2 Kb, 4 Kb, 6 Kb |
| Spinal Cord | 2 Kb, 4 Kb, 6 Kb |
| Occipital Pole | 2 Kb, 4 Kb, 6 Kb |
| Frontal Lobe | 2 Kb, 4 Kb, 6 Kb |
| Putamen | 0 |
| Amygdala | 2 Kb, 4 Kb, 6 Kb |
| Caudate N. | 2 Kb, 4 Kb, 6 Kb |
| Corpus Callosum | 2 Kb, 4 Kb, 6 Kb |
| Hippocampus | 2 Kb, 4 Kb, 6 Kb |
| Whole Br. | 0 |
| Substantia Nigra | 2 Kb, 4 Kb, 6 Kb |
| Thalamus | 2 Kb, 4 Kb, 6 Kb |

| Cell Line | Human | Mouse |
|---|---|---|
| IMR32 | 2 Kb* | |
| U937 | 2 Kb* | |
| THP1 | 2 Kb* | |
| Jurkat | 2 Kb* | |
| J774 | | 5 Kb, 2 Kb |
| P388D1 ccl46 | | 5 Kb (very little), 2 Kb |
| P19 | | 5 Kb, 2 Kb |
| RBL | | 5 Kb, 2 Kb |
| EL4 | | 5 Kb, 2 Kb |
| IC21 | | 0 |
| C2C12 | | 0 |

Notes
*By Oligo 3460 only

5. Active Forms of β-Secretase a. N-Terminus

The full-length open reading frame (ORF) of human β-secretase is described above, and its sequence is shown in FIG. 2A as SEQ ID NO: 2. However, as mentioned above, a further discovery of the present invention indicates that the active, naturally occurring molecule is truncated at the N-terminus by about 45 amino acids. That is, the purified protein was N-terminal sequenced according to methods known in the art (Argo Bioanalytica, Morris Plains, N.J.). The N-terminus yielded the following sequence: ETDEEPEEPGR-RGSFVEMVDNLRG . . . (SEQ ID NO: 55). This corresponds to amino acids 46-66 of the ORF-derived putative sequence. Based on this observation and others described below, it is believed that the N-terminus of the active, naturally occurring, predominant human brain form of the enzyme is amino acid 46, with respect to SEQ ID NO: 2. Further processing of the purified protein provided the sequence of an internal peptide: ISFAVSACHVHDEFR (SEQ ID NO: 56), which is amino terminal to the putative transmembrane domain, as defined by the ORF. These peptides were used to validate and provide reading frame information for the isolated clones described elsewhere in this application.

In additional studies carried out in support of the present invention, β-secretase isolated from additional tissues revealed that the N-terminus may be amino acid 46, 22, 58, or 63 with respect to the ORF sequence shown in FIG. 2A, depending on the tissue from which the protein is isolated, with the form starting at amino acid 46 predominating in the tissues tested. That is, the full-length β-secretase construct (i.e., encoding SEQ ID NO: 2) was transfected into 293T cells and COS A2 cells, using the Fugene technique described in Example 6. β-secretase was isolated from the cells by preparing a crude particulate fraction from the cell pellet, as described in Example 5, followed by extraction with buffer containing 0.2% Triton X-100. The Triton extract was diluted with pH 5.0 buffer and passed through a SP Sepharose column, essentially according to the methods described in Example 5A. This step removed the majority of proteins. After adjusting the pH to 4.5, β-secretase was concentrated, with some additional purification, on P10-P4'staD→V Sepharose, as described in Examples 5 and 7. Fractions were analyzed for N-terminal sequence, according to standard methods known in the art. Results are summarized in Table 3, below.

The primary N-terminal sequence of the 293T cell-derived protein was the same as that obtained from brain. In addition, minor amounts of protein starting just after the signal sequence (at Thr-22) and at the start of the aspartyl protease homology domain (Met-63) were also observed. An additional major form found in Cos A2 cells resulted from a Gly-58 cleavage.

TABLE 3

N-terminal Sequences and Amounts of β-secretase Forms in Various Cell Types

| Source | Est. Amount (pmoles) | N-terminus (Ref.: SEQ ID NO: 2) | Sequence |
|---|---|---|---|
| Human brain | 1-2 | 46 | ETDEEPEEPGR . . . (SEQ ID NO: 88) |
| Recombinant, 293T | ~35 | 46 | ETDEEPEEPGR . . . (SEQ ID NO: 88) |
| | ~7 | 22 | TQHGIRL(P)LR . . . (SEQ ID NO: 89) |
| | ~5 | 63 | MVDNLRGKS . . . (SEQ ID NO: 90) |
| Recombinant, CosA2 | ~4 | 46 | ETDEEPEEPGR . . . (SEQ ID NO: 88) |
| | ~3 | 58 | GSFVEMVDNL . . . (SEQ ID NO: 91) |

b. C-Terminus

Further experiments carried out in support of the present invention revealed that the C-terminus of the full-length amino acid sequence presented as SEQ ID NO: 2 can also be truncated, while still retaining β-secretase activity of the molecule. More specifically, as described in more detail in Part D, below, C-terminal truncated forms of the enzyme ending just before the putative transmembrane region, i.e. at amino acid 452 with respect to SEQ ID NO: 2, exhibit β-secretase activity, as evidenced by an ability to cleave APP at the appropriate cleavage site.

Thus, using the reference amino acid positions provided by SEQ ID NO: 2, one form of β-secretase extends from position 46 to position 501 (β-secretase 46-501; SEQ ID NO: 43). Another form extends from position 46 to any position including and beyond position 452, (β-secretase 4-452+), with a preferred form being β-secretase 46-452 (SEQ ID NO: 58). More generally, another preferred form extends from position 1 to any position including and beyond position 452, but not including position 501. Other active forms begin at 22, 58, or 63 and may extend to any point including and beyond the cysteine at position 420, and more preferably, including and beyond position 452, while still retaining enzymatic activity (β-secretase 22-452+; β-secretase 58-452+; β-secretase 63-452+). As described in Part D, below, those forms which are truncated at C-terminal position at or before about position 452, or even several amino acids thereafter, are particularly useful in crystallization studies, since they lack the putative transmembrane region, which may interfere with protein crystallization. The recombinant protein extending from position 1 to 452 has been affinity purified to apparent homogeneity, using the procedures described elsewhere in this application.

C. Crystallization of β-Secretase

According to a further aspect, the present invention also includes purified β-secretase in crystallized form, in the absence or presence of binding substrates, such as peptide, modified peptide, or small molecule inhibitors. This section describes methods and utilities of such compositions.

1. Crystallization of the Protein

β-secretase purified as described in Part B.1, above can be used as starting material to determine a crystallographic structure and coordinates for the enzyme. Such structural determinations are particularly useful in defining the conformation and size of the substrate binding site. This information can be used in the design and modeling of substrate inhibitors of the enzyme. As discussed herein, such inhibitors are candidate molecules for therapeutics for treatment of Alzheimer's disease and other amyloid diseases characterized by Aβ peptide amyloid deposits.

The crystallographic structure of β-secretase is determined by first crystallizing the purified protein. Methods for crystallizing proteins, and particularly proteases, are now well known in the art. The practitioner is referred to *Principles of Protein X-ray Crystallography*(J. Drenth, Springer Verlag, N.Y., 1999) for general principles of crystallography. Additionally, kits for generating protein crystals are generally available from commercial providers, such as Hampton Research (Laguna Niguel, Calif.). Additional guidance can be obtained from numerous research articles that have been written in the area of crystallography of protease inhibitors, especially with respect to HIV-1 and HIV-2 proteases, which are aspartic acid proteases.

Although any of the various forms of β-secretase described herein can be used for crystallization studies, particularly preferred forms lack the first 45 amino acids of the full length sequence shown as SEQ ID NO: 2, since this appears to be the predominant form which occurs naturally in human brain. It is thought that some form of post-translational modification, possibly autocatalysis, serves to remove the first 45 amino acids in fairly rapid order, since virtually no naturally occurring enzyme has been isolated with all of the first 45 amino acids intact. In addition, it is considered preferable to remove the putative transmembrane region from the molecule prior to crystallization, since this region is probably not involved in catalysis and potentially could render the molecule more difficult to crystallize.

Thus, a good candidate for crystallization is β-secretase 46-452 (SEQ ID NO: 58), since this is a form of the enzyme that (a) provides the predominant naturally occurring N-terminus, and (b) lacks the "sticky" transmembrane region, while (c) retaining β-secretase activity. In general, for determining X-ray crystallographic coordinates of the ligand binding site, any form of the enzyme can be used that either (i) exhibits β-secretase activity, and/or (ii) binds to a known inhibitor, such as the inhibitor ligand P10-P4'staD→V, with a binding affinity that is at least 1/100 the binding affinity of P10-P4'staD→V. Therefore, a number of additional truncated forms of the enzyme can be used in these studies. Suitability of any particular form can be assessed by contacting it with the P10-P4'staD→V affinity matrix described above. Truncated forms of the enzyme that bind to the matrix are suitable for such further analysis. Thus, in addition to 46-452, discussed above, experiments in support of the present invention have revealed that a truncated form ending in residue 419, most likely 46-419, also binds to the affinity matrix and is therefore an alternate candidate protein composition for X-ray crystallographic analysis of β-secretase. More generally, any form of the enzyme that ends before the transmembrane domain, particularly those ending between about residue 419 and 452 are suitable in this regard.

At the N-terminus, as described above, generally the first 45 amino acids will be removed during cellular processing. Other suitable naturally occurring or expressed forms are listed in Table 3 above. These include, for example, a protein commencing at residue 22, one commencing at residue 58 and one commencing at residue 63. However, analysis of the entire enzyme, starting at residue 1, can also provide information about the enzyme. Other forms, such as 1-420 (SEQ ID NO 60) to 1-452 (SEQ ID NO: 59), including intermediate forms, for example 1-440, can be useful in this regard. In general, it will also be useful to obtain structure on any subdomain of the active enzyme.

Methods for purifying the protein, including active forms, are described above. In addition, since the protein is apparently glycosylated in its naturally occurring (and mammalian-expressed recombinant) forms, it may be desirable to express the protein and purify it from bacterial sources, which do not glycosylate mammalian proteins, or express it in sources, such as insect cells, that provide uniform glycosylation patterns, in order to obtain a homogeneous composition. Appropriate vectors and codon optimization procedures for accomplishing this are known in the art.

Following expression and purification, the protein is adjusted to a concentration of about 1-20 mg/ml. In accordance with methods that have worked for other crystallized proteins, the buffer and salt concentrations present in the initial protein solution are reduced to as low a level as possible. This can be accomplished by dialyzing the sample against the starting buffer, using microdialysis techniques known in the art. Buffers and crystallization conditions will vary from protein to protein, and possibly from fragment to fragment of the active β-secretase molecule, but can be determined empirically using, for example, matrix methods for determining optimal crystallization conditions. (Drentz, J., supra; Ducruix, A., et al., eds. *Crystallization of Nucleic Acids and Proteins: A Practical Approach*, Oxford University Press, New York, 1992.)

Following dialysis, conditions are optimized for crystallization of the protein. Generally, methods for optimization may include making a "grid" of 1 μl drops of the protein solution, mixed with 1 μl well solution, which is a buffer of varying pH and ionic strength. These drops are placed in individual sealed wells, typically in a "hanging drop" configuration, for example in commercially available containers (Hampton Research, Laguna Niguel, Calif.). Precipitation/crystallization typically occurs between 2 days and 2 weeks. Wells are checked for evidence of precipitation or crystallization, and conditions are optimized to form crystals. Optimized crystals are not judged by size or morphology, but rather by the diffraction quality of crystals, which should provide better than 3 Å resolution. Typical precipitating agents include ammonium sulfate ($NH_4SO_4$), polyethylene glycol (PEG) and methyl pentane diol (MPD). All chemicals used should be the highest grade possible (e.g., ACS) and may also be re-purified by standard methods known in the art, prior to use.

Exemplary buffers and precipitants forming an empirical grid for determining crystallization conditions are available. For example, the "Crystal Screen" kit (Hampton Research) provides a sparse matrix method of trial conditions that is biased and selected from known crystallization conditions for macromolecules. This provides a "grid" for quickly testing wide ranges of pH, salts, and precipitants using a very small sample (50 to 100 microliters) of macromolecule. In such studies, 1 μl of buffer/precipitant(s) solution is added to an equal volume of dialyzed protein solution, and the mixtures are allowed to sit for at least two days to two weeks, with careful monitoring of crystallization. Chemicals can be obtained from common commercial suppliers; however, it is preferable to use purity grades suitable for crystallization studies, such as are supplied by Hampton Research (Laguna Niguel, Calif.). Common buffers include Citrate, TEA, CHES, Acetate, ADA and the like (to provide a range of pH optima), typically at a concentration of about 100 mM. Typical precipitants include $(NH_4)_2SO_4$, $MgSO_4$, NaCl, MPD, Ethanol, polyethylene glycol of various sizes, isopropanol, KCl; and the like (Ducruix).

Various additives can be used to aid in improving the character of the crystals, including substrate analogs, ligands, or inhibitors, as discussed in Part 2, below, as well as certain additives, including, but not limited to:

5% Jeffamine

5% Polypropyleneglycol P400

5% Polyethyleneglycol 400

5% ethyleneglycol

5% 2-methyl-2,4-pentanediol

5% Glycerol

5% Dioxane

5% dimethyl sulfoxide

5% n-Octanol 100 mM (NH4)2SO4

100 mM CsCl 100 mM CoSO4

100 mM MnCl2

100 mMKCl 100 mM ZnSO4

100 mM LiCl2

100 mM MgCl2

100 mM Glucose 100 mM 1,6-Hexanediol 100 mM Dextran sulfate 100 mM 6-amino caproic acid 1100 mM 1,6 hexane diamine 100 mM 1,8 diamino octane 100 mM Spermidine 100 mM Spermine 0.17 mM n-dodecyl-13-D-maltoside NP 40

20 mM n-octyl-13-D-glucopyranoside

According to one discovery of the present invention, the full-length β-secretase enzyme contains at least one transmembrane domain, and its purification is aided by the use of a detergent (Triton X-100). Membrane proteins can be crystallized, but may require specialized conditions, such as the addition of a non-ionic detergent, such as $C_8G$ (8-alkyl-β-glucoside) or an n-alkyl-maltoside ($C_nM$). Selection of such a detergent is somewhat empirical, but certain detergents are commonly employed in this. A number of membrane proteins have been successfully "salted out" by addition of high salt concentrations to the mixture. PEG has also been used successfully to precipitate a number of membrane proteins (Ducruix, et al., supra). Alternatively, as discussed above, a C-terminal truncated form of the protein, lacking the transmembrane domain, such as β-secretase 46-452, is crystallized.

After crystallization conditions are determined, crystallization of a larger amount of the protein can be achieved by methods known in the art, such as vapor diffusion or equilibrium dialysis. In vapor diffusion, a drop of protein solution is equilibrated against a larger reservoir of solution containing precipitant or another dehydrating agent. After sealing, the solution equilibrates to achieve supersaturating concentrations of proteins and thereby induce crystallization in the drop.

Equilibrium dialysis can be used for crystallization of proteins at low ionic strength. Under these conditions, a phenomenon known as "salting in" occurs, whereby the protein molecules achieve balance of electrostatic charges through interactions with other protein molecules. This method is particularly effective when the solubility of the protein is low at the lower ionic strength. Various apparatuses and methods are used, including microdiffusion cells in which a dialysis membrane is attached to the bottom of a capillary tube, which may be bent at its lower portion. The final crystallization condition is achieved by slowly changing the composition of the outer solution. A variation of these methods utilizes a concentration gradient equilibrium dialysis set up. Microdiffusion cells are available from commercial suppliers such as Hampton Research (Laguna Niguel, Calif.).

Once crystallization is achieved, crystals are subjected to X-ray diffraction, using a strong, monochromatic X-ray source, such as a Synchrotron source or rotating anode generator, and the resulting X-ray diffraction patterns are analyzed, using methods known in the art.

2. Crystallization of Protein Plus Inhibitor

As mentioned above, it is advantageous to co-crystallize the protein in the presence of a binding ligand, such as inhibitor. Generally, the process for optimizing crystallization of the protein is followed, with addition of greater than 1 mM concentration of the inhibitor ligand during the precipitation phase. These crystals are also compared to crystals formed in the absence of ligand, so that measurements of the ligand binding site can be made. Alternatively, 1-2 μl of 0.1-25 mM inhibitor compound is added to the drop containing crystals grown in the absence of inhibitor in a process known as "soaking." Based on the coordinates of the binding site, further inhibitor optimization is achieved. Such methods have been used advantageously in finding new, more potent inhibitors for HIV proteases (See, e.g., Viswanadhan, V. N., et al. J. Med. Chem. 39: 705-712, 1996; Muegge, I., et al. J. Med. Chem. 42: 791-804, 1999).

One inhibitor ligand which is used in these co-crystallization and soaking experiments is P10-P4'staD→V, a statine-containing peptide inhibitor described above. Other inhibitors include the heptapeptide molecules disclosed in the invention which also containing a statine or statine derivative or hydroxyethylene molecule. Methods for making these molecules are described herein. The inhibitor is mixed with β-secretase, and the mixture is subjected to the same optimization tests described above, concentrating on those conditions worked out for the enzyme alone. Coordinates are determined and comparisons are made between the free and ligand bound enzyme, according to methods well known in the art. Further comparisons can be made by comparing the inhibitory concentrations of the enzyme to such coordinates, such as described by Viswanadhan, et al, supra. Analysis of such comparisons provides guidance for design of further inhibitors, using this method.

D. Biological Activity of β-Secretase

1. Naturally Occurring β-Secretase

Figure 11:
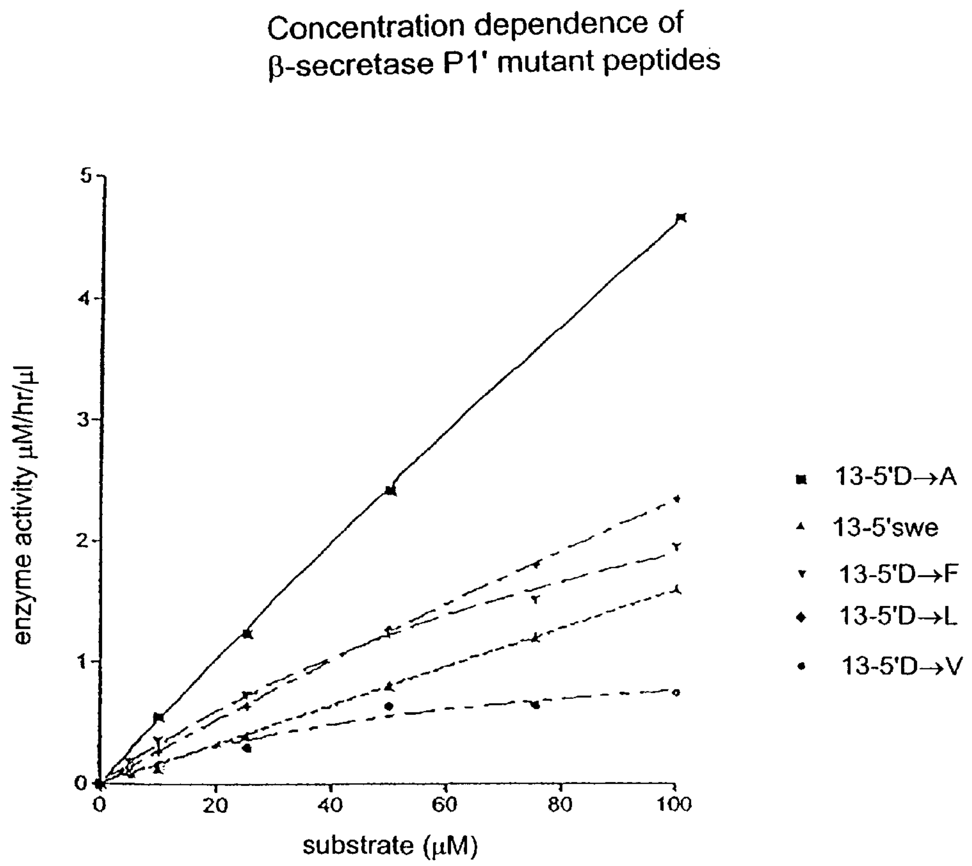
FIG. 11 shows a plot of substrate dependence of P20-P4' peptide digests.

In studies carried out in support of the present invention, isolated, purified forms of β-secretase were tested for enzymatic activity using one or more native or synthetic substrates. For example, as discussed above, when β-secretase was prepared from human brain and purified to homogeneity using the methods described in Example 5A, a single band was observed by silver stain after electrophoresis of sample fractions from the anion exchange chromatography (last step) on an SDS-polyacrylamide gel under reducing (+β-mercaptoethanol)conditions. As summarized in Table 1, above, this fraction yielded a specific activity of approximately $1.5\times10^{9}$ nM/h/mg protein, where activity was measured by hydrolysis of MBP-C125SW. FIG. 11 shows substrate concentration dependence of hydrolysis by brain β-secretase with respect to the Swedish mutant P13-P5' peptide, Swedish mutant P13-P5' with P1'aspartic acid replaced with an alanine (D→A), a valine (D→V), a phenylalanine (D→F), a leucine (D→L), and wild type APP (plotted at 10× amounts for visibility). The valine and leucine substituted Swedish peptides show saturation at a lower concentration than the parent Swedish peptide. This likely indicates a higher binding affinity to the enzyme.

2. Isolated Recombinant β-Secretase

Various recombinant forms of the enzyme were produced and purified from transfected cells. Since these cells were made to overproduce the enzyme, it was found that the purification scheme described with respect naturally occurring forms of the enzyme (e.g., Example 5A) could be shortened, with positive results. For example, as detailed in Example 6, 293T cells were transfected with pCEKclone 27 (FIG. 12 and FIGS. 13A-E) and Cos A2 cells were transfected with pCFβA2 using "FUGENE" 6 Transfection Reagent (Roche Molecular Biochemicals Research, Indianapolis, Ind.). The vector pCF was constructed from the parent vector pCDNA3, commercially available from Invitrogen, by inserting the following sequence between the HindIII and EcoRI sites:

```
CTGTTGGGCTCGCGGTTGAGGACAAACTCTTCGCGGTCTTTCCAGTACTCTTG  (SEQ ID NO:80)
GATCGGAAACCCGTCGGCCTCCGAACGGTACTCCGCCACCGAGGGACCTGAG
CGAGTCCGCATCGACCGGATCGGAAAACCTCTCGACTGTTGGGGTGAGTACT
CCCTCTCAAAAGCGGGCATGACTTCTGCGCTAAGATTGTCAGTTTCCAAAAAC
GAGGAGGATTTGATATTCACCTGGCCCGCGGTGATGCCTTTGAGGGTGGCCG
CGTCCATCTGGTCAGAAAAGACAATCTTTTTGTTGTCAAGCTTGAGGTGTGGC
AGGCTTGAGATCTGGCCATACACTTGAGTGACAATGACATCCACTTTGCCTTT
CTFTCCACAGGTGTCCACTCCCAGGTCCAACTGCAGGTCGACTCTAGACCC
```

This sequence encompasses the adenovirus major late promoter tripartite leader sequence, and a hybrid splice created from adenovirus major late region first exon and intron and a synthetically generated IgG variable region splice acceptor.

pCDNA3 was cut with restriction endonucleases HindIII and EcoRI, then blunted by filling in the ends with Klenow fragment of DNA polymerase I. The cut and blunted vector was gel purified, and ligated with isolated fragment from pED.GI. The pED fragment was prepared by digesting with PvuII and SmaI, followed by gel purification of the resulting 419 base-pair fragment.

pED: 5'=PvuII 3'=SmaI pcDNA3: 5'=(HindIII) 3'=(EcoRI)

Screened for orientation, and confirmed by sequencing.

To create the pCEK expression vector, the expression cassette from pCF was transferred into the EBV expression vector pCEP4 (Invitrogen, Carlsbad, Calif.). pCEP 4 was cut with BglII and XbaI, filled in, and the large 9.15 kb fragment containing pBR, hygromycin, and EBV sequences) ligated to the 1.9 kb NruI to XmnI fragment of pCF containing the expression cassette (CMV, TPL/MLP/IGg splice, Sp6, SVpolyA, M13 flanking region).

pCFβA2 (clone A2) contains full length β-secretase in the vector pCF. pCF vector replicates in COS and 293T cells. In each case, cells were pelleted and a crude particulate fraction was prepared from the pellet. This fraction was extracted with buffer containing 0.2% Triton X-100. The Triton extract was diluted with pH 5.0 buffer and passed through a SP Sepharose column. After the pH was adjusted to 4.5, β-secretase activity containing fractions were concentrated, with some additional purification on P10-P4'(statine)D→V Sepharose, as described for the brain enzyme. Silver staining of fractions revealed co-purified bands on the gel. Fractions corresponding to these bands were subjected to N-terminal amino acid determination. Results from these experiments revealed some heterogeneity of β-secretase species within the fractions. These species represent various forms of the enzyme; for example, from the 293T cells, the primary N-terminus is the same as that found in the brain, representing amino acid 46 at the N-terminus. Minor amounts of protein starting just after the signal sequence at residue 23 and at the start of the aspartyl protease homology domain (Met-63) were also observed. An additional major form of protein was found in Cos A2 cells, resulting from cleavage at Gly-58.

3. Comparison of Isolated, Naturally Occurring β-Secretase with Recombinant β-Secretase As described above, both naturally occurring β-secretase derived from human brain and recombinant forms of the enzyme exhibit activity in cleaving APP, particularly as evidenced by activity in the MBP-C125 assay. Further, key peptide sequences from the naturally occurring form of the enzyme-matched portions of the deduced sequence derived from cloning the enzyme. Further confirmation that the two enzymes act identically can be taken from additional experiments in which various inhibitors were found to have very similar affinities for the enzymes, as estimated by $IC_{50}$ values in a similar assay. These inhibitors were discovered in accordance with a further aspect of the invention, which is described below. Significantly, the inhibitors produce near identical $IC_{50}$ values and rank orders of potency in brain-derived and recombinant enzyme preparations, when compared in the same assay. These results are summarized in Table 4.

TABLE 4

Rank Order of Inhibition of Recombinant and Human Brain β-secretase

| Inhibitor | MBP-C125 Assay Recombinant Relative $IC_{50}$[a] | MBP-C125 Assay Brain Relative $IC_{50}$[a] | P26-P4'Assay Recombinant Relative $IC_{50}$[a] | P26-P4'Assay Brain Relative $IC_{50}$[a] |
|---|---|---|---|---|
| A | 1 | 1 | 1 | 1 |
| B | 1 | 2 | 1 | 2 |
| C | 2 | 3 | 2 | 3 |
| D | 3 | 4 | 3 | 4 |
| E | 4 | 5 | 4 | 5 |

[a]Relative rank orders are provided, "1"indicates the lowest $IC_{50}$ in each group. $IC_{50}$s were approximately the same when recombinant and brain enzymes were compared in the same assay. All $IC_{50}$s were less than 10 μM.

In further studies, comparisons were made between the full length recombinant enzyme "FLp501" (SEQ ID NO: 2) and a recombinant enzyme truncated at position 452 "452Stop" (SEQ ID NO: 58 or SEQ ID NO: 59). Both enzymes exhibited activity in cleaving β-secretase substrates such as MBP-C125, as described above. As shown in Table 5, below, the C-terminal truncated form of the enzyme exhibited activity in cleaving both the MBP-C125sw substrate as well as the P26-P4' substrate, with similar rank order of potency for the inhibitor drugs tested. In addition, as above, the absolute $IC_{50}$s were comparable for the two enzymes tested with the same inhibitor. All $IC_{50}$s were less than 10 μM.

TABLE 5

Rank Order of Inhibition of Full-length and truncated forms

| Inhibitor | FLp501 Relative $IC_{50}$ | 452Stop Relative $IC_{50}$ |
|---|---|---|
| A | 1 | 2 |
| B | 1 | 1 |
| C | 2 | 4 |
| D | 2 | 3 |
| E | 3 | 5 |

4. Cellular β-Secretase

Further experiments carried out in support of the present invention have revealed that the isolated β-secretase polynucleotide sequences described herein encode β-secretase or β-secretase fragments that are active in cells. This section describes experiments carried out in support of the present invention, cells were transfected with DNA encoding β-secretase alone, or were co-transfected with DNA encoding-secretase and DNA encoding wild-type APP as detailed in Example 8.

a. Transfection with β-Secretase

Figure 14:
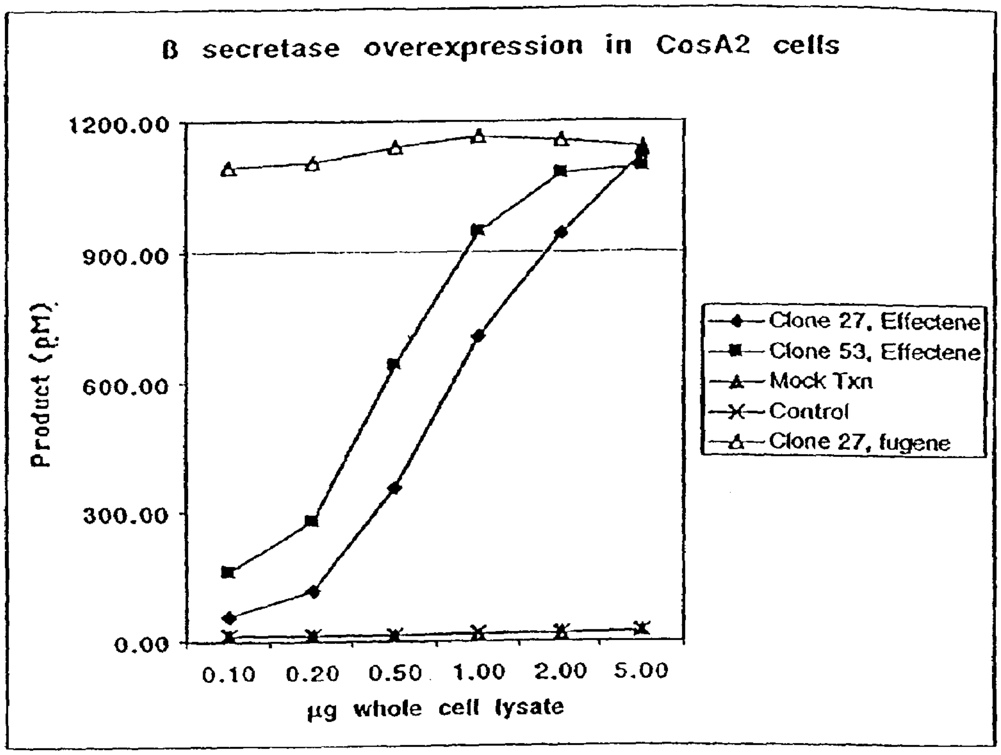
FIG. 14 shows a plot of β-secretase activity in cell lysates from COS cells transfected with vectors derived from clones encoding β-secretase.

In experiments carried out in support of the present invention, clones containing full-length nucleotides (SEQ ID NO: 2) were transfected into COS cells (Fugene and Effectene methods). Whole cell lysates were prepared and various amounts of lysate were tested for β-secretase activity according to standard methods known in the art or described in Example 4 herein. FIG. 14 shows the results of these experiments. As shown, lysates prepared from transfected cells, but not from mock- or control cells, exhibited considerable enzymatic activity in the MPB-C125SW assay, indicating "over-expression" of β-secretase by these cells.

b. Co-Transfection of Cells with β-Secretase and APP

In further experiments, 293T cells were co-transfected with (pCEK clone 27, FIGS. 12 and 13; or poCK vector containing β-secretase) a clone containing the full length β-secretase molecule (1-501; SEQ ID NO: 2) and with aplasmid containing either the wild-type or Swedish APP construct pohCK751, as described in Example 8. β-specific cleavage was analyzed by ELISA and Western analyses to confirm that the correct site of cleavage occurs.

Figure 12:
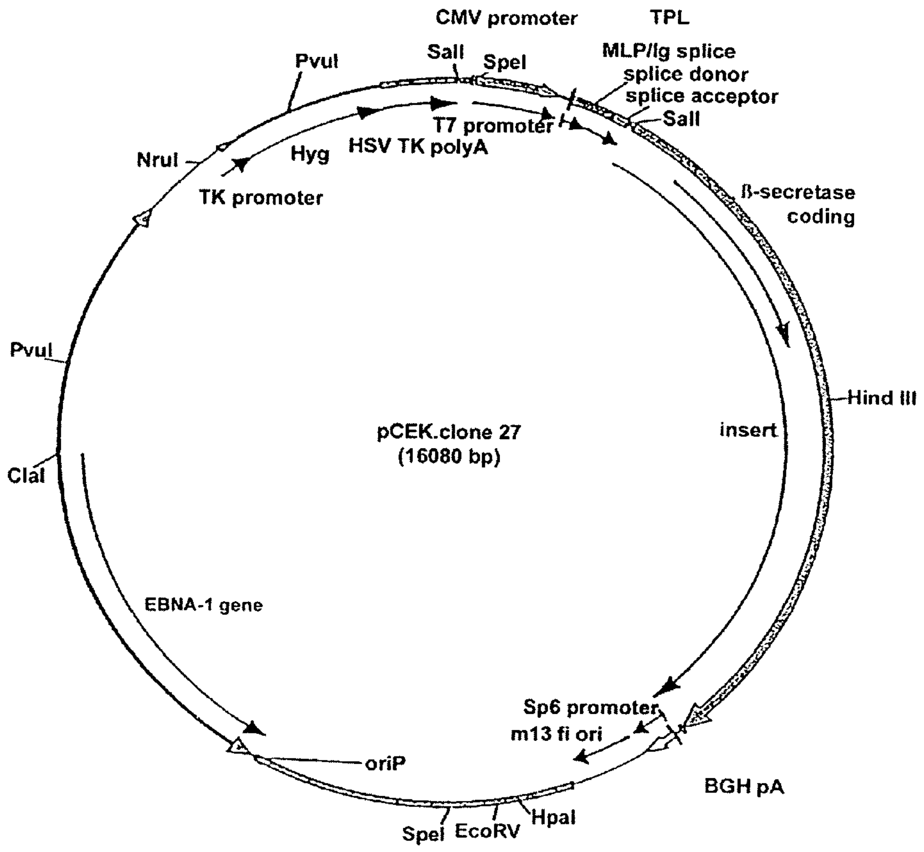
FIG. 12 shows a schematic of pCEK.clone 27 used to transfect mammalian cells with β-secretase.
Figure 21:
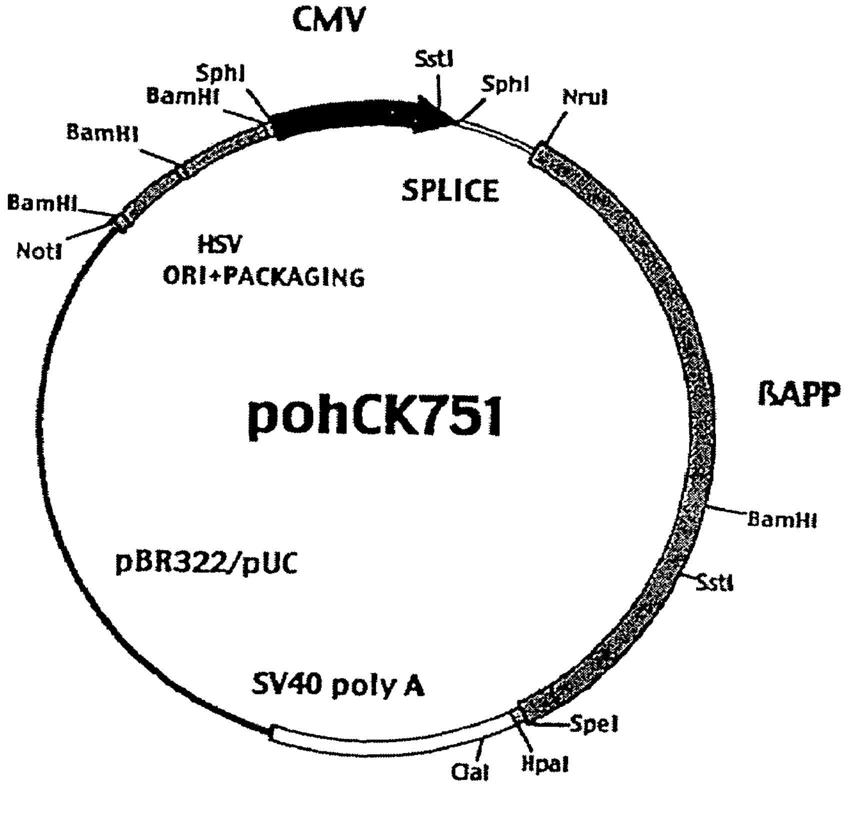
FIG. 21 shows a schematic of pohCK751 vector.

Briefly 293T cells were co-transfected with equivalent amounts of plasmids encoding βAPPsw or wt and β-secretase or control β-galactosidase (β-gal) cDNA according to standard methods. βAPP and β-secretase cDNAs were in delivered via vectors, pohCK or pCEK, which do not replicate in 293T cells (pCEK-clone 27, FIGS. 12 and 13; pohCK751 expressing βAPP 751, FIG. 21). Conditioned media and cell lysates were collected 48 hours after transfection. Western assays were carried out on conditioned media and cell lysates. ELISAs for detection of Aβ peptide were carried out on the conditioned media to analyze various APP cleavage products.

Western Blot Results

It is known that β-secretase specifically cleaves at the Met-Asp in APPwt and the Leu-Asp in APPsw to produce the Aβ peptide, starting at position 1 and releasing soluble APP (sAPPβ). Immunological reagents, specifically antibody 92 and 92sw (or 192sw), respectively, have been developed that specifically detect cleavage at this position in the APPwt and APPsw substrates, as described in U.S. Pat. No. 5,721,130, incorporated herein by reference. Western blot assays were carried out on gels on which cell lysates were separated. These assays were performed using methods well known in the art, using as primary antibody reagents Ab 92 or Ab92S, which are specific for the C terminus of the N-terminal fragment of APP derived from APPwt and APPsw, respectively. In addition, ELISA format assays were performed using antibodies specific to the N terminal amino acid of the C terminal fragment.

Figure 15A:
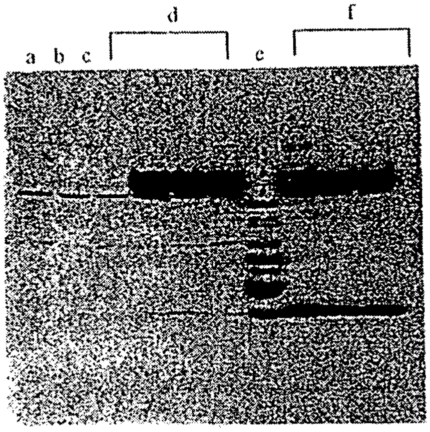
FIGS. 15A and 15B show photos of SDS PAGE gels triplicate samples of the lysates made from heterologous cells transfected with mutant APP (75 lwt) and β-galactosidase as control ("751 wt/βgal") for cells transfected with mutant APP (751 wt) and β-secretase ("751 wt/βsecretase") (15A), and for cells transfected with mutant APP/βgalactosidase ("751sw/βgal") and with APP plus β-galactosidase ("751sw/βsec").
Figure 15B:
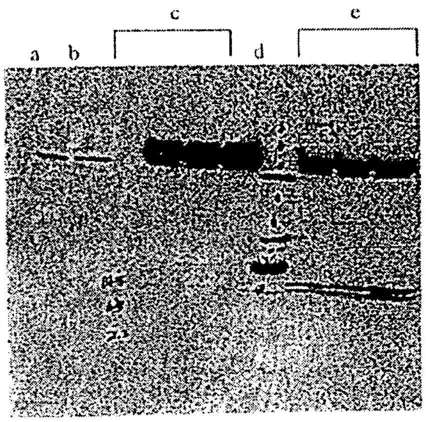

Monoclonal antibody 13G8 (specific for C-terminus of APP—epitope at positions 675-695 of APP695) was used in a Western blot format to determine whether the transfected cells express APP. FIG. 15A shows that reproducible transfection was obtained with expression levels of APP in vast excess over endogenous levels (triplicate wells are indicated as 1, 2, 3 in FIG. 15A). Three forms of APP—mature, immature and endogenous, can be seen in cells transfected with APPwt or APPsw. When β-secretase was co-transfected with APP, smaller C-terminal fragments appeared in triplicate well lanes from co-transfected cells (Western blot FIG. 15A, right-most set of lanes). In parallel experiments, where cells were co-transfected with β-secretase and APPsw substrate, literally all of the mature APP was cleaved (right-most set of lanes labeled "1,2,3" of FIG. 15B). This suggests that there is extensive cleavage by β-secretase of the mature APP (upper band), which results in C-terminal fragments of expected size in the lysate for cleavage at the β-secretase site. Co-transfection with Swedish substrate also resulted in an increase in two different sized CTF fragments (indicated by star). Given the additional Western and ELISA results described below this is consistent with a second cleavage occurring on the APPsw substrate after the initial cleavage at the β-secretase site.

Figure 16A:
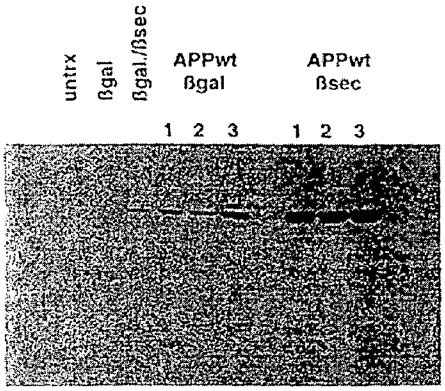
FIGS. 16A and 16B show Western blots of cell supernatants tested for presence or increase in sAPP.
Figure 16B:
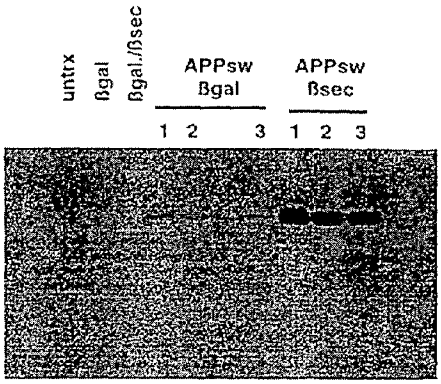

Conditioned medium from the cells was analyzed for reactivity with the 192sw antibody, which is specific for β-s-APPsw. Analysis using this antibody indicated a dramatic increase in β-secretase cleaved soluble APP. This is observed in FIG. 16B by comparing the dark bands present in the "APPsw βsec" samples to the bands present in the "APPsw βgal" samples. 92 antibody specific for β-s-APPwt also indicates an increase in β-secretase cleaved material, as illustrated in FIG. 16A.).

Since the antibodies used in these experiments are specific for the β-secretase cleavage site, the foregoing results show that p501 β-secretase cleaves APP at this site, and the overexpression of this recombinant clone leads to a dramatic enhancement β-secretase processing at the correct β-secretase site in whole cells. This processing works on both the wildtype APP substrate and is enhanced substantially on the Swedish APP substrate. Since approximately 20% of secreted APP in 293 cells is β-sAPP, the increase seen below for APPsw it is probable that most all of the sAPP is β-sAPP. This observation was further confirmed by independent Western assays in which alpha and total sAPP were measured.

Figure 17A:
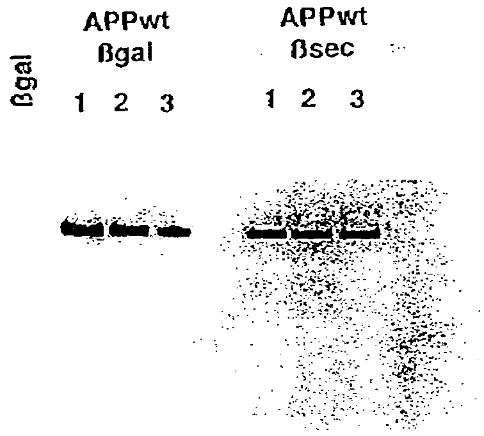
FIGS. 17A and 17B show Western blots of α-cleaved APP substrate in co-expression cells.
Figure 17B:
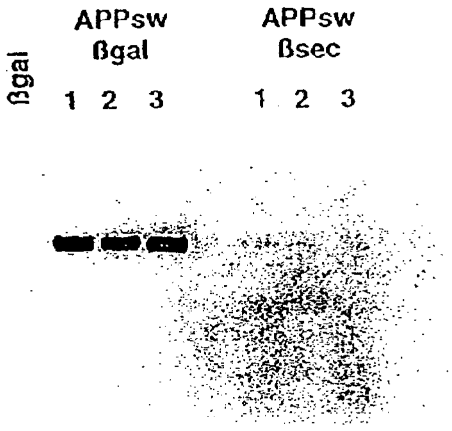

Monoclonal antibody 1736 is specific for the exposed α-secretase cleaved β-APP (Selkoe, et al.). When Western blots were performed using this antibody as primary antibody, a slight but reproducible decrease in α-cleaved APPwt was observed (FIG. 17A), and a dramatic in α-cleaved APPsw material was also observed (note near absence of reactivity in FIG. 17B in the lanes labeled "APPsw βsec"). This indicates that the overexpressed recombinant p501 β-secretase cleaves APPsw so efficiently or extensively that there is little or no substrate remaining for α-secretase to cleave. This further indicates that all the sAPP in APPsw βsec samples (illustrated in FIG. 16B) is β-sAPP.

Aβ ELISA Results

Figure 18:
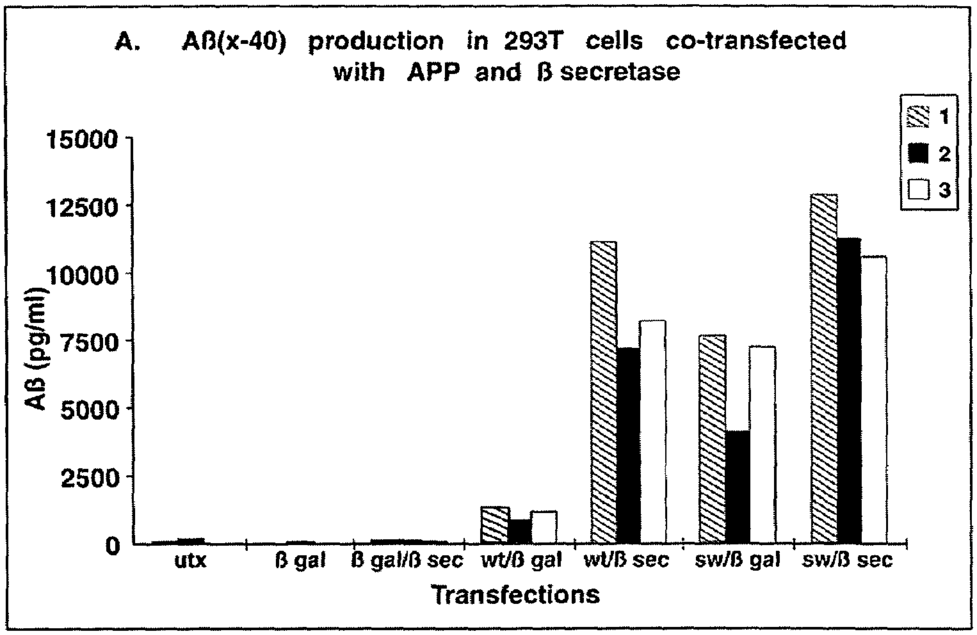
FIG. 18 shows Aβ (x-40) production in 293T cells cotransfected with APP and β-secretase.

Conditioned media from the recombinant cells was collected, diluted as necessary and tested for Aβ peptide production by ELISA on microtiter plates coated with monoclonal antibody 2G3, which is specific for recognizing the C-terminus of Aβ(1-40), with the detector reagent biotinylated mAb 3D6, which measures Aβ(x-40) (i.e., all N-terminus-truncated forms of the peptide). Overexpression of β-secretase with APPwt resulted in an approximately 8-fold increase in Aβ(x-40) production, with 1-40 being a small percentage of the total. There was also a substantial increase in the production of Aβ1-40 (FIG. 18). With APPsw there was an approximate 2-fold increase in Aβ(x-40). Without adhering to any particular underlying theory, it is thought that the less dramatic increase of Aβ(x-40) β-sec/APPsw cells in comparison to the β-sec/APPwt cells is due in part to the fact that processing of the APPsw substrate is much more efficient than that of the APPwt substrate. That is, a significant amount of APPsw is processed by endogenous β-secretase, so further increases upon transfection of β-secretase are therefore limited. These data indicate that the expression of recombinant β-secretase increases Aβ production and that β-secretase is rate limiting for production of Aβ in cells. This means that β-secretase is rate limiting for production of Aβ in cells.

IV. Utility

A. Expression Vectors and Cells Expressing β-Secretase

The invention includes further cloning and expression of members of the aspartyl protease family described above, for example, by inserting polynucleotides encoding the proteins into standard expression vectors and transfecting appropriate host cells according to standard methods discussed below. Such expression vectors and cells expressing, for example, the human β-secretase enzyme described herein, have utility, for example, in producing components (purified enzyme or transfected cells) for the screening assays discussed in Part B, below. Such purified enzyme also has utility in providing starting materials for crystallization of the enzyme, as described in Section III, above. In particular, truncated form(s) of the enzyme, for example 1-452 (SEQ ID NO: 59) and 46-452 (SEQ ID NO:58), and the deglycosylated forms of the enzyme described herein have utility in this regard.

In accordance with the present invention, polynucleotide sequences which encode human β-secretase, splice variants, fragments of the protein, fusion proteins, or functional equivalents thereof, collectively referred to herein as "β-secretase," may be used in recombinant DNA molecules that direct the expression of β-secretase in appropriate host cells. Due to the inherent degeneracy of the genetic code, other nucleic acid sequences that encode substantially the same or a functionally equivalent amino acid sequence may be used to clone and express β-secretase.

The polynucleotide sequences of the present invention can be engineered in order to alter a β-secretase coding sequence for a variety of reasons, including but not limited to, alterations that modify the cloning, processing and/or expression of the gene product. For example, alterations may be introduced using techniques which are well known in the art, e.g., site-directed mutagenesis, to insert new restriction sites, to alter glycosylation patterns, to change codon preference, to produce splice variants, etc. For example, it may be advantageous to produce β-secretase-encoding nucleotide sequences possessing non-naturally occurring codons. Codons preferred by a particular prokaryotic or eukaryotic host (Murray, E. et al. (1989) Nuc Acids Res 17:477-508) can be selected, for example, to increase the rate of β-secretase polypeptide expression or to produce recombinant RNA transcripts having desirable properties, such as a longer half-life, than transcripts produced from naturally occurring sequence. This may be particularly useful in producing recombinant enzyme in non-mammalian cells, such as bacterial, yeast, or insect cells. The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells that are genetically engineered with vectors of the invention, and the production of proteins and polypeptides of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the β-secretase gene. The culture conditions, such as temperature, pH and the like, are those previously used with the host cell selected for expression, and will be apparent to those skilled in the art. Exemplary methods for transfection of various types of cells are provided in Example 6, herein.

As described above, according to a preferred embodiment of the invention, host cells can be co-transfected with an enzyme substrate, such as with APP (such as wild type or Swedish mutation form), in order to measure activity in a cell environment. Such host cells are of particular utility in the screening assays of the present invention, particularly for screening for therapeutic agents that are able to traverse cell membranes.

The polynucleotides of the present invention may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: CMV, LTR or SV40 promoter, the *E. coli* lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces*, and *Salmonella typhimurium*; fungal cells, such as yeast; insect cells such as *Drosophila* and *Spodoptera* Sf9; mammalian cells such as CHO, COS, BHK, HEK 293 or Bowes melanoma; adenoviruses; plant cells, etc. It is understood that not all cells or cell lines will be capable of producing fully functional β-secretase; for example, it is probable that human β-secretase is highly glycosylated in native form, and such glycosylation may be necessary for activity. In this event, eukaryotic host cells may be preferred. The selection of an appropriate host is deemed to be within the scope of those skilled in the art from the teachings herein. The invention is not limited by the host cells employed.

In bacterial systems, a number of expression vectors may be selected depending upon the use intended for β-secretase. For example, when large quantities of β-secretase or fragments thereof are needed for the induction of antibodies, vectors, which direct high level expression of fusion proteins that are readily purified, may be desirable. Such vectors include, but are not limited to, multifunctional *E. coli* cloning and expression vectors such as Bluescript(R) (Stratagene, La Jolla, Calif.), in which the β-secretase coding sequence may be ligated into the vector in-frame with sequences for the amino-terminal Met and the subsequent 7 residues of beta-galactosidase so that a hybrid protein is produced; pIN vectors (Van Heeke & Schuster (1989) J Biol Chem 264:5503-5509); pET vectors (Novagen, Madison Wis.); and the like.

In the yeast *Saccharomyces cerevisiae* a number of vectors containing constitutive or inducible promoters such as alpha factor, alcohol oxidase and PGH may be used. For reviews, see Ausubel et al. (supra) and Grant et al. (1987; Methods in Enzymology 153:516-544).

In cases where plant expression vectors are used, the expression of a sequence encoding β-secretase may be driven by any of a number of promoters. For example, viral promoters such as the 35S and 19S promoters of CaMV (Brisson et al. (1984) Nature 310:511-514) may be used alone or in combination with the omega leader sequence from TMV (Takamatsu et al. (1987) EMBO J. 6:307-311). Alternatively, plant promoters such as the small subunit of RUBISCO (Coruzzi et al (1984) EMBO J. 3:1671-1680; Broglie et al. (1984) Science 224:838-843); or heat shock promoters (Winter J and Sinibaldi R M (1991) Results. Probl. Cell Differ. 17:85-105) may be used. These constructs can be introduced into plant cells by direct DNA transformation or pathogen-mediated transfection. For reviews of such techniques, see Hobbs S or Murry L E (1992) in McGraw Hill Yearbook of Science and Technology, McGraw Hill, New York, N.Y., pp 191-196; or Weissbach and Weissbach (1988) Methods for Plant Molecular Biology, Academic Press, New York, N.Y., pp 421-463.

β-secretase may also be expressed in an insect system. In one such system, *Autographa californica* nuclear polyhedrosis virus (AcNPV) is used as a vector to express foreign genes in *Spodoptera frugiperda* Sf9 cells or in *Trichoplusia larvae*. The Kv-SL coding sequence is cloned into a nonessential region of the virus, such as the polyhedrin gene, and placed under control of the polyhedrin promoter. Successful insertion of Kv-SL coding sequence will render the polyhedrin gene inactive and produce recombinant virus lacking coat protein coat. The recombinant viruses are then used to infect *S. frugiperda* cells or *Trichoplusia larvae* in which β-secretase is expressed (Smith et al. (1983) J Virol 46:584; Engelhard E K et al. (1994) Proc Nat Acad Sci 91:3224-3227).

In mammalian host cells, a number of viral-based expression systems may be utilized. In cases where an adenovirus is used as an expression vector, a β-secretase coding sequence may be ligated into an adenovirus transcription/translation complex consisting of the late promoter and tripartite leader sequence. Insertion in a nonessential E1 or E3 region of the viral genome will result in a viable virus capable of expressing Kv-SL in infected host cells (Logan and Shenk (1984) Proc Natl Acad Sci 81:3655-3659). In addition, transcription enhancers, such as the rous sarcoma virus (RSV) enhancer, may be used to increase expression in mammalian host cells.

Specific initiation signals may also be required for efficient translation of a secretase coding sequence. These signals include the ATG initiation codon and adjacent sequences. In cases where β-secretase coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (ScharfD et al. (1994) Results Probl Cell Differ 20:125-62; Bittner et al. (1987) Methods in Enzymol 153:516-544).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology) or newer methods, including lipid transfection with "FUGENE" (Roche Molecular Biochemicals, Indianapolis, Ind.) or "EFFECTENE" (Quiagen, Valencia, Calif.), or other DNA carrier molecules. Cell-free translation systems can also be employed to produce polypeptides using RNAs derived from the DNA constructs of the present invention. Kv-SL mRNA or cRNA may also be microinjected into, e.g. *Xenopus laevis* oocytes, for production of Kv-SL for electrophysiological measurements or other assays.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "prepro" form of the protein may also be important for correct insertion, folding and/or function. For example, in the case of β-secretase, it is likely that the N-terminus of SEQ ID NO: 2 is truncated, possibly at amino acid 46, or at about residues 57-58 of SEQ ID NO: 2. Different host cells such as CHO, HeLa, BHK, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression may be preferred. For example, cell lines that stably express β-secretase may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clumps of stably transformed cells can be proliferated using tissue culture techniques appropriate to the cell type.

Host cells transformed with a nucleotide sequence encoding β-secretase may be cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding β-secretase can be designed with signal sequences which direct secretion of β-secretase polypeptide through a prokaryotic or eukaryotic cell membrane.

β-secretase may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and β-secretase is useful to facilitate purification. One such expression vector provides for expression of a fusion protein comprising β-secretase (e.g., a soluble β-secretase fragment) fused to a polyhistidine region separated by an enterokinase cleavage site. The histidine residues facilitate purification on IMIAC (immobilized metal ion affinity chromatography, as described in Porath et al. (1992) Protein Expression and Purification 3:263-281) while the enterokinase cleavage site provides a means for isolating Kv-SL from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

β-secretase can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. For example, affinity matrices employing molecules directed to the active site(s) of β-secretase, such as high affinity substrate inhibitors identified according to the methods described below, exemplified by P10-P4'staD→V may be used to purify the enzyme. Protein refolding steps can be used, as necessary, in completing configuration of the mature protein. Exemplary methods for purifying naturally occurring as well as purified forms of β-secretase are provided in the Examples.

B. Methods of Selecting β-Secretase Inhibitors

The present invention also includes methods for identifying molecules, such as synthetic drugs, antibodies, peptides, or other molecules, which have an inhibitory effect on the activity of β-secretase described herein, generally referred to as inhibitors, antagonists or blockers of the enzyme. Such an assay includes the steps of providing a human β-secretase, such as the β-secretase which comprises SEQ ID NO: 2, contacting the β-secretase with a test compound to determine whether it has a modulating effect on the activity of the enzyme, as discussed below, and selecting from test compounds capable of modulating β-secretase activity. In particular, inhibitory compounds (antagonists) are useful in the treatment of disease conditions associated with amyloid deposition, particularly Alzheimer's disease.

Particularly useful screening assays employ cells which express both β-secretase and APP. Such cells can be made recombinantly by co-transfection of the cells with polynucleotides encoding the proteins, as described in Section III, above, or can be made by transfecting a cell which naturally contains one of the proteins with the second protein. In a particular embodiment, such cells are grown up in multi-well culture dishes and are exposed to varying concentrations of a test compound or compounds for a pre-determined period of time, which can be determined empirically. Whole cell lysates, cultured media or cell membranes are assayed for β-secretase activity. Test compounds which significantly inhibit activity compared to control (as discussed below) are considered therapeutic candidates.

Isolated β-secretase, its ligand-binding, catalytic, or immunogenic fragments, or oligopeptides thereof, can be used for screening therapeutic compounds in any of a variety of drug screening techniques. The protein employed in such a test may be membrane-bound, free in solution, affixed to a solid support, borne on a cell surface, or located intracellularly. The formation of binding complexes between β-secretase and the agent being tested can be measured. Compounds that inhibit binding between β-secretase and its substrates, such as APP or APP fragments, may be detected in such an assay. Preferably, enzymatic activity will be monitored, and candidate compounds will be selected on the basis of ability to inhibit such activity. More specifically, a test compound will be considered as an inhibitor of β-secretase if the measured β-secretase activity is significantly lower than β-secretase activity measured in the absence of test compound. In this context, the term "significantly lower" means that in the presence of the test compound the enzyme displays an enzymatic activity which, when compared to enzymatic activity measured in the absence of test compound, is measurably lower, within the confidence limits of the assay method. Such measurements can be assessed by a change in $K_m$, and/or $V_{max}$, single assay endpoint analysis, or any other method standard in the art. Exemplary methods for assaying β-secretase are provided in Example 4 herein.

For example, in studies carried out in support of the present invention, compounds were selected based on their ability to inhibit β-secretase activity in the MBP-C125 assay. Compounds that inhibited the enzyme activity at a concentration lower than about 50 μM were selected for further screening.

The groups of compounds that show promise as candidates for inhibitor activity comprise a further aspect of the present invention. Initially 18 amino acid containing peptide strands were tested for binding and enzymatic cleavage by measuring the kinetics of the reaction. Plots of the rates of enzyme binding and turnover allowed determination of Km and Kcat for the enzyme with various inhibitor molecules. $K_m$, is a binding constant for enzyme (E) and substrate (S) to form the bound complex of enzyme and substrate ([ES]) and $K_{cat}$ is a catalytic constant for conversion of ES to E and P, where P is the product of the enzymatic reaction (in this case, cleaved peptide). The equilibrium reaction pathway is represented schematically as:

$$E + S \underset{K_m}{\Longleftrightarrow} [ES] \underset{K_{cat}}{\Longleftrightarrow} E + P$$

Since it was known that β-secretase cleaves the Swedish mutation of APP at the double substitution sites containing Asn-Leu instead of the Lys-Met of wild type APP, preliminary studies were made by substituting amino acids at the P1 and P1' sites. The Asn and Leu are labeled P1 and P1' respectively indicating that the peptide chain is cleavee between these two amino acids. The P numbers then increase arithmetically as one progressively counts the amino acids of the chain in either direction from this point. The prime following a P number indicates that one is moving in the carboxy terminal direction of the peptide chain.

It was found that the P1 site is quite sensitive to substitution for binding with only Leu (the Swedish mutation substitution) and Phe showing appreciable cleavage (30%). Next P1 was allowed to remain as Leu and P1' was varied by substitution with different amino acids. Interestingly, when P1' was varied there was quite a range of enzyme activity but when P1' was valine, the reaction kinetics showed that the enzyme became fully saturated. Thus this valine variant had good binding affinity for the protein as well as slowing the rate of cleavage of the bound complex. An IC50 value of the 18 residue sequence in an MBP M125 assay was measured as 3 μM, which indicated an enzyme inhibition of over 100 times that of the Swedish sequence. This result demonstrated a clear effect on enzyme turnover. As a result, valine was selected as the amino acid substitution at P1' with further variation of P1 and more remote binding sides to be studied. When statine a non-standard amino acid known to inhibit renin, another aspartyl protease, was substituted at P1 with P1' being valine, a potent inhibitor of β-secretase was created. The P10-P4'sta D→V inhibitor discussed above also incorporates this P1-Pi' sequence and is about 100 times more potent an inhibitor than the valine substitution alone.

Heptameric peptides were then attempted as inhibitors, such a chain length being selected because it was believed that the enzyme would require the next two or three amino acids on either side of the Sta-Val sequence to also fit the binding pockets of the enzyme. A variety of heptameric peptides were synthesized to probe the steric preferences of the enzyme active site for binding.

The substrates for these studies were synthesized using solid support sequential synthesis as described in Example 7. Assays of the inhibitory activity were performed in the MBP C125 assays described in Example 4 and IC50 values were generated for the heptameric inhibitors are reported in Table 9. Preferred inhibitors of the invention are those compounds in Group III, particularly preferred inhibitors are in Group II and the most preferred are the inhibitors of Group I.

Based on studies carried out in support of the invention, it has been determined that the peptide compound described herein as P10-P4'staD→V is a quite potent inhibitor of the enzyme. Further studies based on this sequence and peptidomimetics of portions of this sequence have revealed a number of small molecule inhibitors, such as the heptamer sequeces detailed in Example 7, which also show good affinity and inhibition of β-secretase. Other exemplary inhibitors are described, for example, in co-owned U.S. Provisional patent application entitled "Tetrapeptide Inhibitors of β-secretase," by inventors Varghese John, et al., which was co-filed as a provisional application is incorporated herein by reference.

Methods of making the hydroxyethylene core are know in the art and one such synthetic scheme is provided by Scheme I: Hydroxyethylene as used herein refers to the end product of Scheme 1 but having a free hydroxy group rather than the depicted silylated hydroxyl. The hydroxyethylene moiety may be used similarly to an amino acid in sequential peptide synteses.

DEFINITIONS OF STANDARD CHEMICAL ABBREVIATIONS

Ac=acetyl (methylcarbonyl)

Boc=tert-butoxycarbonyl

Scheme I

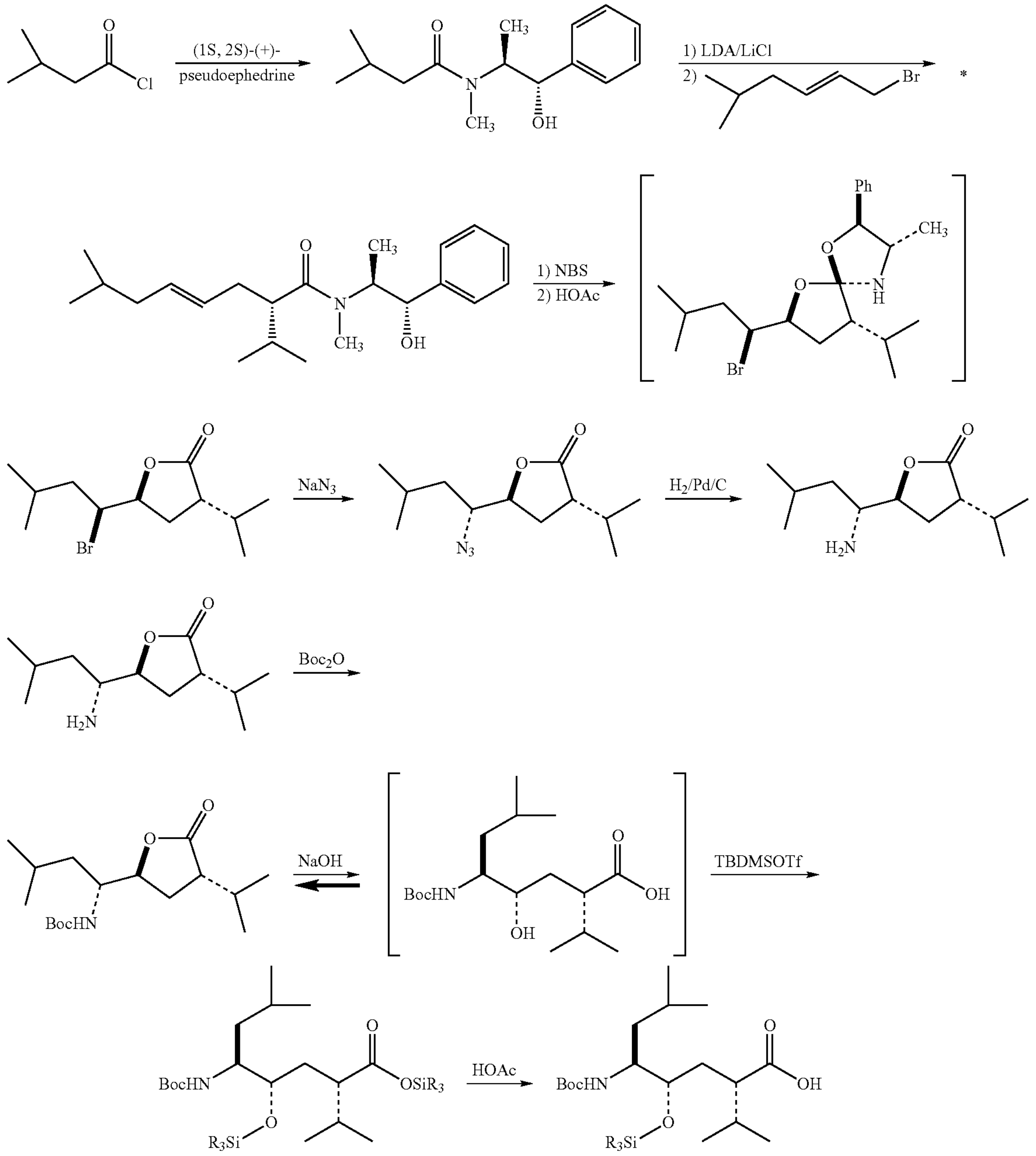

*Procedure for preparation of 1-bromo-5-methylhex-2-ene:

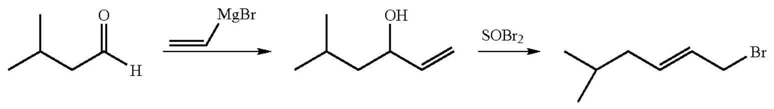

BOP=benzotriazol-1-yloxy-tris(dimethylamino)phosphonium hexafluorophosphate

CBZ=benzyloxycarbonyl

CDI=1,1'-carbonyldiimidazole

DCM dichloromethane=methylene chloride=$CH_2Cl_2$

EDC=ethyl-1-(3-dimethylaminopropyl)carbodiimide or 1-(3-dimethylaminopropyl)-3-ethylcarbodiimide hydrochloride HOBT=1-hydroxybenzotriazole $IC_{50}$=inhibitory concentration of a compound that reduces enzyme activity by half.

iso=an alkyl chain having the ending group. 2-methylpropyl, i.e. —$CH(CH_3)_2$.

LDA=lithium diisopropyl amide

MeOH=methanol n=normal, i.e. unbranched, e.g. n-Pr is —$CH_2$—$CH_2$-$CH_3$

NBS=N-bromosuccinimide

PEPC=1-(3-(1-pyrrolidinyl)propyl)-3-ethylcarbodiimide $R_f$=ratio of movement of a substance on a thin layer chromatogram in comparison to the movement of the solvent front.

t or tert=tertiary in an alkyl chain, e.g. t-butyl is —$C(CH_3)_3$.

TBDMSCl=t-butyl-dimethylsilyl chloride

TBDMSOTf=t-butyl-dimethylsilyl trifluorosulfonic acid ester

TEA=triethylacetate

TFA=trifluoroacetic acid

THF=tetrahydrofuran

TLC=thin layer chromatography

Removal of a Boc-Protecting Group from a Protected Amine to Generate Free Amine:

For example, the Boc-protected hydroxyethylene product of Scheme I was dissolved in a trifluoroacetic acid/dichloromethane (1/1) solution. The reaction was monitored by TLC to confirm the consumption of starting material at which time the solvents were removed under reduced pressure to yield the free amine, which was used without further purification. In a similar fashion, substituting a Boc-protected amino acid or statine will yield the free amine which may be utilized in the next step directly below.

Coupling a Deprotected Amine with a Selected Amino Acid Residue ($AA_1$).

Boc-$AA_1$-OH (1.0 equiv.) is dissolved in 30 mL of dry dichloromethane, then HOBT (2.0 equiv.), and the hydroxyethylene or another amino acid (1.0 equiv.) and TEA (5 equiv.) are added and all stirred for 20 minutes. EDC (1.2 equiv.) is added and the mixture is stirred overnight under an atmosphere of nitrogen. The reaction is then diluted with water and extracted with EtOAc (3×). The organic layers are washed with aqueous citric acid (2×), sat. $NaHCO_3$ (2×), brine, then dried over $MgSO_4$. Removal of a Boc-protecting group from the resulting polypeptide is accomplished as described in the procedure above.

Removal of the Carboxybenzyl (Cbz) Protecting Group to Form a C-Terminal Acid

PP-$AA_2$-$AA_1$-OBz (1.2 g) is dissolved in 100 ml of MeOH and Pd/C (1 g, 10%) is added. The reaction is subjected to a hydrogen gas atmosphere of 50 psi for 2 hours. The resulting slurry is filtered through a pad of celite, and roto-evaporated to yield the desired material.

The silyl protecting group on the hydroxyl function of the hydroxyethylene may be removed after the peptide bonds are completed and my be performed, for example, by treatment of the compound with hydrogen fluoride in DCM.

Polypeptides are constructed by sequential addition of amino acids, usually from the C-terminal amino acid to the N-terminus. The C-terminus is either protected, as by a carbobenzyl group, or linked to a solid support for sequential synthesis which may be cleaved once the desired peptide sequence has been formed.

Random libraries of peptides or other compounds can also be screened for suitability as β-secretase inhibitors. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes).

A preferred source of test compounds for use in screening for therapeutics or therapeutic leads is a phage display library. See, e.g., Devlin, WO 91/18980; Key, B. K., et al., eds., Phage Display of Peptides and Proteins, A Laboratory Manual, Academic Press, San Diego, Calif., 1996. Phage display is a powerful technology that allows one to use phage genetics to select and amplify peptides or proteins of desired characteristics from libraries containing $10^8$-$10^9$ different sequences. Libraries can be designed for selected variegation of an amino acid sequence at desired positions, allowing bias of the library toward desired characteristics. Libraries are designed so that peptides are expressed fused to proteins that are displayed on the surface of the bacteriophage. The phage displaying peptides of the desired characteristics are selected and can be regrown for expansion. Since the peptides are amplified by propagation of the phage, the DNA from the selected phage can be readily sequenced facilitating rapid analyses of the selected peptides.

Phage encoding peptide inhibitors can be selected by selecting for phage that bind specifically to β-secretase protein. Libraries are generated fused to proteins such as gene II that are expressed on the surface of the phage. The libraries can be composed of peptides of various lengths, linear or constrained by the inclusion of two Cys amino acids, fused to the phage protein or may also be fused to additional proteins as a scaffold. One may start with libraries composed of random amino acids or with libraries that are biased to sequences in the βAPP substrate surrounding the β-secretase cleavage site. One may also design libraries biased toward the peptidic inhibitors and substrates described herein or biased toward peptide sequences obtained from the selection of binding phage from the initial libraries.

The β-secretase is immobilized and phage specifically binding to the β-secretase selected for. One may include a requirement that the phage not bind in the presence of a known active site inhibitor of β-secretase (e.g. the inhibitors described herein), to further direct the phage to specifically binding in the active site. Highly purified β-secretase, derived from brain or preferably from recombinant cells can be immobilized to 96 well plastic dishes using standard techniques (reference phage book). Recombinant β-secretase, designed to be fused to a peptide that can bind (e.g. strepaviden binding motifs, His, FLAG or myc tags) to another protein immobilized (such as stripaviden or appropriate antibodies) on the plastic petri dishes can also be used. Phage are incubated with the bound β-secretase and unbound phage removed by washing. The phage are eluted and this selection is repeated until a population of phage binding to β-secretase is recovered. Binding and elution are done using standard techniques.

Alternatively β-secretase can be "bound" by expressing it in Cos or other mammalian cells growing on a petri dish. In this case one would select for phage binding to the β-secretase expressing cells, and select against phage that bind to the control cells, that are not expressing β-secretase.

One can also use phage display technology to select for preferred substrates of 1-secretase, and incorporate the identified features of the preferred substrate peptides obtained by phage display into inhibitors.

In the case of β-secretase, knowledge of the amino acid sequence surrounding the cleavage site of APP and of the cleavage site of APPsw has provided information for purposes of setting up the phage display screening library to identify preferred substrates of β-secretase. Additionally, knowledge of the sequence of a particularly good peptide inhibitor, P10-P4staD→V, as described herein, provides information for setting up a "biased" library toward this sequence.

For example, the peptide substrate library containing $10^8$ different sequences is fused to a protein (such as a gene III protein) expressed on the surface of the phage and a sequence that can be used for binding to streptavidin, or another protein, such as His tag and antibody to His. The phage are digested with protease, and undigested phage are removed by binding to appropriate immobilized binding protein, such as streptavidin. This selection is repeated until a population of phage encoding substrate peptide sequences is recovered. The DNA in the phage is sequenced to yield the substrate sequences. These substrates are then used for further development of peptidomimetics, particularly peptidomimetics having inhibitory properties.

Combinatorial libraries and other compounds are initially screened for suitability by determining their capacity to bind to, or preferably, to inhibit β-secretase activity in any of the assays described herein or otherwise known in the art. Compounds identified by such screens are then further analyzed for potency in such assays. Inhibitor compounds can then be tested for prophylactic and therapeutic efficacy in transgenic animals predisposed to an amyloidogenic disease, such as mice bearing a 717 mutation of APP (PDAPP mice) described by Games et al., Nature 373: 523-527, 1995 and Wadsworth et al. U.S. Pat. No. 5,811,633, U.S. Pat. No. 5,604,131, U.S. Pat. No. 5,720,936, and mice bearing a Swedish mutation of APP such as described by McConlogue et al., U.S. Pat. No. 5,612,486 and Hsiao et al., U.S. Pat. No. 5,877,399; Staufenbiel et al., *Proc. Natl. Acad. Sci. USA* 94, 13287-13292 (1997); Sturchler-Pierrat et al., *Proc. Natl. Acad. Sci. USA* 94, 13287-13292 (1997); Borchelt et al., *Neuron* 19, 939-945 (1997)), all of which are incorporated herein by reference.

Compounds or agents found to be efficacious and safe in such animal models will be moved into human clinical trials for treatment of Alzheimer's disease and related diseases. The same screening approach can be used on other potential agents such as peptidomimetics described above.

In general, in selecting therapeutic compounds based on the foregoing assays, it is useful to determine whether the test compound has an acceptable toxicity profile, e.g., in a variety of in vitro cells and animal model(s). It may also be useful to search the tested and identified compound(s) against existing compound databases to determine whether the compound or analogs thereof have been previously employed for pharmaceutical purposes, and if so, optimal routes of administration and dose ranges. Alternatively, routes of administration and dosage ranges can be determined empirically, using methods well known in the art (see, e.g., Benet, L. Z., et al. Pharmacokinetics in *Goodman & Gilman's The Pharmacological Basis of Therapeutics*, Ninth Edition, Hardman, J. G., et al., Eds., McGraw-Hill, New York, 1966) applied to standard animal models, such as the transgenic PDAPP animal model (e.g., Games, D., et al. Nature 373: 523-527, 1995; Johnson-Wood, K., et al., Proc. Natl. Acad. Sci. USA 94: 1550-1555, 1997). To optimize compound activity and/or specificity, it may be desirable to construct a library of near-neighbor analogs to search for analogs with greater specificity, and/or activity. Methods for synthesizing near-neighbor and/or targeted compound libraries are well-known in the combinatorial library field.

C. Inhibitors and Therapeutics

Part B, above, describes method of screening for compounds having β-secretase inhibitory activity. To summarize, guidance is provided for specific methods of screening for potent and selective inhibitors of β-secretase enzyme. Significantly, the practitioner is directed to a specific peptide substrate/inhibitor sequences, such as P10-P4'staD→V, on which drug design can be based and additional sources, such as biased phage display libraries, that should provide additional lead compounds.

The practitioner is also provided ample guidance for further refinement of the binding site of the enzyme, for example, by crystallizing the purified enzyme in accord with the methods provide herein. Noting the success in this area that has been enjoyed in the area of HIV protease inhibitor development, it is contemplated that such efforts will lead to further optimization of test compounds. With optimized compounds in hand, it is possible to define a compound pharmacophore, and further search existing pharmacophore databases, e.g., as provided by Tripos, to identify other compounds that may differ in 2-D structural formulae with the originally discovered compounds, but which share a common pharmacophore structure and activity. Test compounds are assayed in any of the inhibitor assays described herein, at various stages in development.

Therefore, the present invention includes β-secretase inhibitory agents discovered by any of the methods described herein, particularly the inhibitor assays and the crystallization/optimization protocols. Such inhibitory agents are therapeutic candidates for treatment of Alzheimer's disease, as well as other amyloidoses characterized by Aβ peptide deposition. The considerations concerning therapeutic index (toxicology), bioavailability and dosage discussed in Part B above are equally important to consider with respect to these therapeutic candidates.

D. Methods of Diagnosis

The present invention also provides methods of diagnosing individuals who carry mutations that provide enhanced β-secretase activity. For example, there are forms of familial Alzheimer's disease in which the underlying genetic disorder has yet to be recognized. Members of families possessing this genetic predisposition can be monitored for alterations in the nucleotide sequence that encodes β-secretase and/or promoter regions thereof, since it is apparent, in view of the teachings herein, that individuals who overexpress of the enzyme or possess catalytically more efficient forms of the enzyme would be likely to produce relatively more Aβ peptide. Support for this supposition is provided by the observation, reported herein, that the amount of β-secretase enzyme is rate limiting for production of Aβ in cells.

More specifically, persons suspected to have a predilection for developing for developing or who already have the disease, as well as members of the general population, may be screened by obtaining a sample of their cells, which may be blood cells or fibroblasts, for example, and testing the samples for the presence of genetic mutations in the β-secretase gene, in comparison to SEQ ID NO: 1 described herein, for example. Alternatively or in addition, cells from such individuals can be tested for β-secretase activity. According to this embodiment, a particular enzyme preparation might be tested for increased affinity and/or Vmax with respect to a β-secretase substrate such as MBP-C125, as described herein, with comparisons made to the normal range of values measured in the general population. Individuals whose β-secretase activity is increased compared to normal values are susceptible to developing Alzheimer's disease or other amyloidogenic diseases involving deposition of Aβ peptide.

E. Therapeutic Animal Models

A further utility of the present invention is in creation of certain transgenic and/or knockout animals that are also useful in the screening assays described herein. Of particular use is a transgenic animal that overexpresses the β-secretase enzyme, such as by adding an additional copy of the mouse enzyme or by adding the human enzyme. Such an animal can be made according to methods well known in the art (e.g., Cordell, U.S. Pat. No. 5,387,742; Wadsworth et al., U.S. Pat. No. 5,811,633, U.S. Pat. No. 5,604,131, U.S. Pat. No. 5,720,936; McConlogue et al., U.S. Pat. No. 5,612,486; Hsiao et al., U.S. Pat. No. 5,877,399; and "Manipulating the Mouse Embryo, A Laboratory Manual," B. Hogan, F. Costantini and E. Lacy, Cold Spring Harbor Press, 1986)), substituting the one or more of the constructs described with respect to β-secretase, herein, for the APP constructs described in the foregoing references, all of which are incorporated by reference.

An overexpressing β-secretase transgenic mouse will make higher levels of Aβ and sβAPP from APP substrates than a mouse expressing endogenous β-secretase. This would facilitate analysis of APP processing and inhibition of that processing by candidate therapeutic agents. The enhanced production of Aβ peptide in mice transgenic for β-secretase would allow acceleration of AD-like pathology seen in APP transgenic mice. This result can be achieved by either crossing the β-secretase expressing mouse onto a mouse displaying AD-like pathology (such as the PDAPP or Hsiao mouse) or by creating a transgenic mouse expressing both the β-secretase and APP transgene.

Such transgenic animals are used to screen for β-secretase inhibitors, with the advantage that they will test the ability of such inhibitors to gain entrance to the brain and to effect inhibition in vivo.

Another animal model contemplated by the present invention is a so-called "knock-out mouse" in which the endogenous enzyme is either permanently (as described in U.S. Pat. Nos. 5,464,764, 5,627,059 and 5,631,153, which are incorporated by reference in their entity) or inducibly deleted (as described in U.S. Pat. Nos. 4,959,317, which is incorporated by reference in its entity). Such mice serve as controls for β-secretase activity and/or can be crossed with APP mutant mice, to provide validation of the pathological sequelae. Such mice can also provide a screen for other drug targets, such as drugs specifically directed at Aβ deposition events.

β-secreatase knockout mice provide a model of the potential effects of β-secretase inhibitors in vivo. Comparison of the effects of β-secretase test inhibitors in vivo to the phenotype of the β-secretase knockout can help guide drug development. For example, the phenotype may or may not include pathologies seen during drug testing of β-secretase inhibitors. If the knockout does not show pathologies seen in the drug-treated mice, one would know that the drug is interacting non-specifically with another target in addition to the β-secretase target. One could use tissue from the knockout to set up drug binding assays or to do expression cloning to find the targets that are responsible for these toxic effects, and then use this information to design further drugs that do not interact with these undesirable targets. This may be difficult to do in wildtype mice that express β-secretase. The knockout mice will facilitate analyses of potential toxicities that are inherent to β-secretase inhibition. Knowledge of potential toxicities could help guide one to design drugs or drug-delivery systems to reduce such toxicities. The inducible knockout mice would be particularly useful in distinguishing toxicity in an adult animal vs embryonic effects seen in the standard knockout. If there are fetal-lethal effects the inducible knockout may be the only way to get viable knockout mice.

Methods and technology for developing knock-out mice have matured to the point that a number of commercial enterprises generate such mice on a contract basis (e.g., Lexicon Genetics, Woodland Tex.; Cell & Molecular Technologies, Lavallette, N.J.; Crysalis, DNX Transgenic Sciences, Princeton, N.J.). Methodologies are also available in the art. (See Galli-Taliadoros, L. A., et al., J. Immunol. Meth. 181: 1-15, 1995. Briefly, a genomic clone of the enzyme of interest is required. Where, as in the present invention, the exons encoding the regions of the protein have been defined, it is possible to achieve inactivation without further knowledge of the regulatory sequences controlling transcription. Specifically, the mouse gene sequence is provided herein, a mouse strain 129 genomic library can be screened by hybridization or PCR, using the sequence information provided herein, according to methods well known in the art. (Ausubel; Sambrook) The genomic clone so selected is then subjected to restriction mapping and partial exonic sequencing for confirmation of mouse homologue and to obtain information for knock-out vector construction. Appropriate regions are then sub-cloned into a "knock-out" vector carrying a selectable marker, such as a vector carrying a $neo^r$ cassette, which renders cells resistant to aminoglycoside antibiotics such as gentamycin. The construct is further engineered for disruption of the gene of interest, such as by insertion of a sequence replacement vector, in which a selectable marker is inserted into an exon of the gene, where it serves as a mutagen, disrupting the coordinated transcription of the gene. Vectors are then engineered for transfection into embryonic stem (ES) cells, and appropriate colonies are isolated. Positive ES cell clones are micro-injected into isolated host blastocysts to generate chimeric animals, which are then bred and screened for germline transmission of the mutant allele.

According to a further preferred embodiment, such β-secretase knock-out mice can be generated such that the mutation is inducible, such as by inserting in the knock-out mice a lox region flanking the β-secretase gene region. Such mice are then crossed with mice bearing a "Cre" gene under an inducible promoter, resulting in at least some off-spring bearing both the "Cre" and the lox constructs. When expression of "Cre" is induced, it serves to disrupt the gene flanked by the lox constructs. Such a "Cre-lox" mouse is particularly useful, when it is suspected that the knock-out mutation may be lethal. In addition, it provides the opportunity for knocking out the gene in selected tissues, such as the brain. Methods for generating Cre-lox constructs are provided by U.S. Pat. No. 4,959,317, incorporated herein by reference.

The following examples illustrate, but in no way are intended to limit the present invention.

EXAMPLE 1

Isolation of Coding Sequences for Human β-secretase

A. PCR Cloning

Poly A+ RNA from IMR human neuroblastoma cells was reverse transcribed using the Perkin-Elmer kit. Eight degenerate primer pools, each 8 fold degenerate, encoding the N and C terminal portions of the amino acid sequence obtained from the purified protein were designed (shown in Table 6; oligos 3407 through 3422). PCR reactions were composed of cDNA from 10 ng of RNA, 1.5 mM $MgCl_2$, 0.125 μl AmpliTaq® Gold, 160 μM each dNTP (plus 20 μM additional from the reverse transcriptase reaction), Perkin-Elmer TAQ buffer (from AmpliTaq® Gold kit, Perkin-Elmer, Foster City, Calif.), in a 25 μl reaction volume. Each of oligonucleotide primers 3407 through 3414 was used in combination with each of oligos 3415 through 3422 for a total for 64 reactions. Reactions were run on the Perkin-Elmer 7700 Sequence Detection machine under the following conditions: 10 min at 95° C., 4 cycles of, 45° C. annealing for 15 second, 72° C. extension for 45 second and 95° C. denaturation for 15 seconds followed by 35 cycles under the same conditions with the exception that the annealing temperature was raised to 55° C. (The foregoing conditions are referred to herein as "Reaction 1 conditions.") PCR products were visualized on 4% agarose gel (Northern blots) and a prominent band of the expected size (68 bp) was seen in reactions, particularly with the primers 3515-3518 in many of the lanes (each of FIGS. 3A-3C shows two gels, an upper and a lower gel, and the reaction combinations were run sequentially in the gels as illustrated, such that primer 3515 was reacted with each of 3507-3514, followed by reaction of primer 3516 with each of primers 3507-3514, and so forth). The 68 kb band was sequenced and the internal region coded for the expected amino acid sequence. This gave the exact DNA sequence for 22 bp of the internal region of this fragment. C.GGC.CG-G.AGG.GGC.AGC.TTT.GTG (SEQ ID NO:101)

Additional sequence was deduced from the efficiency of various primer pools of discrete sequence in generating this PCR product. Primer pools 3419 to 3422 gave very poor or no product, whereas pools 3415 to 3418 gave robust signal. The difference between these pools is a CTC (3415 to 3418) vs TTC (3419 to 3422) in the 3' most end of the pools. Since CTC primed more efficiently we can conclude that the reverse complement GAG is the correct codon. Since Met coding is unique we can also conclude that the following codon is ATG. Thus the exact DNA sequence obtained is:

.CCC.GGC.CGG.AGG.GGC.AGC.TTT.GTG.
GAG.ATG.GT (SEQ ID NO: 49)

encoding the amino acid sequence P G R R G S F V E M V (SEQ ID NO: 50). This sequence can be used to design exact oligonucleotides for 3 and 5' RACE PCR on either cDNA or libraries or to design specific hybridization probes to be used to screen libraries.

Since the degenerate PCR product was found to be so robust, this reaction may also be used as a diagnostic for the presence of clones containing this sequence. Pools of libraries can be screened using this PCR product to indicate the presence of a clone in the pool. The pools can be broken out to identify individual clones. Screening pools of known complexity and or size can provide information on the abundance of this clone in a library or source and can approximate the size of the full length clone or message.

For generation of a probe, PCR reactions using oligonucleotides 3458 and 3469 or 3458 and 3468 (Table 7) can be carried out using the 23 RACE product, clone 9C7E.35 (30 ng, clone 9C7E.35 was isolated from origene library, see Example 2), or cDNA generated from brain, using the standard PCR conditions (Perkin-Elmer rtPCR and amplitaqgold kits) with the following: 25 μl reaction volume 1.5 mM $MgCl_2$, 0.125 μl of AmpliTaq® Gold (Perkin-Elmer), initial 950 for 10 min to activate the AmpliTaq® Gold, 36 cycles of 65° 15 sec 72° 45 sec 95° for 15 sec, followed by 3 min at 72°. Product was purified on a Quiagen PCR purification kit and used as a substrate for random priming to generate a radiolabelled probe (Sambrook, et al., supra; Amersham RediPrime® kit). This probe was used to isolate full length close pCEK clone 27 shown in FIGS. 12 and 13.

Derivation of Full Length Clone pCEK Clone 27

A human primary neuronal cell library in the mammalian expression vector pCEK2 vector was generated using size selected cDNA, and pools of clones generated from different sized inserts. The cDNA library for β-secretase screening was made with poly(A)$^+$ RNA isolated from primary human neuronal cells. The cloning vector was pCEK2 (map shown below).

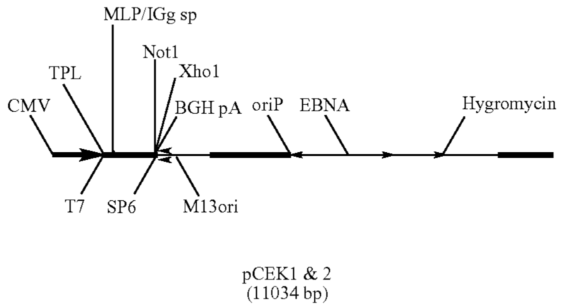

pCEK2

We synthesized the double-stranded cDNA inserts using the cDNA Synthesis Kit from Stratagene with some modifications. The inserts were then fractionated according to their sizes. A total of five fractions were individually ligated with double-cut (NotI and XhoI) pCEK2 and subsequently transformed into the *E. Coli* strain XL-10 Gold which is designed to accept very large plasmids.

The fractions of transformed *E. Coli* were plated on Terrific Broth agar plates containing ampicilin and let grown for 18 hours. Each fraction yielded about 200,000 colonies to give a total of one million colonies. The colonies were then scraped from the plates and plasmids isolated from them in pools of approximately 70,000 clones/pool. 70,000 clones from each pool of the library was screened for the presence of the putative β-secretase gene using the diagnostic PCR reaction (degenerate primers 3411 and 3417 shown above).

Clones from the 1.5 kb pool were screened using a radiolabeled probe generated from a 390b.p. PCR product generated from clone 9C7E.35. For generation of a probe, PCR product was generated using 3458 and 3468 as primers and clone 9C7E.35 (30 ng) as substrate.

```
                                        (SEQ ID NO:20)
3468: CAG.CAT.AGG.CCA.GCC.CCA.GGA.TGC.CT

                                        (SEQ ID NO:19)
3458: GAG GGG CAG CTT TGT GGA GA
```

PCR product was used as a substrate for random priming to generate a radiolabeled probe. 180,000 clones from the 1.5 kb pool (70,000 original clones in this pool), were screened by hybridization with the PCR probe and 9 positive clones identified. Four of these clones were isolated and by restriction mapping these appear to encode two independent clones of 4 to 5 kb (clone 27) and 6 to 7 kb (clone 53) length. Sequencing of clone 27 verified that it contains a coding region of 1.5 kb. See FIG. 13 for sequence of pCEK clone27 (clone 27).

TABLE 6

| SEQ ID NO. | Pool No. | Nucleotide Sequence (Degenerate substitutions are shown in parentheses) |
|---|---|---|
| 3 | 3407 | G.AGA.GAC.GA(GA).GA(GA).CC(AT).GAG.GAG.CC |
| 4 | 3408 | G.AGA.GAC.GA(GA).GA(GA).CC(AT).GAA.GAG.CC |
| 5 | 3409 | G.AGA.GAC.GA(GA).GA(GA).CC(AT).GAA.GAA.CC |
| 6 | 3410 | G.AGA.GAC.GA(GA).GA(GA).CC(AT).GAG.GAA.CC |
| 7 | 3411 | AGA.GAC.GA(GA).GA(GA).CC(CG).GAG.GAG.CC |
| 8 | 3412 | AGA.GAC.GA(GA).GA(GA).CC(CG).GAA.GAG.CC |
| 9 | 3413 | AGA.GAC.GA(GA).GA(GA).CC(CG).GAA.GAA.CC |
| 10 | 3414 | AGA.GAC.GA(GA).GA(GA).CC(CG).GAG.GAA.CC |
| 11 | 3415 | CG.TCA.CAG.(GA)TT.(GA)TC.AAC.CAT.CTC |
| 12 | 3416 | CG.TCA.CAG.(GA)TT.(GA)TC.TAC.CAT.CTC |
| 13 | 3417 | CG.TCA.CAG.(GA)TT.(GA)TC.CAC.CAT.CTC |
| 14 | 3418 | CG.TCA.CAG.(GA)TT.(GA)TC.GAC.CAT.CTC |
| 15 | 3419 | CG.TCA.CAG.(GA)TT.(GA)TC.AAC.CAT.TTC |
| 16 | 3420 | CG.TCA.CAG.(GA)TT.(GA)TC.TAC.CAT.TTC |
| 17 | 3421 | CG.TCA.CAG.(GA)TT.(GA)TC.CAC.CAT.TTC |
| 18 | 3422 | CG.TCA.CAG.(GA)TT.(GA)TC.GAC.CAT.TTC |

TABLE 7

| SEQ ID NO. | Pool No. | Nucleotide Sequence |
|---|---|---|
| 19 | 3458 | GAG GGG CAG CTT TGT GGA GA |
| 20 | 3468 | CAG.CAT.AGG.CCA.GCC.CCA.GGA.TGC.CT |
| 21 | 3469 | GTG.ATG.GCA.GCA.ATG.TTG.GCA.CGC |

EXAMPLE 2

Screening of Human Fetal Brain cDNA Library

The Origene human fetal brain Rapid-Screen™ cDNA Library Panel is provided as a 96-well format array consisting of 5000 clones (plasmid DNA) per well from a human fetal brain library. Subplates are available for each well consisting of 96 wells of 50 clones each in *E. coli*. This is an oligo-dT primed library, size-selected and unidirectionally inserted into the vector pCMV-XL3.

94 wells from the master plate were screened using PCR. The Reaction 1 Conditions described in Example 1, above, were followed, using only primers 3407 and 3416 with 30 ng of plasmid DNA from each well. Two pools showed the positive 70 bp band. The same primers and conditions were used to screen 1 μl *E. coli* from each well of one of the subplates. *E. coli* from the single positive well was then plated onto LB/amp plates and single colonies screened using the same PCR conditions. The positive clone, about 1 Kb in size, was labeled 9C7E.35. It contained the original peptide sequence as well as 5' sequence that included a methionine. The 3' sequence did not contain a stop codon, suggesting that this was not a full-length clone, consistent with Northern blot data.

EXAMPLE 3

PCR Cloning Methods

Figure 4:
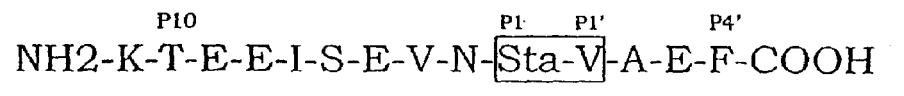

FIG. 4 shows a schematic diagram of the specific 3'RACE strategy used in experiments carried out in support of the present invention and effective to elucidate the polynucleotide encoding human β-secretase. Methods and conditions appropriate for replicating the experiments described herein and/or determining polynucleotide sequences encoding additional members of the novel family of aspartyl proteases described herein may be found, for example, in White, B. A., ed., PCR Cloning Protocols; Humana Press, Totowa, N.J., 1997, or Ausubel, supra, both of which are incorporated herein by reference.

RT-PCR

For reverse transcription polymerase chain reaction (RT-PCR), two partially degenerate primer sets used for RT-PCR amplification of a cDNA fragment encoding this peptide. Primer set 1 consisted of DNA's #3427-3434, the sequences of which are shown in Table 8, below. Matrix RT-PCR using combinations of primers from this set with cDNA reverse transcribed from primary human neuronal cultures as template yielded the predicted 54 bp cDNA product with primers #3428+3433. All RT-PCR reactions employed 10-50 ng input poly-A+ RNA equivalents per reaction, and were carried out for 35 cycles employing step cycle conditions with a 95° C. denaturation for 1 minute, 50° C. annealing for 30 sec, and a 72° C. extension for 30 sec.

The degeneracy of primers #3428+3433 was further broken down, resulting in primer set 2, comprising DNAs #3448-3455 (Table 3). Matrix RT-PCR was repeated using primer set 2, and cDNA reverse transcribed from poly-A+ RNA from IMR-32 human neuroblastoma cells (American Type Culture Collection, Manassas, Va.), as well as primary human neuronal cultures, as template for amplification. Primers #3450 and 3454 from set 2 most efficiently amplified a cDNA fragment of the predicted size (72 bp), although primers 3450+3453, and 3450+3455 also amplified the same product, albeit at lower efficiency. The DNA sequence of the 72 bp PCR product obtained by amplification of cDNA from IMR-32 cells, and primary human neuronal cultures, with primers 3450 and 3454 is shown in the lower portion of FIG. 4

5' and 3' RACE-PCR

Internal primers matching the upper (coding) strand for 3' Rapid Amplification of 5' Ends (RACE) PCR, and lower (non-coding) strand for 5' RACE PCR were designed and made according to methods known in the art (e.g., Frohman, M. A., M. K. Dush and G. R. Martin (1988). "Rapid production of full-length cDNAs from rare transcripts: amplification using a single gene specific oligo-nucleotide primer." *Proc. Natl. Acad. Sci. U.S.A.* 85(23): 8998-9002.) The DNA primers used for this experiment (#3459 & #3460) are illustrated schematically in FIG. 4, and the exact sequence of these primers is presented in Table 3. These primers can be utilized in standard RACE-PCR methodology employing commercially available templates (e.g. Marathon Ready cDNA®, Clontech Labs), or custom tailored cDNA templates prepared from RNAs of interest as described by Frohman et al. (ibid.).

In experiments carried out in support of the present invention, a variation of RACE was employed to exploit an IMR-32 cDNA library cloned in the retrovirus expression vector pLPCXlox, a derivative of pLNCX. As the vector junctions provide unique anchor sequences abutting the cDNA inserts in this library, they serve the purpose of 5' and 3' anchor primers in RACE methodology. The sequences of the specific 5' and 3' anchor primers we employed to amplify β-secretase cDNA clones from the library, primers #3475 and #3476, are derived from the DNA sequence of the vector provided by Clontech Labs, Inc., and are shown in Table 3.

Primers #3459 and #3476 were used for 3' RACE amplification of downstream sequences from our IMR-32 cDNA library in the vector pLPCXlox. The library had previously been sub-divided into 100 pools of 5,000 clones per pool, and plasmid DNA was isolated from each pool. A survey of the 100 pools with the primers identified as diagnostic for presence of the β-secretase clone, according to methods described in Example 1, above, provided individual pools from the library for RACE-PCR. 100 ng template plasmid from pool 23 was used for PCR amplification with primers 3459+3476. Amplification was carried out for 40 cycles using ampli-Taq Gold®, under the following conditions: denaturation at 95° C. for 1 min, annealing at 65° C. for 45 sec., and extension at 72° C. for 2 min. Reaction products were fractionated by agarose gel chromatography, according to methods known in the art (Ausubel; Sambrook).

An approximately 1.8 Kb PCR fragment was revealed by agarose gel fractionation of the reaction products. The PCR product was purified from the gel and subjected to DNA sequence analysis using primer #3459. The resulting sequence, designated 23A, and the predicted amino acid sequence deduced from the DNA sequence are shown in FIG. 5. Six of the first seven deduced amino-acids from one of the reading frames of 23A were an exact match with the last 7 amino-acids of the N-terminal sequence determined from the purified protein, purified and sequenced in further experiments carried out in support of the present invention, from natural sources.

TABLE 8

| SEQ ID NO. | DNA # | NUCLEOTIDE SEQUENCE | COMMENTS |
|---|---|---|---|
| 22 | 3427 | GAY GAR GAG CCN GAG GA | |
| 23 | 3428 | GAY GAR GAG CCN GAa GA | |
| 24 | 3429 | GAY GAR GAa CCN GAg GA | |
| 25 | 3430 | GAY GAR GAa CCN GAa GA | |
| 26 | 3431 | RTT RTC NAC CAT TTC | |
| 27 | 3432 | RTT RTC NAC CAT cTC | |
| 28 | 3433 | TCN ACC ATY TCN ACA AA | |
| 29 | 3434 | TCN ACC ATY TCN ACG AA | |
| 30 | 3448 | ata t<u>tc tag a</u> GAY GAR GAg CCa GAa GA | 5' primer, break down of 3428 w/5' XbaI tail, 1 of 4 |
| 31 | 3449 | ata t<u>tc tag a</u> GAY GAR GAg CCg GAa GA | 5' primer, break down of 3428 w/5' XbaI tail, 2 of 4 |
| 32 | 3450 | ata t<u>tc tag a</u> GAY GAR GAg CCc GAa GA | 5' primer, break down of 3428 w/5' XbaI tail, 3 of 4 |
| 33 | 3451 | ata t<u>tc tag a</u> GAY GAR GAg CCt GAa GA | 5' primer, break down of 3428 w/5' XbaI tail, 4 of 4 |
| 34 | 3452 | aca c<u>ga att c</u> TT RTC NAC CAT YTC aAC AAA | breakdown of 3433, 1 of 4; tm = 50 |
| 35 | 3453 | aca c<u>ga att c</u> TT RTC NAC CAT YTC gAC AAA | breakdown of 3433 w/5' Eco RI tail, 2 of 4; tm = 50 |
| 36 | 3454 | aca c<u>ga att c</u> TT RTC NAC CAT YTC cAC AAA | breakdown of 3433 w/5' Eco RI tail, 3 of 4; tm = 50 |
| 37 | 3455 | aca c<u>ga att c</u> TT RTC NAC CAT YTC tAC AAA | breakdown of 3433 w/5' Eco RI tail, 4 of 4; tm = 50 |
| 38 | 3459 | aa gaG CCC GGC CGG AGG GGC A | 5' upper strand primer for 3' race encodes eEPGRRG |
| 39 | 3460 | aaa GCT GCC CCT CCG GCC GGG | 3' lower strand primer for 5' RACE |
| 40 | 3475 | AGC TCG TTT AGT GAA CCG TCA GAT CG | pLNCX 5' primer |
| 41 | 3476 | ACC TAC AGG TGG GGT CTT TCA TTC CC | pLNCX, 3' primer |

EXAMPLE 4

β-Secretase Inhibitor Assays

Assays for measuring β-secretase activity are well known in the art. Particularly useful assays, summarized below, are detailed in allowed U.S. Pat. No. 5,744,346, incorporated herein by reference.

A. Preparation of MBP-C125sw

1. Preparation of Cells

Two 250 ml cell culture flasks containing 50 ml LBamp100 per flask were seeded with one colony per flask of *E. coli* pMAL-C125SW cl. 2 (*E. coli* expressing MBP-C125sw fusion protein). Cells were allowed to grow overnight at 20 degrees C. 25 ml were seeded in 500 ml per flask of LBamp100 in 2 liter flasks, which were then allowed to grow at 30 degrees. Optical densities were measured at 600 nm ($OD_{600}$) vs LB broth; 1.5 ml 100 mM IPTG was added when the OD was ~0.5. At this point, an aliqout was taken for SDS-PAGE, "–I". 0.5 ml was centrifuged for 1 min in a Beckman microfuge, and the resulting pellet was dissolved in 0.5 ml 1×LSB. The cells were incubated/induced for 5-6 hours at 30 C, after which a "+I" aliquot was taken. Cells were then centrifuged at 9,000 rpm in a KA9.1 rotor for 10 min at 4 C. Pellets were retained and stored at −20 C.

2. Extraction of Bacterial Cell Pellets

Frozen cell pellets were resuspended in 50 ml 0.2 M NaCl, 50 mM Tris, pH 7.5, then sonicated in rosette vessel for 5×20 sec bursts, with 1 min rests between bursts. The extract was centrifuged at 16,500 rpm in a KAI 8.5 rotor 30 min (39,000× g). Using pipette as a pestle, the sonicated pellet was suspended in 50 ml urea extraction buffer (7.6 M urea, 50 mM Tris pH 7.5, 1 mM EDTA, 0.5% TX-100). The total volume was about 25 ml per flask. The suspension was then sonicated 6×20 sec, with 1 min rests between bursts. The suspension was then centrifuged again at 16,500 rpm 30 min in the KA18.5 rotor. The resulting supernatant was added to 1.5 L of 0.2 M NaCl-Tris buffer with 1% Triton X-100, and was stirred gently at 4 degrees C. for 1 hour, followed by centrifugation at 9,000 rpm in KA9.1, 30 min, 4 C. The supernatant was loaded onto a column of washed amylose (100 ml of 50% slurry; New England BioLabs). The column was washed with 0.2 M NaCl-Tris-1% TX to baseline (+10 column volumes), then with 2 column volumes 0.2M NaCl-Tris-1% reduced Triton X-100. The protein was then eluted with 10 mM maltose in the same buffer. An equal volume of 6 M guanidine HCl/0.5% TX-100 was added to each fraction. Peak fractions were pooled and diluted to a final concentration was about 2 mg/ml. The fractions were stored at −40 degrees C., before dilution (20-fold, to 0.1 mg/ml in 0.15% Triton X-100). Diluted aliquots were also stored at −40 C.

B. Antibody-Based Assays

The assays described in this section are based on the ability of certain antibodies, hereinafter "cleavage-site antibodies," to distinguish cleavage of APP by β-secretase, based on the unique cleavage site and consequent exposure of a specific C-terminus formed by the cleavage. The recognized sequence is a sequence of usually about 3-5 residues is immediately amino terminal of the β amyloid peptide (PAP) produced by β-secretase cleavage of β-APP, such as Val-Lys-Met in wild-type or Val-Asn-Leu- in the Swedish double mutation variant form of APP.

MBP-C125 Assay: Two recombinantly-expressed proteins (FIG. 19 and FIG. 20) were used as substrates for β-secretase. The preferred substrate (FIG. 19) was expressed in *E. coli* as a fusion protein of the last 125 amino acids of APP fused to the carboxy-terminal end of maltose-binding protein (MBP), using commercially available vectors from New England Biolabs. The s-cleavage site was thus 26 amino acids downstream of the start of the C-125 region. This latter site is recognized by SW192.

Figure 19A:
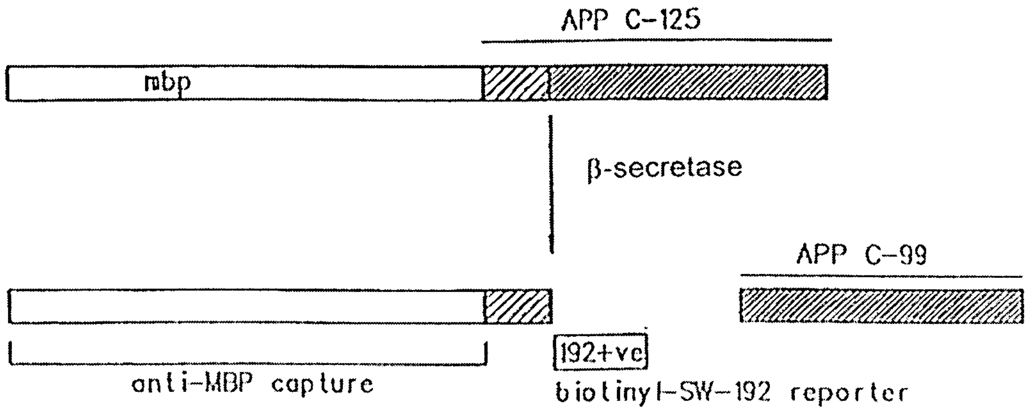
FIGS. 19A and 19 shows a schematic of an APP substrate fragment, and it use in conjunction with antibodies SW192 and 8E-192 in the assay.
Figure 19B:
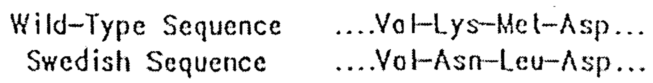
Figure 20:
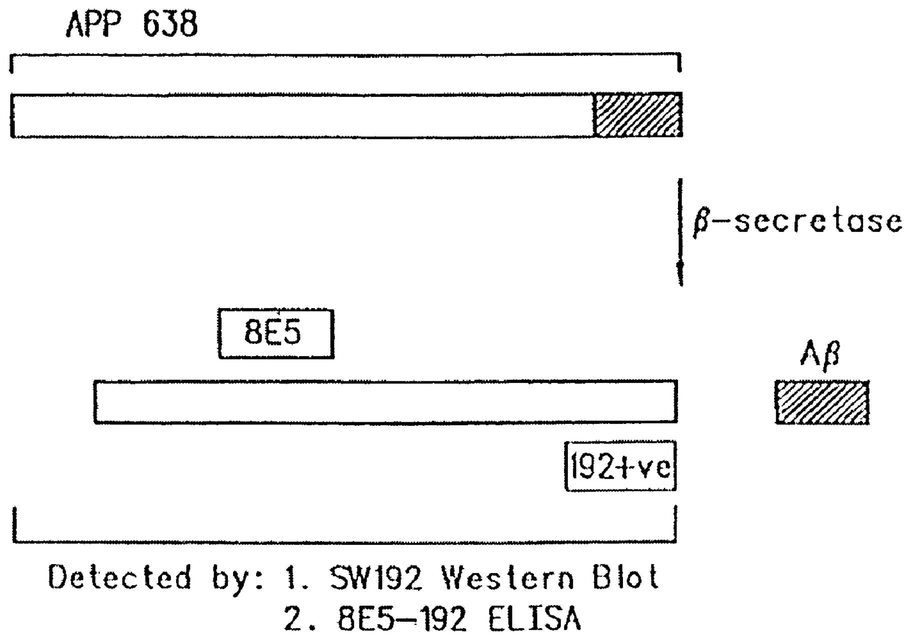
FIG. 20 shows a schematic of schematic of a second APP substrate fragment derived from APP 638, and it use in conjunction with antibodies SW192 and 8E-192 in the assay.

Recombinant proteins were generated with both the wild-type APP sequence (MBP-C125 WT) at the cleavage site ( . . . Val-Lys-Met-Asp-Ala . . . ). (SEQ ID NO:54) or the "Swedish" double mutation (MBP-C125 SW) ( . . . Val-Asn-Leu-Asp-Ala..) (SEQ ID NO:51). As shown in FIG. 19, cleavage of the intact MBP-fusion protein results in the generation of a truncated amino-terminal fragment, with the new SW-192 Ab-positive epitope uncovered at the carboxy terminus. This amino-terminal fragment can be recognized on Western blots with the same Ab, or, quantitatively, using an anti-MBP capture-biotinylated SW-192 reporter sandwich format, as shown in FIG. 19.

Anti-MBP polyclonal antibodies were raised in rabbits (Josman Labs, Berkeley) by immunization with purified recombinantly expressed MBP (New England Biolabs). Antisera were affinity purified on a column of immobilized MBP. MBP-C125 SW and WT substrates were expressed in *E. coli*, then purified as described above.

Microtiter 96-well plates were coated with purified anti-MBP antibody (@ 5-μg/ml), followed by blocking with human serum albumin. Appropriately diluted β-secretase enzyme (5 μl) was mixed with 2.5 μl of 2.2 μM MBP-C125sw substrate stock, in a 50 μl reaction mixture with a final buffer concentration of 20 mM acetate buffer, pH 4.8, 0.06% Triton X-100, in individual wells of a 96-well microtiter plate, and incubated for 1 hour at 37 degrees C. Samples were then diluted 5-fold with Specimen Diluent (0.2 g/l sodium phosphate monobasic, 2.15 g/l sodium phosphate dibasic, 0.5 g/l sodium azide, 8.5 g/l sodium chloride, 0.05% Triton X-405, 6 g/l BSA), further diluted 5-10 fold into Specimen Diluent on anti-MBP coated plates, and incubated for 1 h. Biotinylated SW192 antibodies were used as the reporter. SW192 polyclonal antibodies were biotinylated using NHS-biotin (Pierce), following the manufacturer's instruction. Usually, the biotinylated antibodies were used at about 240 ng/ml, the exact concentration varying with the lot of antibodies used. Following incubation of the plates with the reporter, the ELISA was developed using streptavidin-labeled alkaline phosphatase (Boeringer-Mannheim) and 4-methyl-umbelliferyl phosphate as fluorescent substrate. Plates were read in a Cytofluor 2350 Fluorescent Measurement System. Recombinantly generated MBP-26SW (product analog) was used as a standard to generate a standard curve, which allowed the conversion of fluorescent units into amount of product generated.

This assay protocol was used to screen for inhibitor structures, using "libraries" of compounds assembled onto 96-well microtiter plates. Compounds were added, in a final concentration of 20 μg/ml in 2% DMSO, in the assay format described above, and the extent of product generated compared with control (2% DMSO only) β-secretase incubations, to calculate "% inhibition." "Hits" were defined as compounds which result in >35% inhibition of enzyme activity at test concentration. This assay can also be used to provide $IC_{50}$ values for inhibitors, by varying the concentration of test compound over a range to calculate from a dose-response curve the concentration required to inhibit the activity of the enzyme by 50%.

Generally, inhibition is considered significant as compared to control activity in this assay if it results in activity that is at least 1 standard deviation, and preferably 2 standard deviations lower than a mean activity value determined over a range of samples. In addition, a reduction of activity that is greater than about 25%, and preferably greater than about 35% of control activity may also be considered significant.

Using the foregoing assay system, 24 "hits" were identified (>30% inhibition at 50 μM concentration) from the first 6336 compounds tested (0.4% hit rate). Of these 12 compounds had $IC_{50}$s less than 50 μM, including rescreening in the P26-P4'sw assay, below.

P26-P4'sw assay. The P26-p4'sw substrate is a peptide of the sequence (biotin)CGGADRGLTTRPGSGLTNIK-TEEISEVNLDAEF (SEQ ID NO: 63). The P26-P1 standard has the sequence (biotin)CGGADRGLTTRPGSGLTNIK-TEEISEVNL (SEQ ID NO: 64). Peptides were prepared by Anaspec, Inc. (San Jose, Calif.) using solid phase synthesis with boc-amino acids. Biotin was coupled to the terminal cysteine sulfhydryl by Anaspec, Inc. after synthesis of the peptide, using EZ-liik Iodoacetyl-LC-Biotin (Pierce). Peptides are stored as 0.8-1.0 mM stocks in 5 mM Tris, with the pH adjucted to around neutral (pH 6.5-7.5) with sodium hydroxide.

For the enzyme assay, the substrate concentration can vary from 0-200 μM. Specifically for testing compounds for inhibitory activity, substrate concentration is 1.0 μM. Compounds to be tested were added in DMSO, with a final DMSO concentration of 5%; in such experiments, the controls also receive 5% DMSO. Concentration of enzyme was varied, to give product concentrations within the linear range of the ELISA assay (125-2000 μM, after dilution). These components were incubated in 20 mM sodium acetate, pH 4.5, 0.06% Triton X-100, at 37° C. for 1 to 3 hours. Samples were diluted 5-fold in specimen diluent (145.4 mM sodium chloride, 9.51 mM sodium phosphate, 7.7 mM sodium azide, 0.05% Triton X-405, 6 gm/liter bovine serum albumin, pH 7.4) to quench the reaction, then diluted further for the ELISA as needed. For the ELISA, Costar High Binding 96-well assay plates (Corning, Inc., Corning, N.Y.) were coated with SW 192 monoclonal antibody from clone 16A7, or a clone of similar affinity. P26-P1 standards are diluted in specimen diluent to a final concentration of 0 to 2 nM. Diluted samples and standards (100 μl) are incubated on the SW192 plates at 4° C. for 24 hours. The plates are washed 4 times in TTBS buffer (150 mM sodium chloride, 25 mM Tris, 0.05% Tween 20, pH 7.5), then incubated with 0.1 ml/well of streptavidin—alkaline phosphatase (Roche Molecular Biochemicals, Indianapolis, Ind.) diluted 1:3000 in specimen diluent. After incubating for one hour at room temperature, the plate is washed 4 times in TTBS, and incubated with fluorescent substrate solution A (31.2 gm/liter 2-amino-2-methyl-1-propanol, 30 mg/liter, adjusted to pH 9.5 with HCl). Fluorescent values are read after 30 minutes.

C. Assays Using Synthetic Oligopeptide Substrates

This assay format is particularly useful for measuring activity of partially purified β-secretase preparations. Synthetic oligopeptides are prepared which incorporate the known cleavage site of β-secretase, and optionally detectable tags, such as fluorescent or chromogenic moieties. Examples of such peptides, as well as their production and detection methods are described in allowed U.S. patent application Ser. No. 08/659,984, filed Jun. 7, 1996, herein incorporated by reference. Cleavage products can be detected using high performance liquid chromatography, or fluorescent or chromogenic detection methods appropriate to the peptide to be detected, according to methods well known in the art. By way of example, one such peptide has the sequence SEVNL DAEF (SEQ ID NO: 52), and the cleavage site is between residues 5 and 6. Another preferred substrate has the sequence ADRGLTTRPGSGLTNIKTEEISEVNLDAE F (SEQ ID NO: 53), and the cleavage site is between residues 26 and 27.

D. β-secretase Assays of Crude Cell or Tissue Extracts

Cells or tissues were extracted in extraction buffer (20 mM HEPES, pH 7.5, 2 mM EDTA, 0.2% Triton X-100, 1 mM PMSF, 20 μg/ml pepstatin, 10 μg/ml E-64). The volume of extraction buffer will vary between samples, but should be at least 200 μl per $10^6$ cells. Cells can be suspended by trituration with a micropipette, while tissue may require homogenization. The suspended samples were incubated for 30 minutes on ice. If necessary to allow pipetting, unsolubilized material was removed by centrifugation at 4 degrees C., 16,000×g (14,000 rpm in a Beckman microfuge) for 30 minutes. The supernate was assayed by dilution into the final assay solution. The dilution of extract will vary, but should be sufficient so that the protein concentration in the assay is not greater than 60 μg/ml. The assay reaction also contained 20 mM sodium acetate, pH 4.8, and 0.06% Triton X-100 (including Triton contributed by the extract and substrate), and 220-110 μM MBP-C125 (a 1:10 or 1:20 dilution of the 0.1 mg/ml stock described in the protocol for substrate preparation). Reactions were incubated for 1-3 hours at 37 degrees C. before quenching with at least 5-fold dilution in specimen diluent and assaying using the standard protocol.

EXAMPLE 5

Purification of β-Secretase

A. Purification of Naturally Occurring α-secretase

Frozen tissue (293 cell paste or human brain) was cut into pieces and combined with five volumes of homogenization buffer (20 mM Hepes, pH 7.5, 0.25 M sucrose, 2 mM EDTA). The suspension was homogenized using a blender and centrifuged at 16,000×g for 30 min at 4° C. The supernatants were discarded and the pellets were suspended in extraction buffer (20 mM MES, pH 6.0, 0.5% Triton X-100, 150 mM NaCl, 2 mM EDTA, 5 μg/ml leupeptin, 5 μg/ml E64, 1 μg/ml pepstatin, 0.2 mM PMSF) at the original volume. After vortex-mixing, the extraction was completed by agitating the tubes at 4° C. for a period of one hour. The mixtures were centrifuged as above at 16,000×g, and the supernatants were pooled. The pH of the extract was adjusted to 7.5 by adding ~1% (v/v) of 1 M Tris base (not neutralized).

The neutralized extract was loaded onto a wheat germ agglutinin-agarose (WGA-agarose) column pre-equilibrated with 10 column volumes of 20 mM Tris, pH 7.5, 0.5% Triton X-100, 150 mM NaCl, 2 mM EDTA, at 4° C. One milliliter of the agarose resin was used for every 1 g of original tissue used. The WGA-column was washed with 1 column volume of the equilibration buffer, then 10 volumes of 20 mM Tris, pH 7.5, 100 mM NaCl, 2 mM NaCl, 2 mM EDTA, 0.2% Triton X-100 and then eluted as follows. Three-quarter column volumes of 10% chitin hydrolysate in 20 mM Tris, pH 7.5, 0.5%, 150 mM NaCl, 0.5% Triton X-100, 2 mM EDTA were passed through the column after which the flow was stopped for fifteen minutes. An additional five column volumes of 10% chitin hydrolysate solution were then used to elute the column. All of the above eluates were combined (pooled WGA-eluate).

The pooled WGA-eluate was diluted 1:4 with 20 mM NaOAc, pH 5.0, 0.5% Triton X-100, 2 mM EDTA. The pH of the diluted solution was adjusted to 5.0 by adding a few drops of glacial acetic acid while monitoring the pH. This "SP load" was passed through a 5-ml Pharmacia HiTrap SP-column equilibrated with 20 mM NaOAc, pH 5.0, 0.5% Triton X-100, 2 mM EDTA, at 4 ml/min at 4C. β-Secretase activity was present in the flow-through fraction, which was neutralized by adding enough 1 M Tris (not neutralized) to bring the pH up to 7.5. The enzyme solution was then loaded onto a 1-ml HiTrap Q anion exchange column (Pharmacia Biotech, Piscataway, N.J.) equilibrated with approximately 10 column volumes of 20 mM Tris, pH 7.5, 0.2% hydrogenated Triton X-100, 2 mM EDTA, at 1.5 ml/min at 4° C. The column was washed with 10 column volumes of 20 mM Tris, pH 7.5, 0.2% hydrogenated Triton X-100, 50 mM NaCl, 2 mM EDTA. Protein was eluted using a linear gradient from 50 mM to 350 mM NaCl over 30 minutes at a flow-rate of 1 ml/min at 4° C. The protein concentrations in the HiQ fractions were measured using a BioRad colorimetric protein assay, and the β-secretase activity was measured using the MBP-C125 cleavage assay at pH 4.8. The fractions in the ascending portion of the protein peak have the highest specific activity and were pooled for further purification of the enzyme.

The pooled fractions from the HiTrap Q were then loaded onto a Superdex 200 (26/60) gel exclusion chromatography column, which was eluted with phosphate buffered saline, pH 7.4, 0.2% hydrogenated Triton X-100, 2 mM EDTA, at 1 ml/min, collecting 3 min/fraction. Fractions containing β-secretase activity were identified using the MBP-C125 cleavage assay. The apparent molecular weight of the β-secretase activity eluting from the Superdex column was estimated from the peak elution volume (relative to that of standard proteins) to be 280,000±9800 (average of two runs for 293 cells, and two runs for human brain).

The foregoing methods provided peak activity having a specific activity of greater than 253 nM product/ml/h/1 g protein in the MBP-C125-SW assay, where specific activity is determined as described below, with about 1500-fold purification of the protein. Specific activity of the purified β-secretase was measured as follows. MBP C125-SW substrate was combined at approximately 220 nM in 20 mM sodium acetate, pH 4.8, with 0.06% Triton X-100. The amount of product generated was measured by the β-secretase assay, also described below. Specific activity was then calculated as:

$$Sp.\ Act. = \frac{\text{(Product conc. nM/ml)(Dilution factor)(Incubation vol. µl)}}{\text{(Enzyme sol. vol. µl)(Incubation time h.)}}$$

$$\text{(Enzyme conc. µg/ml)}$$

The Specific Activity is thus expressed as pmoles of product produced per µg of β-secretase per hour. Further purification of human brain enzyme was achieved by loading the SP flow through fraction on to the P10-P4'sta D→V affinity column, according to the general methods described below. Results of this purification step are summarized in Table 1, above.

B. Purification of β-Secretase from Recombinant Cells

Recombinant cells produced by the methods described herein generally were made to over-express the enzyme; that is, they produced dramatically more enzyme per cell than is found to be endogenously produced by most tissues. It was found that some of the steps described above could be omitted from the preparation of purified enzyme under these circumstances, with the result that even higher levels of purification were achieved.

CosA2 or 293 T cells transfected with β-secretase gene construct (see Example 6) were pelleted, frozen and stored at −80 degrees until use. The cell pellet was resuspended by homogenizing for 30 seconds using a handheld homogenizer (0.5 ml/pellet of approximately $10^6$ cells in extraction buffer consisting of 20 mM TRIS buffer, pH 7.5, 2 mM EDTA, 0.2% Triton X-100, plus protease inhibitors: 5 µg/ml E-64, 10 µg/ml pepstatin, 1 mM PMSF), centrifuged as maximum speed in a microfuge (40 minutes at 4 degrees C.). Pellets were suspended in original volume of extraction buffer, then stirred at 1 hour at 4 degrees C. with rotation, and centrifuted again in a microfuge at maximum speed for 40 minutes. The resulting supernatant was saved as the "extract." The extract was then diluted with 20 mM sodium acetate, pH 5.0, 2 mM EDTA and 0.2% Triton X-100 (SP buffer A), and SM NaCl was added to a final concentration of 60 mM NaCl. The pH of the solution was then adjusted to pH 5.0 with glacial acetic acid diluted 1:10 in water. Aliquots were saved ("SP load"). The SP load was passed through a 1 ml SP HiTrap column which was pre-washed with 5 ml SP buffer A, 5 ml SP buffer B (SP buffer A with 1 M NaCl) and 10 ml SP buffer A. An additional 2 ml of 5% SP buffer B was passed through the column to displace any remaining sample from the column. The pH of the SP flo-thru was adjusted to pH 4.5 with 10× diluted acetic acid. This flow-through was then applied to a P10-P4'staD→V-Sepharose Affinity column, as described below. The column (250 µl bed size) was pre-equilibrated with at least 20 column volumes of equilibration buffer (25 mM NaCl, 0.2% Triton X-100, 0.1 mM EDTA, 25 mM sodium acetate, pH 4.5), then loaded with the diluted supernatant. After loading, subsequent steps were carried out at room temperature. The column was washed with washing buffer (125 mM NaCl, 0.2% Triton X-100, 25 mM sodium acetate, pH 4.5) before addition of 0.6 column bed volumes of borate elution buffer (200 mM NaCl, 0.2% reduced Triton X-100, 40 mM sodium borate, pH 9.5). The column was then capped, and an additional 0.2 ml elution buffer was added. The column was allowed to stand for 30 minutes. Two bed volumes elution buffer were added, and column fractions (250 µl) were collected. The protein peak eluted in two fractions. 0.5 ml of 10 mg/ml pepstatin was added per milliliter of collected fractions.

Cell extracts made from cells transfected with full length clone 27 (SEQ ID NO: 2; 1-501), 419stop (SEQ ID NO:57) and 452stop (SEQ ID NO: 59) were detected by Western blot analysis using antibody 264A (polyclonal antibody directed to amino acids 46-67 of β-secretase with reference to SEQ ID NO: 2).

EXAMPLE 6

Preparation of Heterologous Cells Expressing Recombinant β-Secretase

Two separate clones (pCEKclone27 and pCEKclone53) were transfected into 293T or COS(A2) cells using Fugene and Effectene methods known in the art. 293T cells were obtained from Edge Biosystems (Gaithersburg, Md.). They are KEK293 cells transfected with SV40 large antigen. COSA2 are a subclone of COS 1 cells; subcloned in soft agar.

Fugene Method: 293T cells were seeded at $2\times10^5$ cells per well of a 6 well culture plate. Following overnight growth, cells were at approximately 40-50% confluency. Media was changed a few hours before transfection (2 ml/well). For each sample, 3 µl of FuGENE 6 Transfection Reagent (Roche Molecular Biochemicals, Indianapolis, Ind.) was diluted into 0.1 ml of serum-free culture medium (DME with 10 mM Hepes) and incubated at room temperature for 5 min. One microgram of DNA for each sample (0.5-2 mg/ml) was added to a separate tube. The diluted FuGENE reagent was added drop-wise to the concentrated DNA. After gentle tapping to mix, this mixture was incubated at room temperature for 15 minutes. The mixture was added dropwise onto the cells and swirled gently to mix. The cells were then incubated at 37 degrees C., in an atmosphere of 7.5% $CO_2$. The conditioned media and cells were harvested after 48 hours. Conditioned media was collected, centrifuged and isolated from the pellet. Protease inhibitors (5 µg/ml E64, 2 µg/ml peptstatin, 0.2 mM PMSF) were added prior to freezing. The cell monolayer was rinsed once with PBS, tehn 0.5 ml of lysis buffer (1 mM HIPIS, pH 7.5, 1 mM EDTA, 0.5% Triton X-100, 1 mM PMSF, 10 µg/ml E64) was added. The lysate was frozen and thawed, vortex mixed, then centrifuged, and the supernatant was frozen until assayed.

Effectene Method. DNA (0.6 µg) was added with "EFFECTENE" reagent (Qiagen, Valencia, Calif.) into a 6-well culture plate using a standard transfection protocol according to manufacturer's instructions. Cells were harvested 3 days after transfection and the cell pellets were snap frozen. Whole cell lysates were prepared and various amounts of lysate were tested for β-secretase activity using the MBP-C125SW substrate.

FIG. 13 shows the results of these experiments, in which picomoles of product formed is plotted against micrograms of COS cell lysate added to the reaction. The legend to the figure describes the enzyme source, where activity from cells transfected with DNA from pCEKclone27 and PCEKclone53 (clones 27 and 53) using Effectene are shown as closed diamonds and solid squares, respectively, activity from cells transfected with DNA from clone 27 prepared with Fugene are shown as open triangles, and mock transfected and control plots show no activity (closed triangles and "X" markers). Values greater than 700 μM product are out of the linear range of the assay.

EXAMPLE 7

Preparation of P10-P4'sta(D→V) Sepharose Affinity Matrix

A. Preparation of inhibitor peptides, including P10-P4'sta (D→V).

The synthetic peptide inhibitor peptides of the invention were synthesized in a peptide synthesizer using boc-protected amino acids for chain assembly. All chemicals, reagents, and boc amino acids were purchased from Applied Biosystems (ABI; Foster City, Calif.) with the exception of dichloromethane and N,N-dimethylform amide which were from Burdick and Jackson. The starting resin, boc-Phe-OCH2-Pam resin was also purchased from ABI. All amino acids were coupled following preactivation to the corresponding HOBT ester using 1.0 equivalent of 1-hydroxybenzotriazole (HOBT), and 1.0 equivalent of N,N-dicyclohexylcarbodiimide (DCC) in dimethylformamide. The boc protecting group on the amino acid α-amine was removed with 50% trifluoroacetic acid in dichloromethane after each coupling step and prior to Hydrogen Fluoride cleavage.

Amino acid side chain protection was as follows: Glu(Bzl), Lys(Cl-CBZ), Ser(OBzl), Thr(OBzl). All other amino acids were used with no further side chain protection including boc-Statine. [(Bzl) benzyl, (CBZ) carbobenzoxy, (Cl-CBZ) chlorocarbobenzoxy, (OBzl) O-benzyl]

After the sequential addition of all fourteen residues the P10-P4'sta(D→V) peptide has the sequence $NH_2$-KTEEISEVNVAEF-COOH (SEQ ID NO:72), where "sta" represents a statine moiety. The side chain protected peptide resin was deprotected and cleaved from the resin by reacting with anhydrous hydrogen fluoride (HF) at 0° C. for one hour. This generated the fully deprotected crude peptide as a C-terminal carboxylic acid.

Following HF treatment, the peptide was extracted from the resin in acetic acid and lyophilized. The crude peptide was then purified using preparative reverse phase HPLC on a Vydac C4, 330Å, 10 μm column 2.2 cm I.D.×25 cm in length. The solvent system used with this column was 0.1% TFA/H2O ([A] buffer) and 0.1% TFA/CH3CN ([B] buffer) as the mobile phase. Typically the peptide was loaded onto the column in 2% [B] at 8-10 mL/min. and eluted using a linear gradient of 2% [B] to 60% [B] in 174 minutes.

The purified peptide was subjected to mass spectrometry, and analytical reverse phase HPLC to confirm its composition and purity.

B. Incorporation of P10-P4'sta(D→V) into Affinity Matrix

All manipulations were carried out at room temperature. 12.5 ml of 80% slurry of NHS-Sepharose (i.e. 10 ml packed volume; Pharmacia, Piscataway, N.J.) was poured into a Bio-Rad EconoColumn (BioRad, Richmond, Calif.) and washed with 165 ml of ice-cold 1.0 mM HCl. When the bed was fully drained, the bottom of the column was closed off, and 5.0 ml of 7.0 mg/ml P10-P4'sta(D→V) peptide (dissolved in 0.1 M HEPES, pH 8.0) was added. The column was capped and incubated with rotation for 24 hours. After incubation, the column was allowed to drain, then washed with 8 ml of 1.0 M ethanolamine, pH 8.2. An additional 10 ml of the ethanolamine solution was added, and the column was again capped and incubated overnight with rotation. The column bed was washed with 20 ml of 1.5 M sodium chloride, 0.5 M Tris, pH 7.5, followed by a series of buffers containing 0.1 mM EDTA, 0.2% Triton X-100, and the following components; 20 mM sodium acetate, pH 4.5 (100 ml); 20 mM sodium acetate, pH 4.5, 1.0 M sodium chloride (100 ml); 20 mM sodium borate, pH 9.5, 1.0 M sodium chloride (200 ml); 20 mM sodium borate, pH 9.5 (100 ml). Finally, the column bed was washed with 15 ml of 2 mM Tris, 0.01% sodium azide (no Triton or EDTA), and stored in that buffer, at 4° C.

C. Sequences and inhibition data for heptamer peptides (Table 9) with reference to the 10 peptide sequence around the β-secretase cleavage site of the Swedish mutation of APP(P5 to P5').

TABLE 9

<table>
<tr><td>(Swedish)</td><td colspan="11">Example</td></tr>
<tr><td>SEQ ID NO:92</td><td>P5 S</td><td>E</td><td>P3 V</td><td>N</td><td>P1 L</td><td>P1 D</td><td>A</td><td>E</td><td>P4 F</td><td>P5 R</td><td>$IC_{50}$ Group*</td></tr>
<tr><td>7B</td><td></td><td></td><td>|AcV-</td><td>--M--</td><td>-Sta--</td><td>--V---</td><td>------</td><td>------</td><td>------|</td><td></td><td>I</td></tr>
<tr><td>7C</td><td></td><td></td><td>|-----</td><td>------</td><td>------</td><td>-Abu-</td><td>------</td><td>------</td><td>------|</td><td></td><td>II</td></tr>
<tr><td>7D</td><td></td><td></td><td>|-----</td><td>------</td><td>------</td><td>-Phg-</td><td>------</td><td>------</td><td>------|</td><td></td><td>II</td></tr>
<tr><td>7E</td><td></td><td></td><td>|-----</td><td>------</td><td>------</td><td>--A---</td><td>------</td><td>------</td><td>------|</td><td></td><td>II</td></tr>
<tr><td>7F</td><td></td><td></td><td>|-----</td><td>------</td><td>------</td><td>t-Leu</td><td>------</td><td>------</td><td>------|</td><td></td><td>IV</td></tr>
<tr><td>7G</td><td></td><td></td><td>|-----</td><td>-Phg-</td><td>------</td><td>--V---</td><td>------</td><td>------</td><td>------|</td><td></td><td>I</td></tr>
<tr><td>7H</td><td></td><td></td><td>|-----</td><td>n-Leu</td><td>------</td><td>------</td><td>------</td><td>------</td><td>------|</td><td></td><td>I</td></tr>
<tr><td>7I</td><td></td><td></td><td>|-----</td><td>--N--</td><td>------</td><td>------</td><td>------</td><td>------</td><td>------|</td><td></td><td>II</td></tr>
<tr><td>7J</td><td></td><td></td><td>|-----</td><td>--F--</td><td>------</td><td>------</td><td>------</td><td>------</td><td>------|</td><td></td><td>II</td></tr>
<tr><td>7K</td><td></td><td></td><td>|-----</td><td>--E--</td><td>------</td><td>------</td><td>------</td><td>------</td><td>------|</td><td></td><td>II</td></tr>
<tr><td>7L</td><td></td><td></td><td>|-----</td><td>--V--</td><td>------</td><td>------</td><td>------</td><td>------</td><td>------|</td><td></td><td>IV</td></tr>
<tr><td>7M</td><td></td><td></td><td>|-----</td><td>--G--</td><td>------</td><td>------</td><td>------</td><td>------</td><td>------|</td><td></td><td>II</td></tr>
<tr><td>7N</td><td></td><td></td><td>|-----</td><td>--M--</td><td>------</td><td>xxxx†</td><td>-------</td><td>------</td><td>------|</td><td></td><td>II</td></tr>
<tr><td>7O</td><td></td><td></td><td>|-----</td><td>------</td><td>phe-Sta</td><td>--V---</td><td>-------</td><td>------</td><td>------|</td><td></td><td>I</td></tr>
<tr><td>7P</td><td></td><td></td><td>|-----</td><td>------</td><td>nor-Sta</td><td>-------</td><td>-------</td><td>------</td><td>------|</td><td></td><td>II</td></tr>
<tr><td>7Q</td><td></td><td></td><td>|($NH_2$)</td><td>------</td><td>acha</td><td>-------</td><td>-------</td><td>------</td><td>------|</td><td></td><td>II</td></tr>
<tr><td>7R</td><td></td><td></td><td>|-----</td><td>------</td><td>-Sta--</td><td>-------</td><td>xxxx</td><td>------</td><td>------|</td><td></td><td>II</td></tr>
</table>

Heptamers are mapped as P3 to P4'. A dashed line indicates the amino acid at that position is the same as the one immediately above it. A vertical line in a box indicates that that amino acid is the N- or C-terminus.

* Group I has $IC_{50}$ of <μm; Group II of =1<10 μm; Group III =10<20 μm; Group IV =20<50 μm.

† indicates that the amino acid was deleted from the sequence making it a hexameric peptide Abu=α-aminobutyric acid; Phg=phenylglycine; t-Leu tertiary leucine; n-Leu is normal leucine; Statine is a known γ-amino acid Merck Index 11$^{th}$ Ed. # 8759 having the formula $(CH_3)_2CHCH(NH_2)CH(OH)CH_2CO_2H$, phe-Sta=phenylstatine (i.e. Sta having a benzyl side chain); acha is cyclohexylstatine (i.e. Sta having a cyclohexylmethyl side chain); nor-Sta is the statine residue without the methylene group intervening between the carbonyl and hydroxymethylene groups, effectively it is Sta with the "backbone" shortened by one methylene group.

The substrates for these studies were synthesized using solid support sequential synthesis as described above in 7A. Assays of the inhibitory activity were performed in the MBP C125 assays described in Example 4 and $IC_{50}$ values were generated.

Parent ions from mass spectrum analysis of Examples 7B-7R (see Table 7) where available:

| | |
|---|---|
| 7B | MH+ = 895 |
| 7C | MH+ = 881 |
| 7D | MH+ = 929 |
| 7E | MH+ = 867 |
| 7F | MH+ = 909 |
| 7G | MH+ = 897 |
| 7H | MH+ = 877 |
| 7I | MH+ = 878 |
| 7J | MH+ = 911 |
| 7K | MH+ = 893 |
| 7L | MH+ = 863 |
| 7M | MH+ = 821 |

-continued

| | |
|---|---|
| 7N | |
| 7O | |
| 7P | MH+ = 881 |
| 7Q | MH+ = 851 |
| 7R | MH+ = 782 |

EXAMPLE 8

Co-Transfection of Cells with β-Secretase and APP 293T cells were co-transfected with equivalent amounts plasmids encoding APPsw or wt and β-secretase or control β-galalactoside (β-gal) cDNA using FuGene 6 Reagent, as described in Example 4, above. Either pCEKclone27 or pohCJ containing full length β-secretase were used for expression of β-secretase. The plasmid construct pohCK751 used for the expression of APP in these transfections was derived as described in Dugan et al., JBC, 270(18) 10982-10989 (1995) and shown in FIG. 21. A β-gal control plasmid was added so that the total amount of plasmid transfected was the same for each condition. β-gal expressing pCEK and pohCK vectors do not replicate in 293T or COS cells. Triplicate wells of cells were transfected with the plasmid, according to standard methods described above, then incuabated for 48 hours, before collection of conditioned media and cells. Whole cell lysates were prepared and tested for the β-secretase enzymatic activity. The amount of β-secretase activity expressed by transfected 293T cells was comparable to or higher than that expressed by CosA2 cells used in the single transfection studies. Western blot assays were done on conditioned media and cell lysates, using the antibody 13G8, as described below, and Aβ ELISAs carried out on the conditioned media to analyze the various APP cleavage products.

While the invention has been described with reference to specific methods and embodiments, it will be appreciated that various modifications and changes may be made without departing from the invention. All patent and literature references referred to herein are herein incorporated by reference.

The invention claimed is:

1. A compound capable of inhibiting β-secretase wherein the compound is of formula I:

R'-V-X-Y-Z-A-E-F (SEQ ID NO:93) (I)

or a variant thereof in which any of V, A, E and F is/are replaced by a conservative substitution, wherein V, A, E and F are valine, alanine, glutamic acid and phenylalanine, respectively;

$R^1$ is chosen from hydrogen, acetyl, t-butoxycarbonyl and carbobenzoyl;

X is chosen from methionine, phenylglycine, n-leucine (n-Leu), asparagine, phenylalanine, glycine and valine;

Z is chosen from valine, α-aminobutyric acid (Abu), phenylglycine (Phg) and alanine; and Y is statine, acha (cyclohexylmethylstatine) or phenylstatine (Phe-sta) wherein the phenyl group of phenylstatine optionally has mono or di-substitution chosen from the group consisting of Cl, F, Br, methyl and methoxy.

2. The compound of claim 1, wherein said β-secretase inhibitor is chosen from the group consisting of $R^1$-Val-Met-Sta-Val-Ala-Glu-Phe (SEQ ID NO:94); Ac-Val-Phg-Sta-Val-Ala-Glu-Phe (SEQ ID NO:95); $R^1$-Val-Leu-Sta-Val-Ala-Glu-Phe (SEQ ID NO:96); $R^1$-Val-Asn-Sta-Val-Ala-Glu-Phe (SEQ ID NO:97); $R^1$-Val-Phe-Sta-Val-Ala-Glu-Phe (SEQ ID NO:98); and $R^1$-Val-Met-phenyl-Sta-Val-Ala-Glu-Phe (SEQ ID NO:99).

3. The compound of claim 2, wherein in said β-secretase inhibitor $R^1$ is H or acetyl.

4. The compound of claim 3, wherein in said β-secretase inhibitor $R^1$ is acetyl.

5. The compound of claim 4, wherein said β-secretase inhibitor is Ac-Val-Met-Sta-Val-Ala-Glu-Phe (SEQ ID NO: 100).

6. The compound of claim 1, wherein the phenyl group of phenylstatine has mono or di-substitution chosen from the group consisting of Cl, F, Br, methyl and methoxy.

* * * * *

SEQUENCE LISTING

```
<160> NUMBER OF SEQ ID NOS: 101

<210> SEQ ID NO 1
<211> LENGTH: 1503
<212> TYPE: DNA
<213> ORGANISM: Homo sapiens

<400> SEQUENCE: 1

atggcccaag ccctgccctg gctcctgctg tggatgggcg cgggagtgct gcctgcccac      60

ggcacccagc acggcatccg gctgcccctg cgcagcggcc tgggggggcgc ccccctgggg    120

ctgcggctgc cccgggagac cgacgaagag cccgaggagc ccggccggag gggcagcttt    180

gtggagatgg tggacaacct gaggggcaag tcggggcagg gctactacgt ggagatgacc    240

gtgggcagcc ccccgcagac gctcaacatc ctggtggata caggcagcag taactttgca    300

gtgggtgctg ccccccaccc cttcctgcat cgctactacc agaggcagct gtccagcaca    360

taccgggacc tccggaaggg tgtgtatgtg ccctacaccc agggcaagtg ggaaggggag    420

ctgggcaccg acctggtaag catcccccat ggccccaacg tcactgtgcg tgccaacatt    480
```

-continued

```
gctgccatca ctgaatcaga caagttcttc atcaacggct ccaactggga aggcatcctg    540

gggctggcct atgctgagat tgccaggcct gacgactccc tggagccttt ctttgactct    600

ctggtaaagc agacccacgt tcccaacctc ttctccctgc agctttgtgg tgctggcttc    660

cccctcaacc agtctgaagt gctggcctct gtcggaggga gcatgatcat tggaggtatc    720

gaccactcgc tgtacacagg cagtctctgg tatacaccca tccggcggga gtggtattat    780

gaggtgatca ttgtgcgggt ggagatcaat ggacaggatc tgaaaatgga ctgcaaggag    840

tacaactatg acaagagcat tgtggacagt ggcaccacca accttcgttt gcccaagaaa    900

gtgtttgaag ctgcagtcaa atccatcaag gcagcctcct ccacggagaa gttccctgat    960

ggtttctggc taggagagca gctggtgtgc tggcaagcag gcaccacccc ttggaacatt   1020

ttcccagtca tctcactcta cctaatgggt gaggttacca accagtcctt ccgcatcacc   1080

atccttccgc agcaatacct gcggccagtg gaagatgtgg ccacgtccca agacgactgt   1140

tacaagtttg ccatctcaca gtcatccacg ggcactgtta tgggagctgt tatcatggag   1200

ggcttctacg ttgtctttga tcgggcccga aaacgaattg gctttgctgt cagcgcttgc   1260

catgtgcacg atgagttcag gacggcagcg gtggaaggcc cttttgtcac cttggacatg   1320

gaagactgtg gctacaacat tccacagaca gatgagtcaa ccctcatgac catagcctat   1380

gtcatggctg ccatctgcgc cctcttcatg ctgccactct gcctcatggt gtgtcagtgg   1440

cgctgcctcc gctgcctgcg ccagcagcat gatgactttg ctgatgacat ctccctgctg   1500

aag                                                                 1503

<210> SEQ ID NO 2
<211> LENGTH: 501
<212> TYPE: PRT
<213> ORGANISM: Homo sapiens

<400> SEQUENCE: 2

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
```

-continued

```
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500


<210> SEQ ID NO 3
<211> LENGTH: 24
<212> TYPE: DNA
<213> ORGANISM: Homo sapiens

<400> SEQUENCE: 3

gagagacgar garccwgagg agcc                                              24


<210> SEQ ID NO 4
<211> LENGTH: 24
<212> TYPE: DNA
<213> ORGANISM: Artificial
<220> FEATURE:
<223> OTHER INFORMATION: Synthetic degenerate oligonucleotide primer
```

<400> SEQUENCE: 4
gagagacgar garccwgaag agcc 24

<210> SEQ ID NO 5
<211> LENGTH: 24
<212> TYPE: DNA
<213> ORGANISM: Artificial
<220> FEATURE:
<223> OTHER INFORMATION: Synthetic degenerate oligonucleotide primer

<400> SEQUENCE: 5
gagagacgar garccwgaag aacc 24

<210> SEQ ID NO 6
<211> LENGTH: 24
<212> TYPE: DNA
<213> ORGANISM: Artificial
<220> FEATURE:
<223> OTHER INFORMATION: Synthetic degenerate oligonucleotide primer

<400> SEQUENCE: 6
gagagacgar garccwgagg aacc 24

<210> SEQ ID NO 7
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 7
agagacgarg arccsgagga gcc 23

<210> SEQ ID NO 8
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 8
agagacgarg arccsgaaga gcc 23

<210> SEQ ID NO 9
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 9
agagacgarg arccsgaaga acc 23

<210> SEQ ID NO 10
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 10
agagacgarg arccsgagga acc 23

<210> SEQ ID NO 11

-continued

```
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 11

cgtcacagrt trtcaaccat ctc                                              23


<210> SEQ ID NO 12
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 12

cgtcacagrt trtctaccat ctc                                              23


<210> SEQ ID NO 13
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 13

cgtcacagrt trtccaccat ctc                                              23


<210> SEQ ID NO 14
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 14

cgtcacagrt trtcgaccat ctc                                              23


<210> SEQ ID NO 15
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 15

cgtcacagrt trtcaaccat ttc                                              23


<210> SEQ ID NO 16
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 16

cgtcacagrt trtctaccat ttc                                              23


<210> SEQ ID NO 17
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 17
```

-continued cgtcacagrt trtccaccat ttc 23

<210> SEQ ID NO 18
<211> LENGTH: 23
<212> TYPE: DNA
<213> ORGANISM: Artificial
<220> FEATURE:
<223> OTHER INFORMATION: Synthetic degenerate oligonucleotide primer

<400> SEQUENCE: 18
cgtcacagrt trtcgaccat ttc 23

<210> SEQ ID NO 19
<211> LENGTH: 20
<212> TYPE: DNA
<213> ORGANISM: Artificial
<220> FEATURE:
<223> OTHER INFORMATION: Synthetic degenerate oligonucleotide primer

<400> SEQUENCE: 19
gaggggcagc tttgtggaga 20

<210> SEQ ID NO 20
<211> LENGTH: 26
<212> TYPE: DNA
<213> ORGANISM: Artificial
<220> FEATURE:
<223> OTHER INFORMATION: Synthetic degenerate oligonucleotide primer

<400> SEQUENCE: 20
cagcataggc cagccccagg atgcct 26

<210> SEQ ID NO 21
<211> LENGTH: 24
<212> TYPE: DNA
<213> ORGANISM: Artificial
<220> FEATURE:
<223> OTHER INFORMATION: Synthetic degenerate oligonucleotide primer

<400> SEQUENCE: 21
gtgatggcag caatgttggc acgc 24

<210> SEQ ID NO 22
<211> LENGTH: 17
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (12)..(12)
<223> OTHER INFORMATION: n is a, c, g, or t

<400> SEQUENCE: 22
gaygargagc cngagga 17

<210> SEQ ID NO 23
<211> LENGTH: 17
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (12)..(12)
<223> OTHER INFORMATION: n is a, c, g, or t -continued

<400> SEQUENCE: 23
gaygargagc cngaaga 17

<210> SEQ ID NO 24
<211> LENGTH: 17
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (12)..(12)
<223> OTHER INFORMATION: n is a, c, g, or t

<400> SEQUENCE: 24
gaygargaac cngagga 17

<210> SEQ ID NO 25
<211> LENGTH: 17
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(17)
<223> OTHER INFORMATION: N = A, C, G, or T

<400> SEQUENCE: 25
gaygargaac cngaaga 17

<210> SEQ ID NO 26
<211> LENGTH: 15
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(15)
<223> OTHER INFORMATION: N = A, C, G, or T

<400> SEQUENCE: 26
rttrtcnacc atttc 15

<210> SEQ ID NO 27
<211> LENGTH: 15
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(15)
<223> OTHER INFORMATION: N = A, C, G, or T

<400> SEQUENCE: 27
rttrtcnacc atctc 15

<210> SEQ ID NO 28
<211> LENGTH: 17
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(17)
<223> OTHER INFORMATION: N = A, C, G, or T -continued

<400> SEQUENCE: 28
tcnaccatyt cnacaaa 17

<210> SEQ ID NO 29
<211> LENGTH: 17
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(17)
<223> OTHER INFORMATION: N = A, C, G, or T

<400> SEQUENCE: 29
tcnaccatyt cnacgaa 17

<210> SEQ ID NO 30
<211> LENGTH: 27
<212> TYPE: DNA
<213> ORGANISM: Artificial
<220> FEATURE:
<223> OTHER INFORMATION: Synthetic degenerate oligonucleotide primer

<400> SEQUENCE: 30
atattctaga gaygargagc cagaaga 27

<210> SEQ ID NO 31
<211> LENGTH: 27
<212> TYPE: DNA
<213> ORGANISM: Artificial
<220> FEATURE:
<223> OTHER INFORMATION: Synthetic degenerate oligonucleotide primer

<400> SEQUENCE: 31
atattctaga gaygargagc cggaaga 27

<210> SEQ ID NO 32
<211> LENGTH: 27
<212> TYPE: DNA
<213> ORGANISM: Artificial
<220> FEATURE:
<223> OTHER INFORMATION: Synthetic degenerate oligonucleotide primer

<400> SEQUENCE: 32
atattctaga gaygargagc ccgaaga 27

<210> SEQ ID NO 33
<211> LENGTH: 27
<212> TYPE: DNA
<213> ORGANISM: Artificial
<220> FEATURE:
<223> OTHER INFORMATION: Synthetic degenerate oligonucleotide primer

<400> SEQUENCE: 33
atattctaga gaygargagc ctgaaga 27

<210> SEQ ID NO 34
<211> LENGTH: 30
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(30)

-continued

<223> OTHER INFORMATION: N=A, C, G, or T

<400> SEQUENCE: 34
acacgaattc ttrtcnacca tytcaacaaa 30

<210> SEQ ID NO 35
<211> LENGTH: 30
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(30)
<223> OTHER INFORMATION: N = A, C, G, or T

<400> SEQUENCE: 35
acacgaattc ttrtcnacca tytcgacaaa 30

<210> SEQ ID NO 36
<211> LENGTH: 30
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(30)
<223> OTHER INFORMATION: N = A, C, G, or T

<400> SEQUENCE: 36
acacgaattc ttrtcnacca tytccacaaa 30

<210> SEQ ID NO 37
<211> LENGTH: 30
<212> TYPE: DNA
<213> ORGANISM: Artificial
<220> FEATURE:
<223> OTHER INFORMATION: Synthetic degenerate oligonucleotide primer
<220> FEATURE:
<221> NAME/KEY: misc_feature
<222> LOCATION: (1)..(30)
<223> OTHER INFORMATION: N = A, C, G, or T

<400> SEQUENCE: 37
acacgaattc ttrtcnacca tytctacaaa 30

<210> SEQ ID NO 38
<211> LENGTH: 21
<212> TYPE: DNA
<213> ORGANISM: Artificial
<220> FEATURE:
<223> OTHER INFORMATION: Synthetic degenerate oligonucleotide primer

<400> SEQUENCE: 38
aagagcccgg ccggaggggc a 21

<210> SEQ ID NO 39
<211> LENGTH: 21
<212> TYPE: DNA
<213> ORGANISM: Artificial
<220> FEATURE:
<223> OTHER INFORMATION: Synthetic degenerate oligonucleotide primer

<400> SEQUENCE: 39
aaagctgccc ctccggccgg g 21

-continued

<210> SEQ ID NO 40
<211> LENGTH: 26
<212> TYPE: DNA
<213> ORGANISM: Artificial
<220> FEATURE:
<223> OTHER INFORMATION: Synthetic degenerate oligonucleotide primer

<400> SEQUENCE: 40
agctcgttta gtgaaccgtc agatcg 26

<210> SEQ ID NO 41
<211> LENGTH: 26
<212> TYPE: DNA
<213> ORGANISM: Artificial
<220> FEATURE:
<223> OTHER INFORMATION: Synthetic degenerate oligonucleotide primer

<400> SEQUENCE: 41
acctacaggt ggggtctttc attccc 26

<210> SEQ ID NO 42
<211> LENGTH: 2348
<212> TYPE: DNA
<213> ORGANISM: Homo sapiens

<400> SEQUENCE: 42
ccatgccggc ccctcacagc cccgccggga gcccgagccc gctgcccagg ctggccgccg 60
csgtgccgat gtagcgggct ccggatccca gcctctcccc tgctcccgtg ctctgcggat 120
ctcccctgac cgctctccac agcccggacc cgggggctgg cccagggccc tgcaggccct 180
ggcgtcctga tgcccccaag ctccctctcc tgagaagcca ccagcaccac ccagacttgg 240
gggcaggcgc cagggacgga cgtgggccag tgcgagccca gagggcccga aggccggggc 300
ccaccatggc ccaagccctg ccctggctcc tgctgtggat gggcgcggga gtgctgcctg 360
cccacggcac ccagcacggc atccggctgc ccctgcgcag cggcctgggg ggcgcccccc 420
tggggctgcg gctgccccgg gagaccgacg aagagcccga ggagcccggc cggaggggca 480
gctttgtgga gatggtggac aacctgaggg gcaagtcggg gcagggctac tacgtggaga 540
tgaccgtggg cagcccccog cagacgctca acatcctggt ggatacaggc agcagtaact 600
ttgcagtggg tgctgccccc cacccettcc tgcatcgcta ctaccagagg cagctgtcca 660
gcacataccg ggacctccgg aagggtgtgt atgtgcccta cacccagggc aagtgggaag 720
gggagctggg caccgacctg gtaagcatcc cccatggccc caacgtcact gtgcgtgcca 780
acattgctgc catcactgaa tcagacaagt tcttcatcaa cggctccaac tgggaaggca 840
tcctggggct ggcctatgct gagattgcca ggcctgacga ctccctggag cctttctttg 900
actctctggt aaagcagacc cacgttccca acctcttctc cctgcagctt tgtggtgctg 960
gcttccccct caaccagtct gaagtgctgg cctctgtcgg agggagcatg atcattggag 1020
gtatcgacca ctcgctgtac acaggcagtc tctggtatac acccatccgg cgggagtggt 1080
attatgaggt gatcattgtg cgggtggaga tcaatggaca ggatctgaaa atggactgca 1140
aggagtacaa ctatgacaag agcattgtgg acagtggcac caccaacctt cgtttgccca 1200
agaaagtgtt tgaagctgca gtcaaatcca tcaaggcagc ctcctccacg gagaagttcc 1260
ctgatggttt ctggctagga gagcagctgg tgtgctggca agcaggcacc accccttgga 1320
acattttccc agtcatctca ctctacctaa tgggtgaggt taccaaccag tccttccgca 1380
tcaccatcct tccgcagcaa tacctgcggc cagtggaaga tgtggccacg tcccaagacg 1440

-continued

```
actgttacaa gtttgccatc tcacagtcat ccacgggcac tgttatggga gctgttatca   1500

tggagggctt ctacgttgtc tttgatcggg cccgaaaacg aattggcttt gctgtcagcg   1560

cttgccatgt gcacgatgag ttcaggacgg cagcggtgga aggccctttt gtcaccttgg   1620

acatggaaga ctgtggctac aacattccac agacagatga gtcaaccctc atgaccatag   1680

cctatgtcat ggctgccatc tgcgccctct tcatgctgcc actctgcctc atggtgtgtc   1740

agtggcgctg cctccgctgc ctgcgccagc agcatgatga ctttgctgat gacatctccc   1800

tgctgaagtg aggaggccca tgggcagaag atagagattc ccctggacca cacctccgtg   1860

gttcactttg gtcacaagta ggagacacag atggcacctg tggccagagc acctcaggac   1920

cctccccacc caccaaatgc ctctgccttg atggagaagg aaaaggctgg caaggtgggt   1980

tccagggact gtacctgtag gaaacagaaa agagaagaaa gaagcactct gctggcggga   2040

atactcttgg tcacctcaaa tttaagtcgg gaaattctgc tgcttgaaac ttcagccctg   2100

aacctttgtc caccattcct ttaaattctc caacccaaag tattcttctt ttcttagttt   2160

cagaagtact ggcatcacac gcaggttacc ttggcgtgtg tccctgtggt accctggcag   2220

agaagagacc aagcttgttt ccctgctggc caaagtcagt aggagaggat gcacagtttg   2280

ctatttgctt tagagacagg gactgtataa acaagcctaa cattggtgca aagattgcct   2340

cttgaatt                                                            2348


<210> SEQ ID NO 43
<211> LENGTH: 456
<212> TYPE: PRT
<213> ORGANISM: Homo sapiens

<400> SEQUENCE: 43

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30

Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125

Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Asn Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205
```

-continued

```
Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn Ile Phe Pro Val Ile Ser Leu Tyr Leu Met
    290                 295                 300

Gly Glu Val Thr Asn Gln Ser Phe Arg Ile Thr Ile Leu Pro Gln Gln
305                 310                 315                 320

Tyr Leu Arg Pro Val Glu Asp Val Ala Thr Ser Gln Asp Asp Cys Tyr
                325                 330                 335

Lys Phe Ala Ile Ser Gln Ser Ser Thr Gly Thr Val Met Gly Ala Val
            340                 345                 350

Ile Met Glu Gly Phe Tyr Val Val Phe Asp Arg Ala Arg Lys Arg Ile
        355                 360                 365

Gly Phe Ala Val Ser Ala Cys His Val His Asp Glu Phe Arg Thr Ala
    370                 375                 380

Ala Val Glu Gly Pro Phe Val Thr Leu Asp Met Glu Asp Cys Gly Tyr
385                 390                 395                 400

Asn Ile Pro Gln Thr Asp Glu Ser Thr Leu Met Thr Ile Ala Tyr Val
                405                 410                 415

Met Ala Ala Ile Cys Ala Leu Phe Met Leu Pro Leu Cys Leu Met Val
            420                 425                 430

Cys Gln Trp Arg Cys Leu Arg Cys Leu Arg Gln Gln His Asp Asp Phe
        435                 440                 445

Ala Asp Asp Ile Ser Leu Leu Lys
    450                 455
```

<210> SEQ ID NO 44
<211> LENGTH: 2348
<212> TYPE: DNA
<213> ORGANISM: Homo sapiens

<400> SEQUENCE: 44

```
ccatgccggc ccctcacagc cccgccggga gcccgagccc gctgcccagg ctggccgccg     60

csgtgccgat gtagcgggct ccggatccca gcctctcccc tgctcccgtg ctctgcggat    120

ctcccctgac cgctctccac agcccggacc cgggggctgg cccagggccc tgcaggccct    180

ggcgtcctga tgcccccaag ctccctctcc tgagaagcca ccagcaccac ccagacttgg    240

gggcaggcgc cagggacgga cgtgggccag tgcgagccca gagggcccga aggccggggc    300

ccaccatggc ccaagccctg ccctggctcc tgctgtggat gggcgcggga gtgctgcctg    360

cccacggcac ccagcacggc atccggctgc ccctgcgcag cggcctgggg ggcgcccccc    420

tggggctgcg gctgccccgg gagaccgacg aagagcccga ggagcccggc cggaggggca    480

gctttgtgga gatggtggac aacctgaggg gcaagtcggg gcagggctac tacgtggaga    540

tgaccgtggg cagccccccg cagacgctca acatcctggt ggatacaggc agcagtaact    600

ttgcagtggg tgctgccccc cacccccttcc tgcatcgcta ctaccagagg cagctgtcca    660

gcacataccg ggacctccgg aagggtgtgt atgtgcccta cacccagggc aagtgggaag    720
```

-continued

```
gggagctggg caccgacctg gtaagcatcc cccatggccc caacgtcact gtgcgtgcca    780
acattgctgc catcactgaa tcagacaagt tcttcatcaa cggctccaac tgggaaggca    840
tcctggggct ggcctatgct gagattgcca ggcctgacga ctccctggag cctttctttg    900
actctctggt aaagcagacc cacgttccca acctcttctc cctgcagctt tgtggtgctg    960
gcttccccct caaccagtct gaagtgctgg cctctgtcgg agggagcatg atcattggag   1020
gtatcgacca ctcgctgtac acaggcagtc tctggtatac acccatccgg cgggagtggt   1080
attatgaggt gatcattgtg cgggtggaga tcaatggaca ggatctgaaa atggactgca   1140
aggagtacaa ctatgacaag agcattgtgg acagtggcac caccaacctt cgtttgccca   1200
agaaagtgtt tgaagctgca gtcaaatcca tcaaggcagc ctcctccacg gagaagttcc   1260
ctgatggttt ctggctagga gagcagctgg tgtgctggca agcaggcacc accccttgga   1320
acattttccc agtcatctca ctctacctaa tgggtgaggt taccaaccag tccttccgca   1380
tcaccatcct tccgcagcaa tacctgcggc cagtggaaga tgtggccacg tcccaagacg   1440
actgttacaa gtttgccatc tcacagtcat ccacgggcac tgttatggga gctgttatca   1500
tggagggctt ctacgttgtc tttgatcggg cccgaaaacg aattggcttt gctgtcagcg   1560
cttgccatgt gcacgatgag ttcaggacgg cagcggtgga aggccctttt gtcaccttgg   1620
acatggaaga ctgtggctac aacattccac agacagatga gtcaaccctc atgaccatag   1680
cctatgtcat ggctgccatc tgcgccctct tcatgctgcc actctgcctc atggtgtgtc   1740
agtggcgctg cctccgctgc ctgcgccagc agcatgatga ctttgctgat gacatctccc   1800
tgctgaagtg aggaggccca tgggcagaag atagagattc ccctggacca cacctccgtg   1860
gttcactttg gtcacaagta ggagacacag atggcacctg tggccagagc acctcaggac   1920
cctccccacc caccaaatgc ctctgccttg atggagaagg aaaaggctgg caaggtgggt   1980
tccagggact gtacctgtag gaaacagaaa agagaagaaa gaagcactct gctggcggga   2040
atactcttgg tcacctcaaa tttaagtcgg gaaattctgc tgcttgaaac ttcagccctg   2100
aacctttgtc caccattcct ttaaattctc caacccaaag tattcttctt ttcttagttt   2160
cagaagtact ggcatcacac gcaggttacc ttggcgtgtg tccctgtggt accctggcag   2220
agaagagacc aagcttgttt ccctgctggc caaagtcagt aggagaggat gcacagtttg   2280
ctatttgctt tagagacagg gactgtataa acaagcctaa cattggtgca aagattgcct   2340
cttgaatt                                                            2348
```

```
<210> SEQ ID NO 45
<211> LENGTH: 8
<212> TYPE: PRT
<213> ORGANISM: Artificial
<220> FEATURE:
<223> OTHER INFORMATION: Synthetic Flag sequence

<400> SEQUENCE: 45

Asp Tyr Lys Asp Asp Asp Asp Lys
1               5


<210> SEQ ID NO 46
<211> LENGTH: 22
<212> TYPE: PRT
<213> ORGANISM: Homo sapiens

<400> SEQUENCE: 46

Met Ala Gln Ala Leu Pro Trp Leu Leu Leu Trp Met Gly Ala Gly Val
```

-continued

```
1               5                   10                  15

Leu Pro Ala His Gly Thr
            20


<210> SEQ ID NO 47
<211> LENGTH: 23
<212> TYPE: PRT
<213> ORGANISM: Homo sapiens

<400> SEQUENCE: 47

Gln His Gly Ile Arg Leu Pro Leu Arg Ser Gly Leu Gly Gly Ala Pro
1               5                   10                  15

Leu Gly Leu Arg Leu Pro Arg
            20


<210> SEQ ID NO 48
<211> LENGTH: 16080
<212> TYPE: DNA
<213> ORGANISM: Artificial
<220> FEATURE:
<223> OTHER INFORMATION: Synthetic expression vector pCEK
<220> FEATURE:
<221> NAME/KEY: misc_feature
<222> LOCATION: (1)..(16080)
<223> OTHER INFORMATION: N = A, C, G, or T

<400> SEQUENCE: 48

ttctcatgtt tgacagctta tcatcgcaga tccgggcaac gttgttgcat tgctgcaggc     60

gcagaactgg taggtatgga agatccgatg tacgggccag atatacgcgt tgacattgat    120

tattgactag ttattaatag taatcaatta cggggtcatt agttcatagc ccatatatgg    180

agttccgcgt tacataactt acggtaaatg gcccgcctgg ctgaccgccc aacgaccccc    240

gcccattgac gtcaataatg acgtatgttc ccatagtaac gccaataggg actttccatt    300

gacgtcaatg ggtggactat ttacggtaaa ctgcccactt ggcagtacat caagtgtatc    360

atatgccaag tacgccccct attgacgtca atgacggtaa atggcccgcc tggcattatg    420

cccagtacat gaccttatgg gactttccta cttggcagta catctacgta ttagtcatcg    480

ctattaccat ggtgatgcgg ttttggcagt acatcaatgg gcgtggatag cggtttgact    540

cacggggatt tccaagtctc caccccattg acgtcaatgg gagtttgttt tggcaccaaa    600

atcaacggga ctttccaaaa tgtcgtaaca actccgcccc attgacgcaa atgggcggta    660

ggcgtgtacg gtgggaggtc tatataagca gagctctctg gctaactaga gaacccactg    720

cttactggct tatcgaaatt aatacgactc actataggga gacccaagct ctgttgggct    780

cgcggttgag gacaaactct tcgcggtctt tccagtactc ttggatcgga aacccgtcgg    840

cctccgaacg gtactccgcc accgagggac ctgagcgagt ccgcatcgac cggatcggaa    900

aacctctcga ctgttggggt gagtactccc tctcaaaagc gggcatgact tctgcgctaa    960

gattgtcagt ttccaaaaac gaggaggatt tgatattcac ctggcccgcg gtgatgcctt   1020

tgagggtggc cgcgtccatc tggtcagaaa agacaatctt tttgttgtca agcttgaggt   1080

gtggcaggct tgagatctgg ccatacactt gagtgacaat gacatccact ttgcctttct   1140

ctccacaggt gtccactccc aggtccaact gcaggtcgac tctagacccg gggaattctg   1200

cagatatcca tcacactggc cgcactcgtc cccagcccgc ccgggagctg cgagccgcga   1260

gctggattat ggtggcctga gcagccaacg cagccgcagg agcccggagc ccttgcccct   1320

gcccgcgccg ccgcccgccg gggggaccag ggaagccgcc accggcccgc catgcccgcc   1380
```

-continued

```
cctcccagcc ccgccgggag cccgcgcccg ctgcccaggc tggccgccgc cgtgccgatg   1440
tagcgggctc cggatcccag cctctcccct gctcccgtgc tctgcggatc tcccctgacc   1500
gctctccaca gcccggaccc gggggctggc ccagggccct gcaggccctg gcgtcctgat   1560
gcccccaagc tccctctcct gagaagccac cagcaccacc cagacttggg ggcaggcgcc   1620
agggacggac gtgggccagt gcgagcccag agggcccgaa ggccggggcc caccatggcc   1680
caagccctgc cctggctcct gctgtggatg ggcgcgggag tgctgcctgc ccacggcacc   1740
cagcacggca tccggctgcc cctgcgcagc ggcctggggg gcgccccccct ggggctgcgg   1800
ctgccccggg agaccgacga agagcccgag gagcccggcc ggaggggcag ctttgtggag   1860
atggtggaca acctgagggg caagtcgggg cagggctact acgtggagat gaccgtgggc   1920
agccccccgc agacgctcaa catcctggtg gatacaggca gcagtaactt tgcagtgggt   1980
gctgcccccc accccttcct gcatcgctac taccagaggc agctgtccag cacataccgg   2040
gacctccgga agggtgtgta tgtgccctac acccagggca agtgggaagg ggagctgggc   2100
accgacctgg taagcatccc ccatggcccc aacgtcactg tgcgtgccaa cattgctgcc   2160
atcactgaat cagacaagtt cttcatcaac ggctccaact gggaaggcat cctggggctg   2220
gcctatgctg agattgccag gcctgacgac tccctggagc ctttctttga ctctctggta   2280
aagcagaccc acgttcccaa cctcttctcc ctgcagcttt gtggtgctgg cttccccctc   2340
aaccagtctg aagtgctggc ctctgtcgga gggagcatga tcattggagg tatcgaccac   2400
tcgctgtaca caggcagtct ctggtataca cccatccggc gggagtggta ttatgaggtc   2460
atcattgtgc gggtggagat caatggacag gatctgaaaa tggactgcaa ggagtacaac   2520
tatgacaaga gcattgtgga cagtggcacc accaaccttc gtttgcccaa gaaagtgttt   2580
gaagctgcag tcaaatccat caaggcagcc tcctccacgg agaagttccc tgatggtttc   2640
tggctaggag agcagctggt gtgctggcaa gcaggcacca ccccttggaa cattttccca   2700
gtcatctcac tctacctaat gggtgaggtt accaaccagt ccttccgcat caccatcctt   2760
ccgcagcaat acctgcggcc agtggaagat gtggccacgt cccaagacga ctgttacaag   2820
tttgccatct cacagtcatc cacgggcact gttatgggag ctgttatcat ggagggcttc   2880
tacgttgtct ttgatcgggc ccgaaaacga attggctttg ctgtcagcgc ttgccatgtg   2940
cacgatgagt tcaggacggc agcggtggaa ggcccttttg tcaccttgga catggaagac   3000
tgtggctaca acattccaca gacagatgag tcaaccctca tgaccatagc ctatgtcatg   3060
gctgccatct gcgccctctt catgctgcca ctctgcctca tggtgtgtca gtggcgctgc   3120
ctccgctgcc tgcgccagca gcatgatgac tttgctgatg acatctccct gctgaagtga   3180
ggaggcccat gggcagaaga tagagattcc cctggaccac acctccgtgg ttcactttgg   3240
tcacaagtag gagacacaga tggcacctgt ggccagagca cctcaggacc ctccccaccc   3300
accaaatgcc tctgccttga tggagaagga aaaggctggc aaggtgggtt ccagggactg   3360
tacctgtagg aaacagaaaa gagaagaaag aagcactctg ctggcgggaa tactcttggt   3420
cacctcaaat ttaagtcggg aaattctgct gcttgaaact tcagccctga acctttgtcc   3480
accattcctt taaattctcc aacccaaagt attcttcttt tcttagtttc agaagtactg   3540
gcatcacacg caggttacct tggcgtgtgt ccctgtggta ccctggcaga gaagagacca   3600
agcttgtttc cctgctggcc aaagtcagta ggagaggatg cacagtttgc tatttgcttt   3660
agagacaggg actgtataaa caagcctaac attggtgcaa agattgcctc ttgaattaaa   3720
aaaaaaaact agattgacta tttatacaaa tgggggcggc tggaaagagg agaaggagag   3780
```

-continued

```
ggagtacaaa gacagggaat agtgggatca aagctaggaa aggcagaaac acaaccactc   3840
accagtccta gttttagacc tcatctccaa gatagcatcc catctcagaa gatgggtgtt   3900
gttttcaatg ttttcttttc tgtggttgca gcctgaccaa aagtgagatg ggaagggctt   3960
atctagccaa agagctcttt tttagctctc ttaaatgaag tgcccactaa gaagttccac   4020
ttaacacatg aatttctgcc atattaattt cattgtctct atctgaacca ccctttattc   4080
tacatatgat aggcagcact gaaatatcct aaccccctaa gctccaggtg ccctgtggga   4140
gagcaactgg actatagcag ggctgggctc tgtcttcctg gtcataggct cactctttcc   4200
cccaaatctt cctctggagc tttgcagcca aggtgctaaa aggaataggt aggagacctc   4260
ttctatctaa tccttaaaag cataatgttg aacattcatt caacagctga tgccctataa   4320
cccctgcctg gatttcttcc tattaggcta taagaagtag caagatcttt acataattca   4380
gagtggtttc attgccttcc taccctctct aatggcccct ccatttattt gactaaagca   4440
tcacacagtg gcactagcat tataccaaga gtatgagaaa tacagtgctt tatggctcta   4500
acattactgc cttcagtatc aaggctgcct ggagaaagga tggcagcctc agggcttcct   4560
tatgtcctcc accacaagag ctccttgatg aaggtcatct ttttccccta tcctgttctt   4620
cccctccccg ctcctaatgg tacgtgggta cccaggctgg ttcttgggct aggtagtggg   4680
gaccaagttc attacctccc tatcagttct agcatagtaa actacggtac cagtgttagt   4740
gggaagagct gggttttcct agtataccca ctgcatccta ctcctacctg gtcaacccgc   4800
tgcttccagg tatgggacct gctaagtgtg gaattacctg ataagggaga gggaaataca   4860
aggagggcct ctggtgttcc tggcctcagc cagctgccca caagccataa accaataaaa   4920
caagaatact gagtcagttt tttatctggg ttctcttcat tcccactgca cttggtgctg   4980
ctttggctga ctgggaacac cccataacta cagagtctga caggaagact ggagactgtc   5040
cacttctagc tcggaactta ctgtgtaaat aaactttcag aactgctacc atgaagtgaa   5100
aatgccacat tttgctttat aatttctacc catgttggga aaaactggct ttttcccagc   5160
cctttccagg gcataaaact caaccccttc gatagcaagt cccatcagcc tattattttt   5220
ttaaagaaaa cttgcacttg tttttctttt tacagttact tccttcctgc cccaaaatta   5280
taaactctaa gtgtaaaaaa aagtcttaac aacagcttct tgcttgtaaa aatatgtatt   5340
atacatctgt atttttaaat tctgctcctg aaaaatgact gtcccattct ccactcactg   5400
catttggggc ctttcccatt ggtctgcatg tcttttatca ttgcaggcca gtggacagag   5460
ggagaaggga gaacaggggt cgccaacact tgtgttgctt tctgactgat cctgaacaag   5520
aaagagtaac actgaggcgc tcgctcccat gcacaactct ccaaaacact tatcctcctg   5580
caagagtggg ctttccgggt ctttactggg aagcagttaa gccccctcct caccccttcc   5640
ttttttcttt ctttactcct ttggcttcaa aggattttgg aaaagaaaca atatgcttta   5700
cactcatttt caatttctaa atttgcaggg gatactgaaa aatacggcag gtggcctaag   5760
gctgctgtaa agttgagggg agaggaaatc ttaagattac aagataaaaa acgaatcccc   5820
taaacaaaaa gaacaataga actggtcttc cattttgcca cctttcctgt tcatgacagc   5880
tactaacctg gagacagtaa catttcatta accaaagaaa gtgggtcacc tgacctctga   5940
agagctgagt actcaggcca ctccaatcac cctacaagat gccaaggagg tcccaggaag   6000
tccagctcct taaactgacg ctagtcaata aacctgggca agtgaggcaa gagaaatgag   6060
gaagaatcca tctgtgaggt gacaggcacg gatgaaagac aaagacggaa aagagtatca   6120
```

-continued

```
aaggcagaaa ggagatcatt tagttgggtc tgaaaggaaa agtntttgct atccgacatg   6180
tactgctagt wcctgtaagc attttaggtc ccagaatgga aaaaaaaatc aagctatngg   6240
ttatataata atgnnnnnnn nnnnnnnnnn nntcgagcat gcatctagag ggccctattc   6300
tatagtgtca cctaaatgct agagctcgct gatcagcctc gactgtgcct tctagttgcc   6360
agccatctgt tgtttgcccc tcccccgtgc cttccttgac cctggaaggt gccactccca   6420
ctgtcctttc ctaataaaat gaggaaattg catcgcattg tctgagtagg tgtcattcta   6480
ttctgggggg tggggtgggg caggacagca agggggagga ttgggaagac aatagcaggc   6540
atgctgggga tgcggtgggc tctatggctt ctgaggcgga aagaaccagc tggggctcta   6600
gggggtatcc ccacgcgccc tgtagcggcg cattaagcgc ggcgggtgtg gtggttacgc   6660
gcagcgtgac cgctacactt gccagcgccc tagcgcccgc tcctttcgct ttcttccctt   6720
cctttctcgc cacgttcgcc ggctttcccc gtcaagctct aaatcggggc atccctttag   6780
ggttccgatt tagtgcttta cggcacctcg accccaaaaa acttgattag ggtgatggtt   6840
cacgtagtgg gccatcgccc tgatagacgg tttttcgccc tttgacgttg gagtccacgt   6900
tctttaatag tggactcttg ttccaaactg gaacaacact caaccctatc tcggtctatt   6960
cttttgattt ataagggatt ttggggattt cggcctattg gttaaaaaat gagctgattt   7020
aacaaaaatt taacgcgaat tctagagccc cgccgccgga cgaactaaac ctgactacgg   7080
catctctgcc ccttcttcgc ggggcagtgc atgtaatccc ttcagttggt tggtacaact   7140
tgccaactgg gccctgttcc acatgtgaca cggggggggga ccaaacacaa aggggttctc   7200
tgactgtagt tgacatcctt ataaatggat gtgcacattt gccaacactg agtggctttc   7260
atcctggagc agactttgca gtctgtggac tgcaacacaa cattgccttt atgtgtaact   7320
cttggctgaa gctcttacac caatgctggg ggacatgtac ctcccagggg cccaggaaga   7380
ctacgggagg ctacaccaac gtcaatcaga ggggcctgtg tagctaccga taagcggacc   7440
ctcaagaggg cattagcaat agtgtttata aggccccctt gttaacccta aacgggtagc   7500
atatgcttcc cgggtagtag tatatactat ccagactaac cctaattcaa tagcatatgt   7560
tacccaacgg gaagcatatg ctatcgaatt agggttagta aaagggtcct aaggaacagc   7620
gatatctccc accccatgag ctgtcacggt tttatttaca tggggtcagg attccacgag   7680
ggtagtgaac cattttagtc acaagggcag tggctgaaga tcaaggagcg ggcagtgaac   7740
tctcctgaat cttcgcctgc ttcttcattc tccttcgttt agctaataga ataactgctg   7800
agttgtgaac agtaaggtgt atgtgaggtg ctcgaaaaca aggtttcagg tgacgccccc   7860
agaataaaat ttggacgggg ggttcagtgg tggcattgtg ctatgacacc aatataaccc   7920
tcacaaaccc cttgggcaat aaatactagt gtaggaatga aacattctga atatctttaa   7980
caatagaaat ccatggggtg gggacaagcc gtaaagactg gatgtccatc tcacacgaat   8040
ttatggctat gggcaacaca taatcctagt gcaatatgat actggggtta ttaagatgtg   8100
tcccaggcag ggaccaagac aggtgaacca tgttgttaca ctctatttgt aacaagggga   8160
aagagagtgg acgccgacag cagcggactc cactggttgt ctctaacacc cccgaaaatt   8220
aaacggggct ccacgccaat ggggcccata aacaaagaca agtggccact ctttttttg   8280
aaattgtgga gtgggggcac gcgtcagccc ccacacgccg ccctgcggtt ttggactgta   8340
aaataagggt gtaataactt ggctgattgt aaccccgcta accactgcgg tcaaaccact   8400
tgcccacaaa accactaatg gcaccccggg gaatacctgc ataagtaggt gggcgggcca   8460
agataggggc gcgattgctg cgatctggag gacaaattac acacacttgc gcctgagcgc   8520
```

-continued

```
caagcacagg gttgttggtc ctcatattca cgaggtcgct gagagcacgg tgggctaatg   8580
ttgccatggg tagcatatac tacccaaata tctggatagc atatgctatc ctaatctata   8640
tctgggtagc ataggctatc ctaatctata tctgggtagc atatgctatc ctaatctata   8700
tctgggtagt atatgctatc ctaatttata tctgggtagc ataggctatc ctaatctata   8760
tctgggtagc atatgctatc ctaatctata tctgggtagt atatgctatc ctaatctgta   8820
tccgggtagc atatgctatc ctaatagaga ttagggtagt atatgctatc ctaatttata   8880
tctgggtagc atatactacc caaatatctg gatagcatat gctatcctaa tctatatctg   8940
ggtagcatat gctatcctaa tctatatctg ggtagcatag gctatcctaa tctatatctg   9000
ggtagcatat gctatcctaa tctatatctg ggtagtatat gctatcctaa tttatatctg   9060
ggtagcatag gctatcctaa tctatatctg ggtagcatat gctatcctaa tctatatctg   9120
ggtagtatat gctatcctaa tctgtatccg ggtagcatat gctatcctca tgcatataca   9180
gtcagcatat gatacccagt agtagagtgg gagtgctatc ctttgcatat gccgccacct   9240
cccaaggggg cgtgaatttt cgctgcttgt ccttttcctg catgctggtt gctcccattc   9300
ttaggtgaat ttaaggaggc caggctaaag ccgtcgcatg tctgattgct caccaggtaa   9360
atgtcgctaa tgttttccaa cgcgagaagg tgttgagcgc ggagctgagt gacgtgacaa   9420
catgggtatg cccaattgcc ccatgttggg aggacgaaaa tggtgacaag acagatggcc   9480
agaaatacac caacagcacg catgatgtct actggggatt tattctttag tgcgggggaa   9540
tacacggctt ttaatacgat tgagggcgtc tcctaacaag ttacatcact cctgcccttc   9600
ctcaccctca tctccatcac ctccttcatc tccgtcatct ccgtcatcac cctccgcggc   9660
agccccttcc accataggtg gaaaccaggg aggcaaatct actccatcgt caaagctgca   9720
cacagtcacc ctgatattgc aggtaggagc gggctttgtc ataacaaggt ccttaatcgc   9780
atccttcaaa acctcagcaa atatatgagt ttgtaaaaag accatgaaat aacagacaat   9840
ggactccctt agcgggccag gttgtgggcc gggtccaggg gccattccaa aggggagacg   9900
actcaatggt gtaagacgac attgtggaat agcaagggca gttcctcgcc ttaggttgta   9960
aagggaggtc ttactacctc catatacgaa cacaccggcg acccaagttc cttcgtcggt  10020
agtcctttct acgtgactcc tagccaggag agctcttaaa ccttctgcaa tgttctcaaa  10080
tttcgggttg gaacctcctt gaccacgatg ctttccaaac caccctcctt ttttgcgcct  10140
gcctccatca ccctgacccc ggggtccagt gcttgggcct tctcctgggt catctgcggg  10200
gccctgctct atcgctcccg gggcacgtc aggctcacca tctgggccac cttcttggtg  10260
gtattcaaaa taatcggctt cccctacagg gtggaaaaat ggccttctac ctggaggggg  10320
cctgcgcggt ggagacccgg atgatgatga ctgactactg ggactcctgg gcctcttttc  10380
tccacgtcca cgacctctcc ccctggctct ttcacgactt ccccccctgg ctctttcacg  10440
tcctctaccc cggcggcctc cactacctcc tcgaccccgg cctccactac ctcctcgacc  10500
ccggcctcca ctgcctcctc gaccccggcc tccacctcct gctcctgccc ctcctgctcc  10560
tgcccctcct cctgctcctg cccctcctgc ccctcctgct cctgcccctc ctgcccctcc  10620
tgctcctgcc cctcctgccc ctcctgctcc tgcccctcct gcccctcctc ctgctcctgc  10680
ccctcctgcc cctcctcctg ctcctgcccc tcctgcccct cctgctcctg cccctcctgc  10740
ccctcctgct cctgcccctc ctgcccctcc tgctcctgcc cctcctgctc ctgcccctcc  10800
tgctcctgcc cctcctgctc ctgcccctcc tgcccctcct gcccctcctc ctgctcctgc  10860
```

-continued

```
ccctcctgct cctgcccctc ctgcccctcc tgcccctcct gctcctgccc ctcctcctgc  10920
tcctgcccct cctgcccctc ctgcccctcc tcctgctcct gcccctcctg cccctcctcc  10980
tgctcctgcc cctcctcctg ctcctgcccc tcctgcccct cctgcccctc ctcctgctcc  11040
tgcccctcct gcccctcctc ctgctcctgc ccctcctcct gctcctgccc ctcctgcccc  11100
tcctgcccct cctcctgctc ctgcccctcc tcctgctcct gcccctcctg cccctcctgc  11160
ccctcctgcc cctcctcctg ctcctgcccc tcctcctgct cctgcccctc ctgctcctgc  11220
ccctcccgct cctgctcctg ctcctgttcc accgtgggtc cctttgcagc caatgcaact  11280
tggacgtttt tggggtctcc ggacaccatc tctatgtctt ggccctgatc ctgagccgcc  11340
cggggctcct ggtcttccgc ctcctcgtcc tcgtcctctt ccccgtcctc gtccatggtt  11400
atcacccct cttctttgag gtccactgcc gccggagcct tctggtccag atgtgtctcc  11460
cttctctcct aggccatttc caggtcctgt acctggcccc tcgtcagaca tgattcacac  11520
taaaagagat caatagacat ctttattaga cgacgctcag tgaatacagg gagtgcagac  11580
tcctgccccc tccaacagcc cccccaccct catccccttc atggtcgctg tcagacagat  11640
ccaggtctga aaattcccca tcctccgaac catcctcgtc ctcatcacca attactcgca  11700
gcccggaaaa ctcccgctga acatcctcaa gatttgcgtc ctgagcctca agccaggcct  11760
caaattcctc gtccccttt ttgctggacg gtagggatgg ggattctcgg gacccctcct  11820
cttcctcttc aaggtcacca gacagagatg ctactggggc aacggaagaa aagctgggtg  11880
cggcctgtga ggatcagctt atcgatgata agctgtcaaa catgagaatt cttgaagacg  11940
aaagggcctc gtgatacgcc tatttttata ggttaatgtc atgataataa tggtttctta  12000
gacgtcaggt ggcacttttc ggggaaatgt gcgcggaacc cctatttgtt tatttttcta  12060
aatacattca aatatgtatc cgctcatgag acaataaccc tgataaatgc ttcaataata  12120
ttgaaaaagg aagagtatga gtattcaaca tttccgtgtc gcccttattc cctttttgc  12180
ggcattttgc cttcctgttt ttgctcaccc agaaacgctg gtgaaagtaa aagatgctga  12240
agatcagttg ggtgcacgag tgggttacat cgaactggat ctcaacagcg gtaagatcct  12300
tgagagtttt cgccccgaag aacgttttcc aatgatgagc acttttaaag ttctgctatg  12360
tggcgcggta ttatcccgtg ttgacgccgg gcaagagcaa ctcggtcgcc gcatacacta  12420
ttctcagaat gacttggttg agtactcacc agtcacagaa aagcatctta cggatggcat  12480
gacagtaaga gaattatgca gtgctgccat aaccatgagt gataacactg cggccaactt  12540
acttctgaca acgatcggag gaccgaagga gctaaccgct tttttgcaca acatggggga  12600
tcatgtaact cgccttgatc gttgggaacc ggagctgaat gaagccatac caaacgacga  12660
gcgtgacacc acgatgcctg cagcaatggc aacaacgttg cgcaaactat taactggcga  12720
actacttact ctagcttccc ggcaacaatt aatagactgg atggaggcgg ataaagttgc  12780
aggaccactt ctgcgctcgg cccttccggc tggctggttt attgctgata aatctggagc  12840
cggtgagcgt gggtctcgcg gtatcattgc agcactgggg ccagatggta agccctcccg  12900
tatcgtagtt atctacacga cggggagtca ggcaactatg gatgaacgaa atagacagat  12960
cgctgagata ggtgcctcac tgattaagca ttggtaactg tcagaccaag tttactcata  13020
tatactttag attgatttaa aacttcattt ttaatttaaa aggatctagg tgaagatcct  13080
ttttgataat ctcatgacca aaatccctta acgtgagttt tcgttccact gagcgtcaga  13140
ccccgtagaa aagatcaaag gatcttcttg agatcctttt tttctgcgcg taatctgctg  13200
cttgcaaaca aaaaaaccac cgctaccagc ggtggtttgt ttgccggatc aagagctacc  13260
```

-continued

```
aactcttttt ccgaaggtaa ctggcttcag cagagcgcag ataccaaata ctgtccttct  13320
agtgtagccg tagttaggcc accacttcaa gaactctgta gcaccgccta catacctcgc  13380
tctgctaatc ctgttaccag tggctgctgc cagtggcgat aagtcgtgtc ttaccgggtt  13440
ggactcaaga cgatagttac cggataaggc gcagcggtcg ggctgaacgg ggggttcgtg  13500
cacacagccc agcttggagc gaacgaccta caccgaactg agatacctac agcgtgagct  13560
atgagaaagc gccacgcttc ccgaagggag aaaggcggac aggtatccgg taagcggcag  13620
ggtcggaaca ggagagcgca cgagggagct tccaggggga aacgcctggt atctttatag  13680
tcctgtcggg tttcgccacc tctgacttga gcgtcgattt ttgtgatgct cgtcaggggg  13740
gcggagccta tggaaaaacg ccagcaacgc ggccttttta cggttcctgg ccttttgctg  13800
cgccgcgtgc ggctgctgga gatggcggac gcgatggata tgttctgcca agggttggtt  13860
tgcgcattca cagttctccg caagaattga ttggctccaa ttcttggagt ggtgaatccg  13920
ttagcgaggt gccgccggct tccattcagg tcgaggtggc ccggctccat gcaccgcgac  13980
gcaacgcggg gaggcagaca aggtataggg cggcgcctac aatccatgcc aacccgttcc  14040
atgtgctcgc cgaggcggca taaatcgccg tgacgatcag cggtccagtg atcgaagtta  14100
ggctggtaag agccgcgagc gatccttgaa gctgtccctg atggtcgtca tctacctgcc  14160
tggacagcat ggcctgcaac gcgggcatcc cgatgccgcc ggaagcgaga agaatcataa  14220
tggggaaggc catccagcct cgcgtcgcga acgccagcaa gacgtagccc agcgcgtcgg  14280
ccgccatgcc ctgcttcatc cccgtggccc gttgctcgcg tttgctggcg gtgtccccgg  14340
aagaaatata tttgcatgtc tttagttcta tgatgacaca aaccccgccc agcgtcttgt  14400
cattggcgaa ttcgaacacg cagatgcagt cggggcggcg cggtcccagg tccacttcgc  14460
atattaaggt gacgcgtgtg gcctcgaaca ccgagcgacc ctgcagcgac ccgcttaaca  14520
gcgtcaacag cgtgccgcag atcccgggca atgagatatg aaaaagcctg aactcaccgc  14580
gacgtctgtc gagaagtttc tgatcgaaaa gttcgacagc gtctccgacc tgatgcagct  14640
ctcggagggc gaagaatctc gtgctttcag cttcgatgta ggagggcgtg gatatgtcct  14700
gcgggtaaat agctgcgccg atggtttcta caaagatcgt tagtgggatc ggcactttgc  14760
atcggccgcg ctccccgatt ccggaagtgc ttgacattgg ggaattcagc gagagcctga  14820
cctattgcat ctcccgccgt gcacagggtg tcacgttgca agacctgcct gaaaccgaac  14880
tgcccgctgt tctgcagccg gtcgcggagg ccatggatgc gatcgctgcg gccgatctta  14940
gccagacgag cgggttcggc ccattcggac cgcaaggaat cggtcaatac actacatggc  15000
gtgatttcat atgcgcgatt gctgatcccc atgtgtatca ctggcaaact gtgatggacg  15060
acaccgtcag tgcgtccgtc gcgcaggctc tcgatgagct gatgctttgg gccgaggact  15120
gccccgaagt ccggcacctc gtgcacgcgg atttcggctc caacaatgtc ctgacggaca  15180
atggccgcat aacagcggtc attgactgga gcgaggcgat gttcggggat tcccaatacg  15240
aggtcgccaa catcttcttc tggaggccgt ggttggcggg tatggagcag cagacgcgct  15300
acttcgagcg gaggcatccg gagcttgcag gatcgccgcg gctccgggcg tatatgctcc  15360
gcattggtct tgaccaactc tatcagagct tggttgacgg caatttcgat gatgcagctt  15420
gggcgcaggg tcgatgcgac gcaatcgtcc gatccggagc cgggactgtc gggcgtacac  15480
aaatcgcccg cagaagcgcg gccgtctgga ccgatggctg tgtagaagta ctcgccgata  15540
gtggaaacgg gagatggggg aggctaactg aaacacggaa ggagacaata ccggaaggaa  15600
```

-continued

```
cccgcgctat gacggcaata aaaagacaga ataaaacgca cgggtgttgg gtcgtttgtt  15660

cataaacgcg gggttcggtc ccagggctgg cactctgtcg ataccccacc gagaccccat  15720

tggggccaat acgcccgcgt ttcttccttt tccccacccc accccccaag ttcgggtgaa  15780

ggcccagggc tcgcagccaa cgtcggggcg gcaggccctg ccatagccac tggccccgtg  15840

ggttagggac ggggtccccc atggggaatg gtttatggtt cgtgggggtt attattttgg  15900

gcgttgcgtg ggtctggtc cacgactgga ctgagcagac agacccatgg tttttggatg  15960

gcctgggcat ggaccgcatg tactggcgcg acacgaacac cgggcgtctg tggctgccaa  16020

acacccccga cccccaaaaa ccaccgcgcg gatttctggc gtgccaagct agtcgaccaa  16080


<210> SEQ ID NO 49
<211> LENGTH: 32
<212> TYPE: DNA
<213> ORGANISM: Homo sapiens

<400> SEQUENCE: 49

cccggccgga ggggcagctt tgtggagatg gt                                 32


<210> SEQ ID NO 50
<211> LENGTH: 11
<212> TYPE: PRT
<213> ORGANISM: Homo sapiens

<400> SEQUENCE: 50

Pro Gly Arg Arg Gly Ser Phe Val Glu Met Val
1               5                   10


<210> SEQ ID NO 51
<211> LENGTH: 5
<212> TYPE: PRT
<213> ORGANISM: Homo sapiens

<400> SEQUENCE: 51

Val Asn Leu Asp Ala
1               5


<210> SEQ ID NO 52
<211> LENGTH: 9
<212> TYPE: PRT
<213> ORGANISM: Artificial
<220> FEATURE:
<223> OTHER INFORMATION: Synthetic oligopeptide substrate

<400> SEQUENCE: 52

Ser Glu Val Asn Leu Asp Ala Glu Phe
1               5


<210> SEQ ID NO 53
<211> LENGTH: 30
<212> TYPE: PRT
<213> ORGANISM: Artificial
<220> FEATURE:
<223> OTHER INFORMATION: Synthetic oligopeptide substrate

<400> SEQUENCE: 53

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30


<210> SEQ ID NO 54
```

-continued

<211> LENGTH: 5
<212> TYPE: PRT
<213> ORGANISM: Homo sapiens

<400> SEQUENCE: 54

Val Lys Met Asp Ala
1               5

<210> SEQ ID NO 55
<211> LENGTH: 24
<212> TYPE: PRT
<213> ORGANISM: Homo sapiens

<400> SEQUENCE: 55

Glu Thr Asp Glu Glu Pro Glu Glu Pro Gly Arg Arg Gly Ser Phe Val
1               5                   10                  15

Glu Met Val Asp Asn Leu Arg Gly
            20

<210> SEQ ID NO 56
<211> LENGTH: 15
<212> TYPE: PRT
<213> ORGANISM: Homo sapiens

<400> SEQUENCE: 56

Ile Ser Phe Ala Val Ser Ala Cys His Val His Asp Glu Phe Arg
1               5                   10                  15

<210> SEQ ID NO 57
<211> LENGTH: 419
<212> TYPE: PRT
<213> ORGANISM: Homo sapiens

<400> SEQUENCE: 57

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro

-continued

```
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala


<210> SEQ ID NO 58
<211> LENGTH: 407
<212> TYPE: PRT
<213> ORGANISM: Homo sapiens

<400> SEQUENCE: 58

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30

Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125

Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
```

-continued

```
145                 150                 155                 160

His Val Pro Asn Leu Phe Ser Leu Gln Leu Cys Gly Ala Gly Phe Pro
                165                 170                 175

Leu Asn Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn Ile Phe Pro Val Ile Ser Leu Tyr Leu Met
    290                 295                 300

Gly Glu Val Thr Asn Gln Ser Phe Arg Ile Thr Ile Leu Pro Gln Gln
305                 310                 315                 320

Tyr Leu Arg Pro Val Glu Asp Val Ala Thr Ser Gln Asp Asp Cys Tyr
                325                 330                 335

Lys Phe Ala Ile Ser Gln Ser Ser Thr Gly Thr Val Met Gly Ala Val
            340                 345                 350

Ile Met Glu Gly Phe Tyr Val Val Phe Asp Arg Ala Arg Lys Arg Ile
        355                 360                 365

Gly Phe Ala Val Ser Ala Cys His Val His Asp Glu Phe Arg Thr Ala
    370                 375                 380

Ala Val Glu Gly Pro Phe Val Thr Leu Asp Met Glu Asp Cys Gly Tyr
385                 390                 395                 400

Asn Ile Pro Gln Thr Asp Glu
                405


<210> SEQ ID NO 59
<211> LENGTH: 452
<212> TYPE: PRT
<213> ORGANISM: Homo sapiens

<400> SEQUENCE: 59

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110
```

-continued

```
Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu
    450


<210> SEQ ID NO 60
<211> LENGTH: 420
<212> TYPE: PRT
<213> ORGANISM: Homo sapiens

<400> SEQUENCE: 60

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30
```

-continued

```
Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys
            420
```

<210> SEQ ID NO 61
<211> LENGTH: 6

-continued

<212> TYPE: PRT
<213> ORGANISM: Artificial
<220> FEATURE:
<223> OTHER INFORMATION: Synthetic peptide inhibitor
<220> FEATURE:
<221> NAME/KEY: MISC_FEATURE
<222> LOCATION: (2)..(3)
<223> OTHER INFORMATION: Met and Ala are linked by hydroxyethylene molecule

<400> SEQUENCE: 61

Glu Val Met Ala Glu Phe
1 5

<210> SEQ ID NO 62
<211> LENGTH: 26
<212> TYPE: PRT
<213> ORGANISM: Homo sapiens

<400> SEQUENCE: 62

Leu Met Thr Ile Ala Tyr Val Met Ala Ala Ile Cys Ala Leu Phe Met
1 5 10 15

Leu Pro Leu Cys Leu Met Val Cys Gln Trp
20 25

<210> SEQ ID NO 63
<211> LENGTH: 33
<212> TYPE: PRT
<213> ORGANISM: Homo sapiens
<220> FEATURE:
<221> NAME/KEY: MISC_FEATURE
<222> LOCATION: (1)..(33)
<223> OTHER INFORMATION: P26-P4'sw peptide substrate

<400> SEQUENCE: 63

Cys Gly Gly Ala Asp Arg Gly Leu Thr Thr Arg Pro Gly Ser Gly Leu
1 5 10 15

Thr Asn Ile Lys Thr Glu Glu Ile Ser Glu Val Asn Leu Asp Ala Glu
20 25 30

Phe

<210> SEQ ID NO 64
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: P26-P1' peptide substrate with CGG linker

<400> SEQUENCE: 64

Cys Gly Gly Ala Asp Arg Gly Leu Thr Thr Arg Pro Gly Ser Gly Leu
1 5 10 15

Thr Asn Ile Lys Thr Glu Glu Ile Ser Glu Val Asn Leu
20 25

<210> SEQ ID NO 65
<211> LENGTH: 501
<212> TYPE: PRT
<213> ORGANISM: Homo sapiens

<400> SEQUENCE: 65

Met Ala Gln Ala Leu Pro Trp Leu Leu Leu Trp Met Gly Ala Gly Val
1 5 10 15

Leu Pro Ala His Gly Thr Gln His Gly Ile Arg Leu Pro Leu Arg Ser

-continued

```
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445
```

```
Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500


<210> SEQ ID NO 66
<211> LENGTH: 480
<212> TYPE: PRT
<213> ORGANISM: Homo sapiens

<400> SEQUENCE: 66

Thr Gln His Gly Ile Arg Leu Pro Leu Arg Ser Gly Leu Gly Gly Ala
1               5                   10                  15

Pro Leu Gly Leu Arg Leu Pro Arg Glu Thr Asp Glu Glu Pro Glu Glu
            20                  25                  30

Pro Gly Arg Arg Gly Ser Phe Val Glu Met Val Asp Asn Leu Arg Gly
        35                  40                  45

Lys Ser Gly Gln Gly Tyr Tyr Val Glu Met Thr Val Gly Ser Pro Pro
    50                  55                  60

Gln Thr Leu Asn Ile Leu Val Asp Thr Gly Ser Ser Asn Phe Ala Val
65                  70                  75                  80

Gly Ala Ala Pro His Pro Phe Leu His Arg Tyr Tyr Gln Arg Gln Leu
                85                  90                  95

Ser Ser Thr Tyr Arg Asp Leu Arg Lys Gly Val Tyr Val Pro Tyr Thr
            100                 105                 110

Gln Gly Lys Trp Glu Gly Glu Leu Gly Thr Asp Leu Val Ser Ile Pro
        115                 120                 125

His Gly Pro Asn Val Thr Val Arg Ala Asn Ile Ala Ala Ile Thr Glu
    130                 135                 140

Ser Asp Lys Phe Phe Ile Asn Gly Ser Asn Trp Glu Gly Ile Leu Gly
145                 150                 155                 160

Leu Ala Tyr Ala Glu Ile Ala Arg Pro Asp Asp Ser Leu Glu Pro Phe
                165                 170                 175

Phe Asp Ser Leu Val Lys Gln Thr His Val Pro Asn Leu Phe Ser Leu
            180                 185                 190

Gln Leu Cys Gly Ala Gly Phe Pro Leu Asn Gln Ser Glu Val Leu Ala
        195                 200                 205

Ser Val Gly Gly Ser Met Ile Ile Gly Gly Ile Asp His Ser Leu Tyr
    210                 215                 220

Thr Gly Ser Leu Trp Tyr Thr Pro Ile Arg Arg Glu Trp Tyr Tyr Glu
225                 230                 235                 240

Val Ile Ile Val Arg Val Glu Ile Asn Gly Gln Asp Leu Lys Met Asp
                245                 250                 255

Cys Lys Glu Tyr Asn Tyr Asp Lys Ser Ile Val Asp Ser Gly Thr Thr
            260                 265                 270

Asn Leu Arg Leu Pro Lys Lys Val Phe Glu Ala Ala Val Lys Ser Ile
        275                 280                 285

Lys Ala Ala Ser Ser Thr Glu Lys Phe Pro Asp Gly Phe Trp Leu Gly
    290                 295                 300

Glu Gln Leu Val Cys Trp Gln Ala Gly Thr Thr Pro Trp Asn Ile Phe
```

-continued

```
305                 310                 315                 320

Pro Val Ile Ser Leu Tyr Leu Met Gly Glu Val Thr Asn Gln Ser Phe
                325                 330                 335

Arg Ile Thr Ile Leu Pro Gln Gln Tyr Leu Arg Pro Val Glu Asp Val
            340                 345                 350

Ala Thr Ser Gln Asp Asp Cys Tyr Lys Phe Ala Ile Ser Gln Ser Ser
        355                 360                 365

Thr Gly Thr Val Met Gly Ala Val Ile Met Glu Gly Phe Tyr Val Val
    370                 375                 380

Phe Asp Arg Ala Arg Lys Arg Ile Gly Phe Ala Val Ser Ala Cys His
385                 390                 395                 400

Val His Asp Glu Phe Arg Thr Ala Ala Val Glu Gly Pro Phe Val Thr
                405                 410                 415

Leu Asp Met Glu Asp Cys Gly Tyr Asn Ile Pro Gln Thr Asp Glu Ser
            420                 425                 430

Thr Leu Met Thr Ile Ala Tyr Val Met Ala Ala Ile Cys Ala Leu Phe
        435                 440                 445

Met Leu Pro Leu Cys Leu Met Val Cys Gln Trp Arg Cys Leu Arg Cys
    450                 455                 460

Leu Arg Gln Gln His Asp Asp Phe Ala Asp Asp Ile Ser Leu Leu Lys
465                 470                 475                 480


<210> SEQ ID NO 67
<211> LENGTH: 444
<212> TYPE: PRT
<213> ORGANISM: Homo sapiens

<400> SEQUENCE: 67

Gly Ser Phe Val Glu Met Val Asp Asn Leu Arg Gly Lys Ser Gly Gln
1               5                   10                  15

Gly Tyr Tyr Val Glu Met Thr Val Gly Ser Pro Pro Gln Thr Leu Asn
            20                  25                  30

Ile Leu Val Asp Thr Gly Ser Ser Asn Phe Ala Val Gly Ala Ala Pro
        35                  40                  45

His Pro Phe Leu His Arg Tyr Tyr Gln Arg Gln Leu Ser Ser Thr Tyr
    50                  55                  60

Arg Asp Leu Arg Lys Gly Val Tyr Val Pro Tyr Thr Gln Gly Lys Trp
65                  70                  75                  80

Glu Gly Glu Leu Gly Thr Asp Leu Val Ser Ile Pro His Gly Pro Asn
                85                  90                  95

Val Thr Val Arg Ala Asn Ile Ala Ala Ile Thr Glu Ser Asp Lys Phe
            100                 105                 110

Phe Ile Asn Gly Ser Asn Trp Glu Gly Ile Leu Gly Leu Ala Tyr Ala
        115                 120                 125

Glu Ile Ala Arg Pro Asp Asp Ser Leu Glu Pro Phe Phe Asp Ser Leu
    130                 135                 140

Val Lys Gln Thr His Val Pro Asn Leu Phe Ser Leu Gln Leu Cys Gly
145                 150                 155                 160

Ala Gly Phe Pro Leu Asn Gln Ser Glu Val Leu Ala Ser Val Gly Gly
                165                 170                 175

Ser Met Ile Ile Gly Gly Ile Asp His Ser Leu Tyr Thr Gly Ser Leu
            180                 185                 190

Trp Tyr Thr Pro Ile Arg Arg Glu Trp Tyr Tyr Glu Val Ile Ile Val
        195                 200                 205
```

-continued

```
Arg Val Glu Ile Asn Gly Gln Asp Leu Lys Met Asp Cys Lys Glu Tyr
    210                 215                 220

Asn Tyr Asp Lys Ser Ile Val Asp Ser Gly Thr Thr Asn Leu Arg Leu
225                 230                 235                 240

Pro Lys Lys Val Phe Glu Ala Ala Val Lys Ser Ile Lys Ala Ala Ser
                245                 250                 255

Ser Thr Glu Lys Phe Pro Asp Gly Phe Trp Leu Gly Glu Gln Leu Val
            260                 265                 270

Cys Trp Gln Ala Gly Thr Thr Pro Trp Asn Ile Phe Pro Val Ile Ser
        275                 280                 285

Leu Tyr Leu Met Gly Glu Val Thr Asn Gln Ser Phe Arg Ile Thr Ile
    290                 295                 300

Leu Pro Gln Gln Tyr Leu Arg Pro Val Glu Asp Val Ala Thr Ser Gln
305                 310                 315                 320

Asp Asp Cys Tyr Lys Phe Ala Ile Ser Gln Ser Ser Thr Gly Thr Val
                325                 330                 335

Met Gly Ala Val Ile Met Glu Gly Phe Tyr Val Val Phe Asp Arg Ala
            340                 345                 350

Arg Lys Arg Ile Gly Phe Ala Val Ser Ala Cys His Val His Asp Glu
        355                 360                 365

Phe Arg Thr Ala Ala Val Glu Gly Pro Phe Val Thr Leu Asp Met Glu
    370                 375                 380

Asp Cys Gly Tyr Asn Ile Pro Gln Thr Asp Glu Ser Thr Leu Met Thr
385                 390                 395                 400

Ile Ala Tyr Val Met Ala Ala Ile Cys Ala Leu Phe Met Leu Pro Leu
                405                 410                 415

Cys Leu Met Val Cys Gln Trp Arg Cys Leu Arg Cys Leu Arg Gln Gln
            420                 425                 430

His Asp Asp Phe Ala Asp Asp Ile Ser Leu Leu Lys
        435                 440


<210> SEQ ID NO 68
<211> LENGTH: 395
<212> TYPE: PRT
<213> ORGANISM: Homo sapiens

<400> SEQUENCE: 68

Gly Ser Phe Val Glu Met Val Asp Asn Leu Arg Gly Lys Ser Gly Gln
1               5                   10                  15

Gly Tyr Tyr Val Glu Met Thr Val Gly Ser Pro Pro Gln Thr Leu Asn
            20                  25                  30

Ile Leu Val Asp Thr Gly Ser Ser Asn Phe Ala Val Gly Ala Ala Pro
        35                  40                  45

His Pro Phe Leu His Arg Tyr Tyr Gln Arg Gln Leu Ser Ser Thr Tyr
    50                  55                  60

Arg Asp Leu Arg Lys Gly Val Tyr Val Pro Tyr Thr Gln Gly Lys Trp
65                  70                  75                  80

Glu Gly Glu Leu Gly Thr Asp Leu Val Ser Ile Pro His Gly Pro Asn
                85                  90                  95

Val Thr Val Arg Ala Asn Ile Ala Ala Ile Thr Glu Ser Asp Lys Phe
            100                 105                 110

Phe Ile Asn Gly Ser Asn Trp Glu Gly Ile Leu Gly Leu Ala Tyr Ala
        115                 120                 125

Glu Ile Ala Arg Pro Asp Asp Ser Leu Glu Pro Phe Phe Asp Ser Leu
    130                 135                 140
```

-continued

```
Val Lys Gln Thr His Val Pro Asn Leu Phe Ser Leu Gln Leu Cys Gly
145                 150                 155                 160

Ala Gly Phe Pro Leu Asn Gln Ser Glu Val Leu Ala Ser Val Gly Gly
                165                 170                 175

Ser Met Ile Ile Gly Gly Ile Asp His Ser Leu Tyr Thr Gly Ser Leu
            180                 185                 190

Trp Tyr Thr Pro Ile Arg Arg Glu Trp Tyr Tyr Glu Val Ile Ile Val
        195                 200                 205

Arg Val Glu Ile Asn Gly Gln Asp Leu Lys Met Asp Cys Lys Glu Tyr
    210                 215                 220

Asn Tyr Asp Lys Ser Ile Val Asp Ser Gly Thr Thr Asn Leu Arg Leu
225                 230                 235                 240

Pro Lys Lys Val Phe Glu Ala Ala Val Lys Ser Ile Lys Ala Ala Ser
                245                 250                 255

Ser Thr Glu Lys Phe Pro Asp Gly Phe Trp Leu Gly Glu Gln Leu Val
            260                 265                 270

Cys Trp Gln Ala Gly Thr Thr Pro Trp Asn Ile Phe Pro Val Ile Ser
        275                 280                 285

Leu Tyr Leu Met Gly Glu Val Thr Asn Gln Ser Phe Arg Ile Thr Ile
    290                 295                 300

Leu Pro Gln Gln Tyr Leu Arg Pro Val Glu Asp Val Ala Thr Ser Gln
305                 310                 315                 320

Asp Asp Cys Tyr Lys Phe Ala Ile Ser Gln Ser Ser Thr Gly Thr Val
                325                 330                 335

Met Gly Ala Val Ile Met Glu Gly Phe Tyr Val Val Phe Asp Arg Ala
            340                 345                 350

Arg Lys Arg Ile Gly Phe Ala Val Ser Ala Cys His Val His Asp Glu
        355                 360                 365

Phe Arg Thr Ala Ala Val Glu Gly Pro Phe Val Thr Leu Asp Met Glu
    370                 375                 380

Asp Cys Gly Tyr Asn Ile Pro Gln Thr Asp Glu
385                 390                 395
```

<210> SEQ ID NO 69
<211> LENGTH: 439
<212> TYPE: PRT
<213> ORGANISM: Homo sapiens

<400> SEQUENCE: 69

```
Met Val Asp Asn Leu Arg Gly Lys Ser Gly Gln Gly Tyr Tyr Val Glu
1               5                   10                  15

Met Thr Val Gly Ser Pro Pro Gln Thr Leu Asn Ile Leu Val Asp Thr
            20                  25                  30

Gly Ser Ser Asn Phe Ala Val Gly Ala Ala Pro His Pro Phe Leu His
        35                  40                  45

Arg Tyr Tyr Gln Arg Gln Leu Ser Ser Thr Tyr Arg Asp Leu Arg Lys
    50                  55                  60

Gly Val Tyr Val Pro Tyr Thr Gln Gly Lys Trp Glu Gly Glu Leu Gly
65                  70                  75                  80

Thr Asp Leu Val Ser Ile Pro His Gly Pro Asn Val Thr Val Arg Ala
                85                  90                  95

Asn Ile Ala Ala Ile Thr Glu Ser Asp Lys Phe Phe Ile Asn Gly Ser
            100                 105                 110

Asn Trp Glu Gly Ile Leu Gly Leu Ala Tyr Ala Glu Ile Ala Arg Pro
```

-continued

```
        115                 120                 125

Asp Asp Ser Leu Glu Pro Phe Phe Asp Ser Leu Val Lys Gln Thr His
    130                 135                 140

Val Pro Asn Leu Phe Ser Leu Gln Leu Cys Gly Ala Gly Phe Pro Leu
145                 150                 155                 160

Asn Gln Ser Glu Val Leu Ala Ser Val Gly Gly Ser Met Ile Ile Gly
                165                 170                 175

Gly Ile Asp His Ser Leu Tyr Thr Gly Ser Leu Trp Tyr Thr Pro Ile
            180                 185                 190

Arg Arg Glu Trp Tyr Tyr Glu Val Ile Ile Val Arg Val Glu Ile Asn
        195                 200                 205

Gly Gln Asp Leu Lys Met Asp Cys Lys Glu Tyr Asn Tyr Asp Lys Ser
    210                 215                 220

Ile Val Asp Ser Gly Thr Thr Asn Leu Arg Leu Pro Lys Lys Val Phe
225                 230                 235                 240

Glu Ala Ala Val Lys Ser Ile Lys Ala Ala Ser Ser Thr Glu Lys Phe
                245                 250                 255

Pro Asp Gly Phe Trp Leu Gly Glu Gln Leu Val Cys Trp Gln Ala Gly
            260                 265                 270

Thr Thr Pro Trp Asn Ile Phe Pro Val Ile Ser Leu Tyr Leu Met Gly
        275                 280                 285

Glu Val Thr Asn Gln Ser Phe Arg Ile Thr Ile Leu Pro Gln Gln Tyr
    290                 295                 300

Leu Arg Pro Val Glu Asp Val Ala Thr Ser Gln Asp Asp Cys Tyr Lys
305                 310                 315                 320

Phe Ala Ile Ser Gln Ser Ser Thr Gly Thr Val Met Gly Ala Val Ile
                325                 330                 335

Met Glu Gly Phe Tyr Val Val Phe Asp Arg Ala Arg Lys Arg Ile Gly
            340                 345                 350

Phe Ala Val Ser Ala Cys His Val His Asp Glu Phe Arg Thr Ala Ala
        355                 360                 365

Val Glu Gly Pro Phe Val Thr Leu Asp Met Glu Asp Cys Gly Tyr Asn
    370                 375                 380

Ile Pro Gln Thr Asp Glu Ser Thr Leu Met Thr Ile Ala Tyr Val Met
385                 390                 395                 400

Ala Ala Ile Cys Ala Leu Phe Met Leu Pro Leu Cys Leu Met Val Cys
                405                 410                 415

Gln Trp Arg Cys Leu Arg Cys Leu Arg Gln Gln His Asp Asp Phe Ala
            420                 425                 430

Asp Asp Ile Ser Leu Leu Lys
        435


<210> SEQ ID NO 70
<211> LENGTH: 390
<212> TYPE: PRT
<213> ORGANISM: Homo sapiens

<400> SEQUENCE: 70

Met Val Asp Asn Leu Arg Gly Lys Ser Gly Gln Gly Tyr Tyr Val Glu
1               5                   10                  15

Met Thr Val Gly Ser Pro Pro Gln Thr Leu Asn Ile Leu Val Asp Thr
            20                  25                  30

Gly Ser Ser Asn Phe Ala Val Gly Ala Ala Pro His Pro Phe Leu His
        35                  40                  45
```

-continued

```
Arg Tyr Tyr Gln Arg Gln Leu Ser Ser Thr Tyr Arg Asp Leu Arg Lys
    50                  55                  60

Gly Val Tyr Val Pro Tyr Thr Gln Gly Lys Trp Glu Gly Glu Leu Gly
65                  70                  75                  80

Thr Asp Leu Val Ser Ile Pro His Gly Pro Asn Val Thr Val Arg Ala
                85                  90                  95

Asn Ile Ala Ala Ile Thr Glu Ser Asp Lys Phe Phe Ile Asn Gly Ser
            100                 105                 110

Asn Trp Glu Gly Ile Leu Gly Leu Ala Tyr Ala Glu Ile Ala Arg Pro
        115                 120                 125

Asp Asp Ser Leu Glu Pro Phe Phe Asp Ser Leu Val Lys Gln Thr His
    130                 135                 140

Val Pro Asn Leu Phe Ser Leu Gln Leu Cys Gly Ala Gly Phe Pro Leu
145                 150                 155                 160

Asn Gln Ser Glu Val Leu Ala Ser Val Gly Gly Ser Met Ile Ile Gly
                165                 170                 175

Gly Ile Asp His Ser Leu Tyr Thr Gly Ser Leu Trp Tyr Thr Pro Ile
            180                 185                 190

Arg Arg Glu Trp Tyr Tyr Glu Val Ile Ile Val Arg Val Glu Ile Asn
        195                 200                 205

Gly Gln Asp Leu Lys Met Asp Cys Lys Glu Tyr Asn Tyr Asp Lys Ser
    210                 215                 220

Ile Val Asp Ser Gly Thr Thr Asn Leu Arg Leu Pro Lys Lys Val Phe
225                 230                 235                 240

Glu Ala Ala Val Lys Ser Ile Lys Ala Ala Ser Ser Thr Glu Lys Phe
                245                 250                 255

Pro Asp Gly Phe Trp Leu Gly Glu Gln Leu Val Cys Trp Gln Ala Gly
            260                 265                 270

Thr Thr Pro Trp Asn Ile Phe Pro Val Ile Ser Leu Tyr Leu Met Gly
        275                 280                 285

Glu Val Thr Asn Gln Ser Phe Arg Ile Thr Ile Leu Pro Gln Gln Tyr
    290                 295                 300

Leu Arg Pro Val Glu Asp Val Ala Thr Ser Gln Asp Asp Cys Tyr Lys
305                 310                 315                 320

Phe Ala Ile Ser Gln Ser Ser Thr Gly Thr Val Met Gly Ala Val Ile
                325                 330                 335

Met Glu Gly Phe Tyr Val Val Phe Asp Arg Ala Arg Lys Arg Ile Gly
            340                 345                 350

Phe Ala Val Ser Ala Cys His Val His Asp Glu Phe Arg Thr Ala Ala
        355                 360                 365

Val Glu Gly Pro Phe Val Thr Leu Asp Met Glu Asp Cys Gly Tyr Asn
    370                 375                 380

Ile Pro Gln Thr Asp Glu
385                 390


<210> SEQ ID NO 71
<211> LENGTH: 374
<212> TYPE: PRT
<213> ORGANISM: Homo sapiens

<400> SEQUENCE: 71

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30
```

-continued

```
Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125

Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Asn Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn Ile Phe Pro Val Ile Ser Leu Tyr Leu Met
    290                 295                 300

Gly Glu Val Thr Asn Gln Ser Phe Arg Ile Thr Ile Leu Pro Gln Gln
305                 310                 315                 320

Tyr Leu Arg Pro Val Glu Asp Val Ala Thr Ser Gln Asp Asp Cys Tyr
                325                 330                 335

Lys Phe Ala Ile Ser Gln Ser Ser Thr Gly Thr Val Met Gly Ala Val
            340                 345                 350

Ile Met Glu Gly Phe Tyr Val Val Phe Asp Arg Ala Arg Lys Arg Ile
        355                 360                 365

Gly Phe Ala Val Ser Ala
    370
```

<210> SEQ ID NO 72
<211> LENGTH: 14
<212> TYPE: PRT
<213> ORGANISM: Artificial
<220> FEATURE:
<223> OTHER INFORMATION: Synthetic P10-P4' staD-V peptide inhibitor
<220> FEATURE:
<221> NAME/KEY: MISC_FEATURE
<222> LOCATION: (10)..(10)
<223> OTHER INFORMATION: Xaa = statine moiety molecule -continued

<400> SEQUENCE: 72

```
Lys Thr Glu Glu Ile Ser Glu Val Asn Xaa Val Ala Glu Phe
1               5                   10
```

<210> SEQ ID NO 73
<211> LENGTH: 9
<212> TYPE: PRT
<213> ORGANISM: Artificial
<220> FEATURE:
<223> OTHER INFORMATION: Synthetic P4-P4' staD-V peptide inhibitor
<220> FEATURE:
<221> NAME/KEY: MOD_RES
<222> LOCATION: (5)..(5)
<223> OTHER INFORMATION: Xaa = statine molecule

<400> SEQUENCE: 73

```
Ser Glu Val Asn Xaa Val Ala Glu Phe
1               5
```

<210> SEQ ID NO 74
<211> LENGTH: 431
<212> TYPE: PRT
<213> ORGANISM: Homo sapiens

<400> SEQUENCE: 74

```
Thr Gln His Gly Ile Arg Leu Pro Leu Arg Ser Gly Leu Gly Gly Ala
1               5                   10                  15

Pro Leu Gly Leu Arg Leu Pro Arg Glu Thr Asp Glu Glu Pro Glu Glu
            20                  25                  30

Pro Gly Arg Arg Gly Ser Phe Val Glu Met Val Asp Asn Leu Arg Gly
        35                  40                  45

Lys Ser Gly Gln Gly Tyr Tyr Val Glu Met Thr Val Gly Ser Pro Pro
    50                  55                  60

Gln Thr Leu Asn Ile Leu Val Asp Thr Gly Ser Ser Asn Phe Ala Val
65                  70                  75                  80

Gly Ala Ala Pro His Pro Phe Leu His Arg Tyr Tyr Gln Arg Gln Leu
                85                  90                  95

Ser Ser Thr Tyr Arg Asp Leu Arg Lys Gly Val Tyr Val Pro Tyr Thr
            100                 105                 110

Gln Gly Lys Trp Glu Gly Glu Leu Gly Thr Asp Leu Val Ser Ile Pro
        115                 120                 125

His Gly Pro Asn Val Thr Val Arg Ala Asn Ile Ala Ala Ile Thr Glu
    130                 135                 140

Ser Asp Lys Phe Phe Ile Asn Gly Ser Asn Trp Glu Gly Ile Leu Gly
145                 150                 155                 160

Leu Ala Tyr Ala Glu Ile Ala Arg Pro Asp Asp Ser Leu Glu Pro Phe
                165                 170                 175

Phe Asp Ser Leu Val Lys Gln Thr His Val Pro Asn Leu Phe Ser Leu
            180                 185                 190

Gln Leu Cys Gly Ala Gly Phe Pro Leu Asn Gln Ser Glu Val Leu Ala
        195                 200                 205

Ser Val Gly Gly Ser Met Ile Ile Gly Gly Ile Asp His Ser Leu Tyr
    210                 215                 220

Thr Gly Ser Leu Trp Tyr Thr Pro Ile Arg Arg Glu Trp Tyr Tyr Glu
225                 230                 235                 240

Val Ile Ile Val Arg Val Glu Ile Asn Gly Gln Asp Leu Lys Met Asp
                245                 250                 255

Cys Lys Glu Tyr Asn Tyr Asp Lys Ser Ile Val Asp Ser Gly Thr Thr
```

-continued

```
            260                 265                 270

Asn Leu Arg Leu Pro Lys Lys Val Phe Glu Ala Ala Val Lys Ser Ile
        275                 280                 285

Lys Ala Ala Ser Ser Thr Glu Lys Phe Pro Asp Gly Phe Trp Leu Gly
    290                 295                 300

Glu Gln Leu Val Cys Trp Gln Ala Gly Thr Thr Pro Trp Asn Ile Phe
305                 310                 315                 320

Pro Val Ile Ser Leu Tyr Leu Met Gly Glu Val Thr Asn Gln Ser Phe
                325                 330                 335

Arg Ile Thr Ile Leu Pro Gln Gln Tyr Leu Arg Pro Val Glu Asp Val
            340                 345                 350

Ala Thr Ser Gln Asp Asp Cys Tyr Lys Phe Ala Ile Ser Gln Ser Ser
        355                 360                 365

Thr Gly Thr Val Met Gly Ala Val Ile Met Glu Gly Phe Tyr Val Val
    370                 375                 380

Phe Asp Arg Ala Arg Lys Arg Ile Gly Phe Ala Val Ser Ala Cys His
385                 390                 395                 400

Val His Asp Glu Phe Arg Thr Ala Ala Val Glu Gly Pro Phe Val Thr
                405                 410                 415

Leu Asp Met Glu Asp Cys Gly Tyr Asn Ile Pro Gln Thr Asp Glu
            420                 425                 430


<210> SEQ ID NO 75
<211> LENGTH: 361
<212> TYPE: PRT
<213> ORGANISM: Homo sapiens

<400> SEQUENCE: 75

Met Val Asp Asn Leu Arg Gly Lys Ser Gly Gln Gly Tyr Tyr Val Glu
1               5                   10                  15

Met Thr Val Gly Ser Pro Pro Gln Thr Leu Asn Ile Leu Val Asp Thr
            20                  25                  30

Gly Ser Ser Asn Phe Ala Val Gly Ala Ala Pro His Pro Phe Leu His
        35                  40                  45

Arg Tyr Tyr Gln Arg Gln Leu Ser Ser Thr Tyr Arg Asp Leu Arg Lys
    50                  55                  60

Gly Val Tyr Val Pro Tyr Thr Gln Gly Lys Trp Glu Gly Glu Leu Gly
65                  70                  75                  80

Thr Asp Leu Val Ser Ile Pro His Gly Pro Asn Val Thr Val Arg Ala
                85                  90                  95

Asn Ile Ala Ala Ile Thr Glu Ser Asp Lys Phe Phe Ile Asn Gly Ser
            100                 105                 110

Asn Trp Glu Gly Ile Leu Gly Leu Ala Tyr Ala Glu Ile Ala Arg Pro
        115                 120                 125

Asp Asp Ser Leu Glu Pro Phe Phe Asp Ser Leu Val Lys Gln Thr His
    130                 135                 140

Val Pro Asn Leu Phe Ser Leu Gln Leu Cys Gly Ala Gly Phe Pro Leu
145                 150                 155                 160

Asn Gln Ser Glu Val Leu Ala Ser Val Gly Gly Ser Met Ile Ile Gly
                165                 170                 175

Gly Ile Asp His Ser Leu Tyr Thr Gly Ser Leu Trp Tyr Thr Pro Ile
            180                 185                 190

Arg Arg Glu Trp Tyr Tyr Glu Val Ile Ile Val Arg Val Glu Ile Asn
        195                 200                 205
```

-continued

```
Gly Gln Asp Leu Lys Met Asp Cys Lys Glu Tyr Asn Tyr Asp Lys Ser
    210                 215                 220

Ile Val Asp Ser Gly Thr Thr Asn Leu Arg Leu Pro Lys Lys Val Phe
225                 230                 235                 240

Glu Ala Ala Val Lys Ser Ile Lys Ala Ala Ser Ser Thr Glu Lys Phe
                245                 250                 255

Pro Asp Gly Phe Trp Leu Gly Glu Gln Leu Val Cys Trp Gln Ala Gly
            260                 265                 270

Thr Thr Pro Trp Asn Ile Phe Pro Val Ile Ser Leu Tyr Leu Met Gly
        275                 280                 285

Glu Val Thr Asn Gln Ser Phe Arg Ile Thr Ile Leu Pro Gln Gln Tyr
    290                 295                 300

Leu Arg Pro Val Glu Asp Val Ala Thr Ser Gln Asp Asp Cys Tyr Lys
305                 310                 315                 320

Phe Ala Ile Ser Gln Ser Ser Thr Gly Thr Val Met Gly Ala Val Ile
                325                 330                 335

Met Glu Gly Phe Tyr Val Val Phe Asp Arg Ala Arg Lys Arg Ile Gly
            340                 345                 350

Phe Ala Val Ser Ala Cys His Val His
        355                 360
```

<210> SEQ ID NO 76
<211> LENGTH: 63
<212> TYPE: DNA
<213> ORGANISM: Homo sapiens
<220> FEATURE:
<221> NAME/KEY: misc_feature
<222> LOCATION: (1)..(63)
<223> OTHER INFORMATION: N = A, C, G, or T

<400> SEQUENCE: 76

```
garacngayg argarccnga rgarccnggn mgnmgnggnw snttygtnga ratggtngay     60

aay                                                                   63
```

<210> SEQ ID NO 77
<211> LENGTH: 21
<212> TYPE: PRT
<213> ORGANISM: Homo sapiens

<400> SEQUENCE: 77

```
Glu Thr Asp Glu Glu Pro Glu Glu Pro Gly Arg Arg Gly Ser Phe Val
1               5                   10                  15

Glu Met Val Asp Asn
            20
```

<210> SEQ ID NO 78
<211> LENGTH: 7
<212> TYPE: PRT
<213> ORGANISM: Artificial
<220> FEATURE:
<223> OTHER INFORMATION: Synthetic peptide inhibitor P3-p4' XD-V
<220> FEATURE:
<221> NAME/KEY: misc_feature
<222> LOCATION: (3)..(3)
<223> OTHER INFORMATION: Xaa can be any naturally occurring amino acid

<400> SEQUENCE: 78

```
Val Met Xaa Val Ala Glu Phe
1               5
```

<210> SEQ ID NO 79

-continued

<211> LENGTH: 11
<212> TYPE: PRT
<213> ORGANISM: Homo sapiens

<400> SEQUENCE: 79

Pro Glu Glu Pro Gly Arg Arg Gly Ser Phe Val
1 5 10

<210> SEQ ID NO 80
<211> LENGTH: 419
<212> TYPE: DNA
<213> ORGANISM: Artificial
<220> FEATURE:
<223> OTHER INFORMATION: Synthetic nucleotide insert in pCF vector

<400> SEQUENCE: 80
ctgttgggct cgcggttgag gacaaactct tcgcggtctt tccagtactc ttggatcgga 60
aacccgtcgg cctccgaacg gtactccgcc accgagggac ctgagcgagt ccgcatcgac 120
cggatcggaa aacctctcga ctgttggggt gagtactccc tctcaaaagc gggcatgact 180
tctgcgctaa gattgtcagt ttccaaaaac gaggaggatt tgatattcac ctggcccgcg 240
gtgatgcctt tgagggtggc cgcgtccatc tggtcagaaa agacaatctt tttgttgtca 300
agcttgaggt gtggcaggct tgagatctgg ccatacactt gagtgacaat gacatccact 360
ttgcctttct ctccacaggt gtccactccc aggtccaact gcaggtcgac tctagaccc 419

<210> SEQ ID NO 81
<211> LENGTH: 408
<212> TYPE: PRT
<213> ORGANISM: Artificial
<220> FEATURE:
<223> OTHER INFORMATION: Synthetic pBS/MuImPain E17 #11 construct

<400> SEQUENCE: 81

Ser Ile Ser Leu Ile Glu Pro Gly Arg Arg Gly Ser Phe Val Glu Met
1 5 10 15

Val Asn Asn Leu Arg Gly Lys Ser Gly Gln Gly Tyr Tyr Val Glu Met
20 25 30

Thr Val Gly Ser Pro Pro Gln Thr Leu Asn Ile Leu Val Asp Thr Gly
35 40 45

Ser Ser Asn Phe Ala Val Gly Ala Ala Pro His Pro Phe Leu His Arg
50 55 60

Tyr Tyr Gln Arg Gln Leu Ser Ser Thr Tyr Arg Asp Leu Arg Lys Gly
65 70 75 80

Val Tyr Val Pro Tyr Thr Gln Gly Lys Trp Glu Gly Glu Leu Gly Thr
85 90 95

Asp Leu Val Ser Ile Pro His Gly Pro Asn Val Thr Val Arg Ala Asn
100 105 110

Ile Ala Ala Ile Thr Glu Ser Asp Lys Phe Phe Ile Asn Gly Ser Asn
115 120 125

Trp Glu Gly Ile Leu Gly Leu Ala Tyr Ala Glu Ile Ala Arg Pro Asp
130 135 140

Asp Ser Leu Glu Pro Phe Phe Asp Ser Leu Val Lys Gln Thr His Ile
145 150 155 160

Pro Asn Ile Phe Ser Leu Gln Leu Cys Gly Ala Gly Phe Pro Leu Asn
165 170 175

Gln Thr Glu Ala Leu Ala Ser Val Gly Gly Ser Met Ile Ile Gly Gly
180 185 190

-continued

```
Ile Asp His Ser Leu Tyr Thr Gly Ser Leu Trp Tyr Thr Pro Ile Arg
        195                 200                 205

Arg Glu Trp Tyr Tyr Glu Val Ile Ile Val Arg Val Glu Ile Asn Gly
    210                 215                 220

Gln Asp Leu Lys Met Asp Cys Lys Glu Tyr Asn Tyr Asp Lys Ser Ile
225                 230                 235                 240

Val Asp Ser Gly Thr Thr Asn Leu Arg Leu Pro Lys Lys Val Phe Glu
                245                 250                 255

Ala Ala Val Lys Ser Ile Lys Ala Ala Ser Ser Thr Glu Lys Phe Pro
            260                 265                 270

Asp Gly Phe Trp Leu Gly Glu Gln Leu Val Cys Trp Gln Ala Gly Thr
        275                 280                 285

Thr Pro Trp Asn Ile Phe Pro Val Ile Ser Leu Tyr Leu Met Gly Glu
    290                 295                 300

Val Thr Asn Gln Ser Phe Arg Ile Thr Ile Leu Pro Gln Gln Tyr Leu
305                 310                 315                 320

Arg Pro Val Glu Asp Val Ala Thr Ser Gln Asp Asp Cys Tyr Lys Phe
                325                 330                 335

Ala Val Ser Gln Ser Ser Thr Gly Thr Val Met Gly Ala Val Ile Met
            340                 345                 350

Glu Gly Phe Tyr Val Val Phe Asp Arg Ala Arg Lys Arg Ile Gly Phe
        355                 360                 365

Ala Val Ser Ala Cys His Val His Asp Glu Phe Arg Thr Ala Ala Val
    370                 375                 380

Glu Gly Pro Phe Val Thr Ala Asp Met Glu Asp Cys Gly Tyr Asn Asn
385                 390                 395                 400

Arg Ile Pro Ala Ala Arg Gly Ile
                405


<210> SEQ ID NO 82
<211> LENGTH: 401
<212> TYPE: PRT
<213> ORGANISM: Artificial
<220> FEATURE:
<223> OTHER INFORMATION: Synthetic pBS/MuImPain E17 #14 construct

<400> SEQUENCE: 82

Lys Leu Asp Glu Pro Gly Arg Arg Gly Ser Phe Val Glu Met Val Asp
1               5                   10                  15

Asn Leu Arg Gly Lys Ser Gly Gln Gly Tyr Tyr Val Glu Met Thr Val
            20                  25                  30

Gly Ser Pro Pro Gln Thr Leu Asn Ile Leu Val Asp Thr Gly Ser Ser
        35                  40                  45

Asn Phe Ala Val Gly Ala Ala Pro His Pro Phe Leu His Arg Tyr Tyr
    50                  55                  60

Gln Arg Gln Leu Ser Ser Thr Tyr Arg Asp Leu Arg Lys Gly Val Tyr
65                  70                  75                  80

Val Pro Tyr Thr Gln Gly Lys Trp Glu Gly Glu Leu Gly Thr Asp Leu
                85                  90                  95

Val Ser Ile Pro His Gly Pro Asn Val Thr Val Arg Ala Asn Ile Ala
            100                 105                 110

Ala Ile Thr Glu Ser Asp Lys Phe Phe Ile Asn Gly Ser Asn Trp Glu
        115                 120                 125

Gly Ile Leu Gly Leu Ala Tyr Ala Glu Ile Ala Arg Pro Asp Asp Ser
    130                 135                 140
```

-continued

```
Leu Glu Pro Phe Phe Asp Ser Leu Val Lys Gln Thr His Ile Pro Asn
145                 150                 155                 160

Ile Phe Ser Leu Gln Leu Cys Gly Ala Gly Phe Pro Leu Asn Gln Thr
                165                 170                 175

Glu Ala Leu Ala Ser Val Gly Gly Ser Met Ile Ile Gly Gly Ile Asp
            180                 185                 190

His Ser Leu Tyr Thr Gly Ser Leu Trp Tyr Thr Pro Ile Arg Arg Glu
        195                 200                 205

Trp Tyr Tyr Glu Val Ile Ile Val Arg Val Glu Ile Asn Gly Gln Asp
    210                 215                 220

Leu Lys Met Asp Cys Lys Glu Tyr Asn Tyr Asp Lys Ser Ile Val Asp
225                 230                 235                 240

Ser Gly Thr Thr Asn Leu Arg Leu Pro Lys Lys Val Phe Glu Ala Ala
                245                 250                 255

Val Lys Ser Ile Lys Ala Ala Ser Ser Thr Glu Lys Phe Pro Asp Gly
            260                 265                 270

Phe Trp Leu Gly Glu Gln Leu Val Cys Trp Gln Ala Gly Thr Thr Pro
        275                 280                 285

Trp Asn Ile Phe Pro Val Ile Ser Leu Tyr Leu Met Gly Glu Val Thr
    290                 295                 300

Asn Gln Ser Phe Arg Ile Thr Ile Leu Pro Gln Gln Tyr Leu Arg Pro
305                 310                 315                 320

Val Glu Asp Val Ala Thr Ser Gln Asp Asp Cys Tyr Lys Phe Ala Val
                325                 330                 335

Ser Gln Ser Ser Thr Gly Thr Val Met Gly Ala Val Ile Met Glu Gly
            340                 345                 350

Phe Tyr Val Val Phe Asp Arg Ala Arg Lys Arg Ile Gly Phe Ala Val
        355                 360                 365

Ser Ala Cys His Val His Asp Glu Phe Arg Thr Ala Ala Val Glu Gly
    370                 375                 380

Pro Phe Val Thr Ala Asp Met Glu Asp Cys Gly Tyr Asn Asn Arg Ile
385                 390                 395                 400

Gln
```

<210> SEQ ID NO 83
<211> LENGTH: 231
<212> TYPE: PRT
<213> ORGANISM: Artificial
<220> FEATURE:
<223> OTHER INFORMATION: Synthetic pBS/MuImPain E17 Brain #17 construct

<400> SEQUENCE: 83

```
Phe Val Glu Met Val Asp Asn Leu Arg Gly Lys Ser Gly Gln Gly Tyr
1               5                   10                  15

Tyr Val Glu Met Thr Val Gly Ser Pro Pro Gln Thr Leu Asn Ile Leu
            20                  25                  30

Val Asp Thr Gly Ser Ser Asn Phe Ala Val Gly Ala Ala Pro His Pro
        35                  40                  45

Phe Leu His Arg Tyr Tyr Gln Arg Gln Leu Ser Ser Thr Tyr Arg Asp
    50                  55                  60

Leu Arg Lys Gly Val Tyr Val Pro Tyr Thr Gln Gly Lys Trp Glu Gly
65                  70                  75                  80

Glu Leu Gly Thr Asp Leu Val Ser Ile Pro His Gly Pro Asn Val Thr
                85                  90                  95

Val Arg Ala Asn Ile Ala Ala Ile Thr Glu Ser Asp Lys Phe Phe Val
```

-continued

```
            100                 105                 110

Asn Gly Ser Asn Trp Glu Gly Ile Leu Gly Leu Ala Tyr Ala Glu Ile
        115                 120                 125

Ala Arg Pro Asp Asp Ser Leu Glu Pro Phe Phe Asp Ser Leu Val Lys
    130                 135                 140

Gln Thr His Ile Pro Asn Ile Phe Ser Leu Gln Leu Cys Gly Ala Gly
145                 150                 155                 160

Phe Pro Leu Asn Gln Thr Glu Ala Leu Ala Ser Val Gly Gly Ser Met
                165                 170                 175

Ile Ile Gly Gly Ile Asp His Ser Leu Tyr Thr Gly Ser Leu Trp Tyr
            180                 185                 190

Thr Pro Ile Arg Arg Glu Trp Tyr Tyr Glu Val Ile Ile Val Arg Val
        195                 200                 205

Glu Ile Asn Gly Gln Asp Leu Lys Met Asp Cys Lys Glu Tyr Asn Tyr
    210                 215                 220

Asp Lys Ser Ile Val Asp Ser
225                 230


<210> SEQ ID NO 84
<211> LENGTH: 380
<212> TYPE: PRT
<213> ORGANISM: Artificial
<220> FEATURE:
<223> OTHER INFORMATION: Synthetic pBS/MuImPain E17 Brain #15 construct

<400> SEQUENCE: 84

Phe Val Glu Met Val Asp Asn Leu Arg Gly Lys Ser Gly Gln Gly Tyr
1               5                   10                  15

Tyr Val Glu Met Thr Val Gly Ser Pro Pro Gln Thr Leu Asn Ile Leu
            20                  25                  30

Val Asp Thr Gly Ser Ser Asn Phe Ala Val Gly Ala Ala Pro His Pro
        35                  40                  45

Phe Leu His Arg Tyr Tyr Gln Arg Gln Leu Ser Ser Thr Tyr Arg Asp
    50                  55                  60

Leu Arg Lys Gly Val Tyr Val Pro Tyr Thr Gln Gly Lys Trp Glu Gly
65                  70                  75                  80

Glu Leu Gly Thr Asp Leu Val Ser Ile Pro His Gly Pro Asn Val Thr
                85                  90                  95

Val Arg Ala Asn Ile Ala Ala Ile Thr Glu Ser Asp Lys Phe Phe Ile
            100                 105                 110

Asn Gly Ser Asn Trp Glu Gly Ile Leu Gly Leu Ala Tyr Ala Glu Ile
        115                 120                 125

Ala Arg Pro Asp Asp Ser Leu Glu Pro Phe Phe Asp Ser Leu Val Lys
    130                 135                 140

Gln Thr His Ile Pro Asn Ile Phe Ser Leu Gln Leu Cys Gly Ala Gly
145                 150                 155                 160

Phe Pro Leu Asn Gln Thr Glu Ala Leu Ala Ser Val Gly Gly Ser Met
                165                 170                 175

Ile Ile Gly Gly Ile Asp His Ser Leu Tyr Thr Gly Ser Leu Trp Tyr
            180                 185                 190

Thr Pro Ile Arg Arg Glu Trp Tyr Tyr Glu Val Ile Ile Val Arg Val
        195                 200                 205

Glu Ile Asn Gly Gln Asp Leu Lys Met Asp Cys Lys Glu Tyr Asn Tyr
    210                 215                 220

Asp Lys Ser Ile Val Asp Ser Gly Thr Thr Asn Leu Arg Leu Pro Lys
```

-continued

```
225                 230                 235                 240

Lys Val Phe Glu Ala Ala Val Lys Ser Ile Lys Ala Ala Ser Ser Thr
                245                 250                 255

Glu Lys Phe Pro Asp Gly Phe Trp Leu Gly Glu Gln Leu Val Cys Trp
            260                 265                 270

Gln Ala Gly Thr Thr Pro Trp Asn Ile Phe Pro Val Ile Ser Leu Tyr
        275                 280                 285

Leu Met Gly Glu Val Thr Asn Gln Ser Phe Arg Ile Thr Ile Leu Pro
    290                 295                 300

Gln Gln Tyr Leu Arg Pro Val Glu Asp Val Ala Thr Ser Gln Asp Asp
305                 310                 315                 320

Cys Tyr Lys Phe Ala Val Ser Gln Ser Ser Thr Gly Thr Val Met Gly
                325                 330                 335

Ala Val Ile Met Glu Gly Phe Tyr Val Val Phe Asp Arg Ala Arg Lys
            340                 345                 350

Arg Ile Gly Phe Ala Val Ser Ala Cys His Val His Asp Glu Phe Arg
        355                 360                 365

Thr Ala Ala Val Glu Gly Pro Phe Val Thr Ala Asp
    370                 375                 380


<210> SEQ ID NO 85
<211> LENGTH: 427
<212> TYPE: PRT
<213> ORGANISM: Artificial
<220> FEATURE:
<223> OTHER INFORMATION: Synthetic pBS/MuImPain H#3 construct

<400> SEQUENCE: 85

Ile Asp Lys Leu Asp Glu Pro Gly Arg Arg Gly Ser Phe Val Glu Met
1               5                   10                  15

Val Asp Asn Leu Arg Gly Lys Ser Gly Gln Gly Tyr Tyr Val Glu Met
            20                  25                  30

Thr Val Gly Ser Pro Pro Gln Thr Leu Asn Ile Leu Val Asp Thr Gly
        35                  40                  45

Ser Ser Asn Phe Ala Val Gly Ala Ala Pro His Pro Phe Leu His Arg
    50                  55                  60

Tyr Tyr Gln Arg Gln Leu Ser Ser Thr Tyr Arg Asp Leu Arg Lys Gly
65                  70                  75                  80

Val Tyr Val Pro Tyr Thr Gln Gly Lys Trp Glu Gly Glu Leu Gly Thr
                85                  90                  95

Asp Leu Val Ser Ile Pro His Gly Pro Asn Val Thr Val Arg Ala Asn
            100                 105                 110

Ile Ala Ala Ile Thr Glu Ser Asp Lys Phe Phe Ile Asn Gly Ser Asn
        115                 120                 125

Trp Glu Gly Ile Leu Gly Leu Ala Tyr Ala Glu Ile Ala Arg Pro Asp
    130                 135                 140

Asp Ser Leu Glu Pro Phe Phe Asp Ser Leu Val Lys Gln Thr His Ile
145                 150                 155                 160

Pro Asn Ile Phe Ser Leu Gln Leu Cys Gly Ala Gly Phe Pro Leu Asn
                165                 170                 175

Gln Thr Glu Ala Leu Ala Ser Val Gly Gly Ser Met Ile Ile Gly Gly
            180                 185                 190

Ile Asp His Ser Leu Tyr Thr Gly Ser Leu Trp Tyr Thr Pro Ile Arg
        195                 200                 205

Arg Glu Trp Tyr Tyr Glu Val Ile Ile Val Arg Val Glu Ile Asn Gly
```

-continued

```
    210                 215                 220

Gln Asp Leu Lys Met Asp Cys Lys Glu Tyr Asn Tyr Asp Lys Ser Ile
225                 230                 235                 240

Val Asp Ser Gly Thr Thr Asn Leu Arg Leu Pro Lys Lys Val Phe Glu
                245                 250                 255

Ala Ala Val Lys Ser Ile Lys Ala Ala Ser Ser Thr Glu Lys Phe Pro
            260                 265                 270

Asp Gly Phe Trp Leu Gly Glu Gln Leu Val Cys Trp Gln Ala Gly Thr
        275                 280                 285

Thr Pro Trp Asn Ile Phe Pro Val Ile Ser Leu Tyr Leu Met Gly Glu
    290                 295                 300

Val Thr Asn Gln Ser Phe Arg Ile Thr Ile Leu Pro Gln Gln Tyr Leu
305                 310                 315                 320

Arg Pro Val Glu Asp Val Ala Thr Ser Gln Asp Asp Cys Tyr Lys Phe
                325                 330                 335

Ala Val Ser Gln Ser Ser Thr Gly Thr Val Met Gly Ala Val Ile Met
            340                 345                 350

Glu Gly Phe Tyr Val Val Phe Asp Arg Ala Arg Lys Arg Ile Gly Phe
        355                 360                 365

Ala Val Ser Ala Cys His Val His Asp Glu Phe Arg Thr Ala Ala Val
    370                 375                 380

Glu Gly Pro Phe Val Thr Ala Asp Met Glu Asp Gly Tyr Asn Asn Arg
385                 390                 395                 400

Ile Pro Ala Ala Arg Gly Ile His Phe Ser Gly Arg His Arg Gly Gly
                405                 410                 415

Ala Pro Ile Arg Pro Ile Val Ser Arg Ile Asn
            420                 425


<210> SEQ ID NO 86
<211> LENGTH: 4
<212> TYPE: PRT
<213> ORGANISM: Artificial
<220> FEATURE:
<223> OTHER INFORMATION: Synthetic wild type APP substrate fragment

<400> SEQUENCE: 86

Val Lys Met Asp
1


<210> SEQ ID NO 87
<211> LENGTH: 4
<212> TYPE: PRT
<213> ORGANISM: Artificial
<220> FEATURE:
<223> OTHER INFORMATION: Synthetic Swedish APP substrate fragment

<400> SEQUENCE: 87

Val Asn Leu Asp
1


<210> SEQ ID NO 88
<211> LENGTH: 11
<212> TYPE: PRT
<213> ORGANISM: Artificial
<220> FEATURE:
<223> OTHER INFORMATION: Synthetic Human brain N terminus sequence

<400> SEQUENCE: 88

Glu Thr Asp Glu Glu Pro Glu Glu Pro Gly Arg
1               5                   10
```

-continued

<210> SEQ ID NO 89
<211> LENGTH: 10
<212> TYPE: PRT
<213> ORGANISM: Artificial
<220> FEATURE:
<223> OTHER INFORMATION: Synthetic recombinant 293T N terminus sequence

<400> SEQUENCE: 89

Thr Gln His Gly Ile Arg Leu Pro Leu Arg
1 5 10

<210> SEQ ID NO 90
<211> LENGTH: 9
<212> TYPE: PRT
<213> ORGANISM: Artificial
<220> FEATURE:
<223> OTHER INFORMATION: Synthetic recombinant 293T N terminus sequence

<400> SEQUENCE: 90

Met Val Asp Asn Leu Arg Gly Lys Ser
1 5

<210> SEQ ID NO 91
<211> LENGTH: 10
<212> TYPE: PRT
<213> ORGANISM: Artificial
<220> FEATURE:
<223> OTHER INFORMATION: Synthetic recombinant CosA2 N terminus sequence

<400> SEQUENCE: 91

Gly Ser Phe Val Glu Met Val Asp Asn Leu
1 5 10

<210> SEQ ID NO 92
<211> LENGTH: 10
<212> TYPE: PRT
<213> ORGANISM: Artificial
<220> FEATURE:
<223> OTHER INFORMATION: Synthetic 10 peptide sequence with Swedish
mutation of APP

<400> SEQUENCE: 92

Ser Glu Val Asn Leu Asp Ala Glu Phe Arg
1 5 10

<210> SEQ ID NO 93
<211> LENGTH: 7
<212> TYPE: PRT
<213> ORGANISM: Artificial
<220> FEATURE:
<223> OTHER INFORMATION: Synthetic protein composition containing a
beta-secretase inhibitor molecule
<220> FEATURE:
<221> NAME/KEY: MISC_FEATURE
<222> LOCATION: (1)..(1)
<223> OTHER INFORMATION: Valine has attached hydrogen, acetyl,
t-butoxycarbonyl or carbobenzoyl molecule
<220> FEATURE:
<221> NAME/KEY: MISC_FEATURE
<222> LOCATION: (2)..(2)
<223> OTHER INFORMATION: Xaa = methionine, phenylglycine, n-leucine,
asparagine, phenylalanine, glycine or valine
<220> FEATURE:
<221> NAME/KEY: MISC_FEATURE
<222> LOCATION: (3)..(3)
<223> OTHER INFORMATION: Xaa = statine, acha(cyclohexylmethylstatine) or
phenylstatine (Phe-sta) wherein the phenyl group may optionally
have mono or di-substitution chosen from the group consisting of
Cl, F, Br, methyl or methoxy.

-continued

```
<220> FEATURE:
<221> NAME/KEY: MISC_FEATURE
<222> LOCATION: (4)..(4)
<223> OTHER INFORMATION: Xaa = valine, alpha-aminobutyric acid,
      phenylglycine, or alanine

<400> SEQUENCE: 93

Val Xaa Xaa Xaa Ala Glu Phe
1               5


<210> SEQ ID NO 94
<211> LENGTH: 7
<212> TYPE: PRT
<213> ORGANISM: Artificial
<220> FEATURE:
<223> OTHER INFORMATION: Synthetic protein composition containing a
      beta-secretase inhibitor molecule
<220> FEATURE:
<221> NAME/KEY: MISC_FEATURE
<222> LOCATION: (1)..(1)
<223> OTHER INFORMATION: Valine has attached hydrogen, acetyl,
      t-butoxycarbonyl or carbobenzoyl molecule
<220> FEATURE:
<221> NAME/KEY: MISC_FEATURE
<222> LOCATION: (3)..(3)
<223> OTHER INFORMATION: Xaa = statine molecule

<400> SEQUENCE: 94

Val Met Xaa Val Ala Glu Phe
1               5


<210> SEQ ID NO 95
<211> LENGTH: 7
<212> TYPE: PRT
<213> ORGANISM: Artificial
<220> FEATURE:
<223> OTHER INFORMATION: Synthetic protein composition containing a
      beta-secretase inhibitor molecule
<220> FEATURE:
<221> NAME/KEY: MISC_FEATURE
<222> LOCATION: (1)..(1)
<223> OTHER INFORMATION: Valine is acetylated
<220> FEATURE:
<221> NAME/KEY: MISC_FEATURE
<222> LOCATION: (2)..(2)
<223> OTHER INFORMATION: Xaa is phenylglycine
<220> FEATURE:
<221> NAME/KEY: MISC_FEATURE
<222> LOCATION: (3)..(3)
<223> OTHER INFORMATION: Xaa is statine molecule

<400> SEQUENCE: 95

Val Xaa Xaa Val Ala Glu Phe
1               5


<210> SEQ ID NO 96
<211> LENGTH: 7
<212> TYPE: PRT
<213> ORGANISM: Artificial
<220> FEATURE:
<223> OTHER INFORMATION: Synthetic protein composition containing a
      beta-secretase inhibitor molecule
<220> FEATURE:
<221> NAME/KEY: MISC_FEATURE
<222> LOCATION: (1)..(1)
<223> OTHER INFORMATION: Valine has attached hydrogen, acetyl,
      t-butoxycarbonyl or carbobenzoyl molecule
<220> FEATURE:
<221> NAME/KEY: MISC_FEATURE
<222> LOCATION: (3)..(3)
<223> OTHER INFORMATION: Xaa = statine molecule

<400> SEQUENCE: 96
```

-continued

```
Val Leu Xaa Val Ala Glu Phe
1               5


<210> SEQ ID NO 97
<211> LENGTH: 7
<212> TYPE: PRT
<213> ORGANISM: Artificial
<220> FEATURE:
<223> OTHER INFORMATION: Synthetic protein composition containing a
      beta-secretase inhibitor molecule
<220> FEATURE:
<221> NAME/KEY: MISC_FEATURE
<222> LOCATION: (1)..(1)
<223> OTHER INFORMATION: Val has attached hydrogen, acetyl,
      t-butoxycarbonyl or carbobenzoyl molecule
<220> FEATURE:
<221> NAME/KEY: MISC_FEATURE
<222> LOCATION: (3)..(3)
<223> OTHER INFORMATION: Xaa = statine molecule

<400> SEQUENCE: 97

Val Asn Xaa Val Ala Glu Phe
1               5


<210> SEQ ID NO 98
<211> LENGTH: 7
<212> TYPE: PRT
<213> ORGANISM: Artificial
<220> FEATURE:
<223> OTHER INFORMATION: Synthetic protein composition containing a
      beta-secretase inhibitor molecule
<220> FEATURE:
<221> NAME/KEY: MISC_FEATURE
<222> LOCATION: (1)..(1)
<223> OTHER INFORMATION: Val has attached hydrogen, acetyl,
      t-butoxycarbonyl or carbobenzoyl molecule
<220> FEATURE:
<221> NAME/KEY: MISC_FEATURE
<222> LOCATION: (3)..(3)
<223> OTHER INFORMATION: Xaa = statine molecule

<400> SEQUENCE: 98

Val Phe Xaa Val Ala Glu Phe
1               5


<210> SEQ ID NO 99
<211> LENGTH: 7
<212> TYPE: PRT
<213> ORGANISM: Artificial
<220> FEATURE:
<223> OTHER INFORMATION: Synthetic protein composition containing a
      beta-secretase inhibitor molecule
<220> FEATURE:
<221> NAME/KEY: MISC_FEATURE
<222> LOCATION: (3)..(3)
<223> OTHER INFORMATION: Xaa = phenylstatine molecule

<400> SEQUENCE: 99

Val Met Xaa Val Ala Glu Phe
1               5


<210> SEQ ID NO 100
<211> LENGTH: 7
<212> TYPE: PRT
<213> ORGANISM: Artificial
<220> FEATURE:
<223> OTHER INFORMATION: Synthetic protein composition containing a
      beta-secretase inhibitor molecule
<220> FEATURE:
<221> NAME/KEY: MISC_FEATURE
<222> LOCATION: (1)..(1)
```

-continued

```
<223> OTHER INFORMATION: Val is acetylated is Acetyl group
<220> FEATURE:
<221> NAME/KEY: MISC_FEATURE
<222> LOCATION: (3)..(3)
<223> OTHER INFORMATION: Xaa = statine molecule

<400> SEQUENCE: 100

Val Met Xaa Val Ala Glu Phe
1               5


<210> SEQ ID NO 101
<211> LENGTH: 22
<212> TYPE: DNA
<213> ORGANISM: Homo sapiens

<400> SEQUENCE: 101

cggccggagg ggcagctttg tg                                               22
```